US012558558B2

(12) United States Patent
Freeman et al.

(10) Patent No.: US 12,558,558 B2
(45) Date of Patent: Feb. 24, 2026

(54) PORTABLE MEDICAL TREATMENT APPARATUS WITH INTERACTIVE GUIDANCE AND CARDIOPULMONARY RESUSCITATIVE FUNCTIONALITY

(71) Applicant: ZOLL Medical Corporation, Chelmsford, MA (US)

(72) Inventors: Gary A. Freeman, Waltham, MA (US); Christopher L. Kaufman, Somerville, MA (US); John P. Pierson, Tewksbury, MA (US); Kristopher M. Edgell, Shreveport, LA (US)

(73) Assignee: ZOLL Medical Corporation, Chelmsford, MA (US)

( * ) Notice: Subject to any disclaimer, the term of this patent is extended or adjusted under 35 U.S.C. 154(b) by 439 days.

(21) Appl. No.: 17/908,099

(22) PCT Filed: Mar. 26, 2021

(86) PCT No.: PCT/US2021/024421
§ 371 (c)(1),
(2) Date: Aug. 30, 2022

(87) PCT Pub. No.: WO2021/202292
PCT Pub. Date: Oct. 7, 2021

(65) Prior Publication Data
US 2023/0025409 A1     Jan. 26, 2023

(51) Int. Cl.
| | | |
|---|---|---|
| *A61N 1/39* | (2006.01) | |
| *A61N 1/02* | (2006.01) | |
| *G16H 40/63* | (2018.01) | |

(52) U.S. Cl.
CPC ........... *A61N 1/3968* (2013.01); *A61N 1/025* (2013.01); *A61N 1/39044* (2017.08);
(Continued)

(58) Field of Classification Search
CPC .. A61N 1/3968; A61N 1/025; A61N 1/39044; A61N 1/3993; A61N 1/0476;
(Continued)

(56) References Cited

U.S. PATENT DOCUMENTS

| | | | |
|---|---|---|---|
| 6,327,497 | B1 | 12/2001 | Kirchgeorg et al. |
| 7,706,878 | B2 * | 4/2010 | Freeman ................. A61G 7/07 |
| | | | 607/6 |
| 9,596,991 | B2 * | 3/2017 | Choi ...................... G16H 50/20 |
| 9,788,734 | B2 | 10/2017 | Tan et al. |
| 2003/0114885 | A1 | 6/2003 | Nova et al. |
| 2003/0233129 | A1 * | 12/2003 | Matos ................. A61N 1/0476 |
| | | | 607/5 |

(Continued)

FOREIGN PATENT DOCUMENTS

| | | |
|---|---|---|
| WO | 2019112844 A1 | 6/2019 |
| WO | 2021202292 A1 | 10/2021 |

OTHER PUBLICATIONS

Screen Capture and Citations from Vimeo video clip entitled "#bystanderssavelives #2.". Retrieved from internet: https://vimeo.com /201879344 (Year: 2017).*

*Primary Examiner* — Niketa Patel
*Assistant Examiner* — Attiya Sayyada Hussaini
(74) *Attorney, Agent, or Firm* — Mintz, Levin, Cohn, Ferris, Glovsky and Popeo, P.C. US

(57) ABSTRACT

A portable medical treatment apparatus and interactive application that leads a user through a medically acceptable query flow for treating medical emergencies, including cardiac or pulmonary medical emergencies that can be treated with electrotherapy and other medical emergencies.

20 Claims, 24 Drawing Sheets

(52) U.S. Cl.
CPC ......... *A61N 1/3925* (2013.01); *A61N 1/3993*
(2013.01); *G16H 40/63* (2018.01)

(58) Field of Classification Search
CPC .... A61N 1/0492; A61N 1/046; A61N 1/3925;
G16H 40/63; G16H 50/20; G16H 20/30;
G16H 40/67; A61H 31/005; A61H
2201/5061; A61H 2201/5064; A61H
2201/5084; A61H 2201/5092; A61F
17/00; A45C 2011/007; G09B 23/288;
A61B 5/0006; A61B 5/411; A61B 5/7445
See application file for complete search history.

(56) References Cited

U.S. PATENT DOCUMENTS

| | | | |
|---|---|---|---|
| 2006/0094949 A1* | 5/2006 | Coonce | A61B 5/747 |
| | | | 600/407 |
| 2013/0220859 A1 | 8/2013 | Roach et al. | |
| 2014/0372137 A1* | 12/2014 | Tryon | G16H 10/60 |
| | | | 705/2 |
| 2016/0287470 A1 | 10/2016 | Lewis et al. | |
| 2017/0266399 A1 | 9/2017 | Campana et al. | |
| 2017/0340221 A1 | 11/2017 | Cronin et al. | |
| 2019/0043615 A1* | 2/2019 | Subbarao | G16H 40/63 |
| 2020/0253679 A1* | 8/2020 | Mann | G07F 11/004 |
| 2021/0093876 A1* | 4/2021 | Montague | G16H 80/00 |

* cited by examiner

Option A to Navigate through Query Flow

Option B to Navigate through Query Flow

3270

Option C to Navigate through Query Flow

3290

Option D to Navigate through Query Flow

3292

User removes item

3010

3002

3210

3044

3044a

3045

Perform an adapted
interactive query flow

3294

700

702

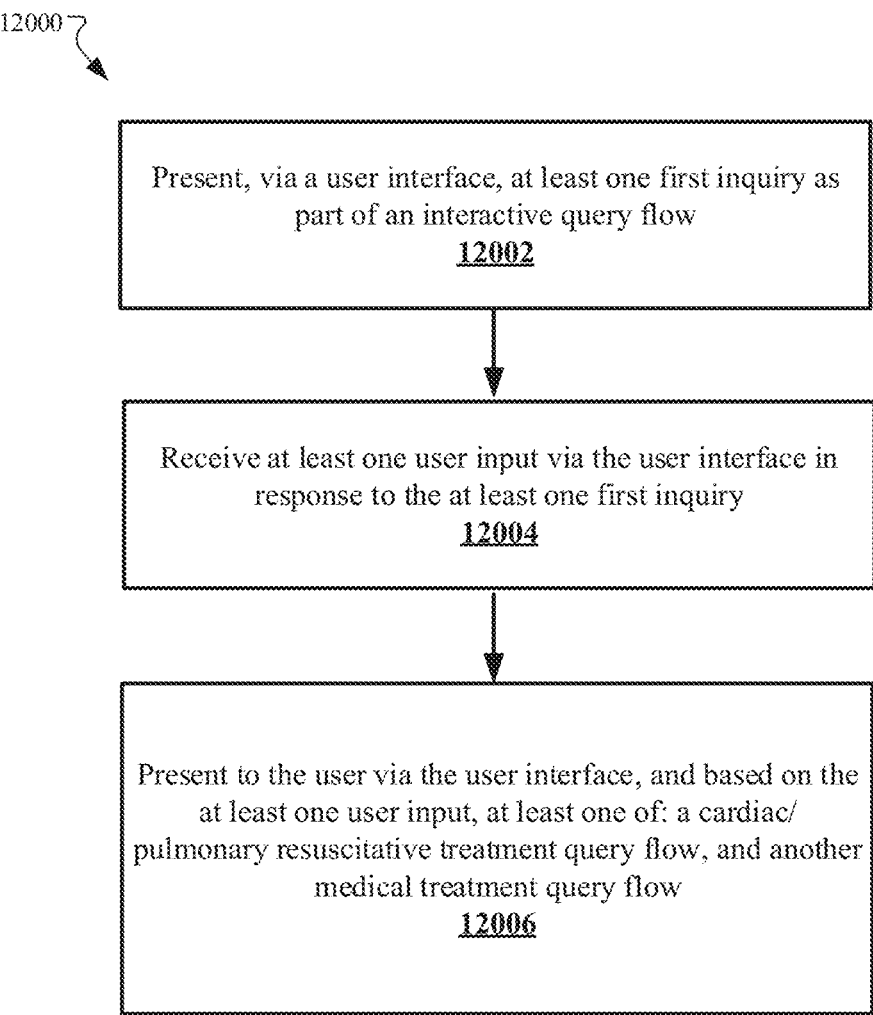

12000

Present, via a user interface, at least one first inquiry as part of an interactive query flow
12002

Receive at least one user input via the user interface in response to the at least one first inquiry
12004

Present to the user via the user interface, and based on the at least one user input, at least one of: a cardiac/pulmonary resuscitative treatment query flow, and another medical treatment query flow
12006

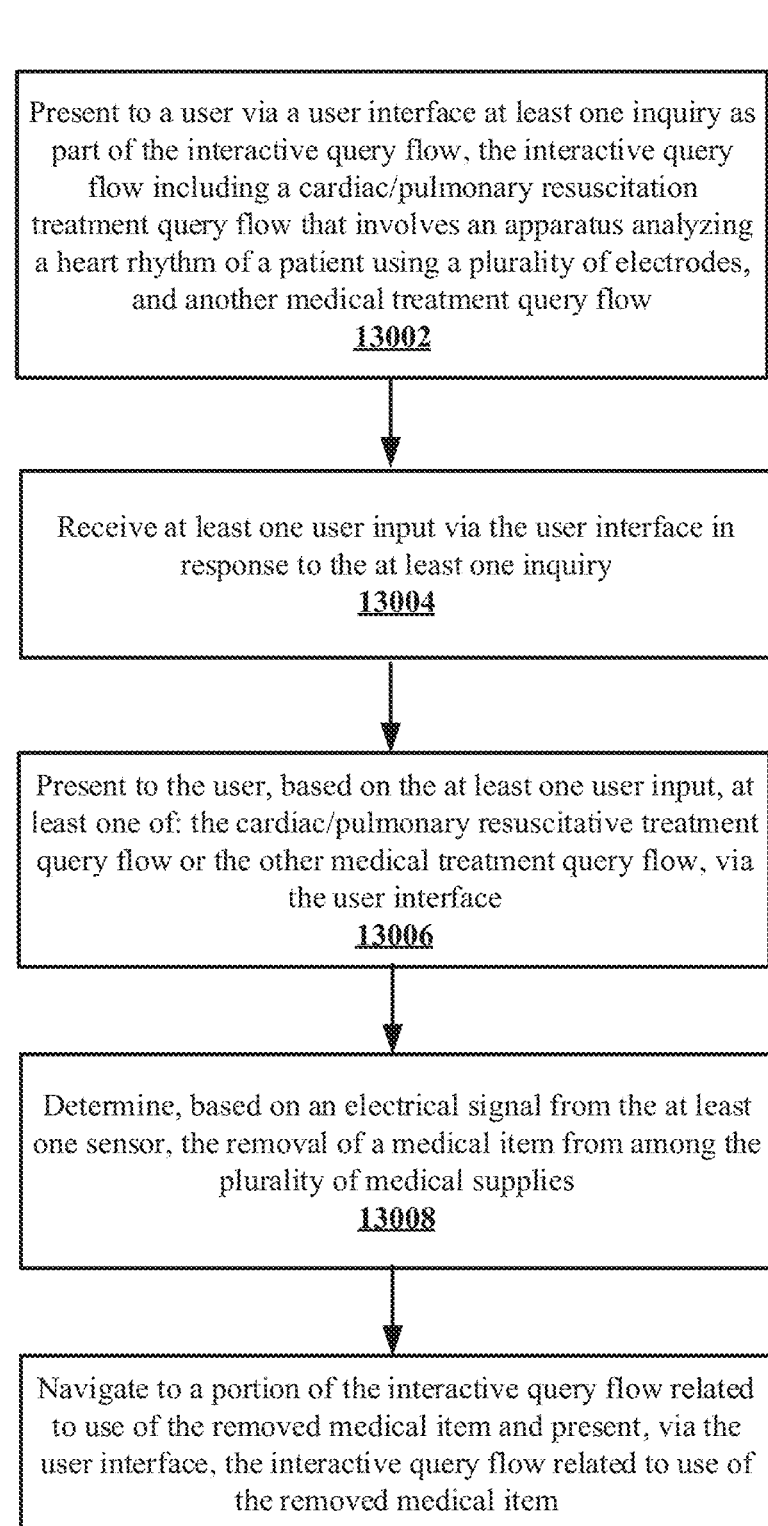

Present to a user via a user interface at least one inquiry as part of the interactive query flow, the interactive query flow including a cardiac/pulmonary resuscitation treatment query flow that involves an apparatus analyzing a heart rhythm of a patient using a plurality of electrodes, and another medical treatment query flow
13002

Receive at least one user input via the user interface in response to the at least one inquiry
13004

Present to the user, based on the at least one user input, at least one of: the cardiac/pulmonary resuscitative treatment query flow or the other medical treatment query flow, via the user interface
13006

Determine, based on an electrical signal from the at least one sensor, the removal of a medical item from among the plurality of medical supplies
13008

Navigate to a portion of the interactive query flow related to use of the removed medical item and present, via the user interface, the interactive query flow related to use of the removed medical item
13010

FIG. 13

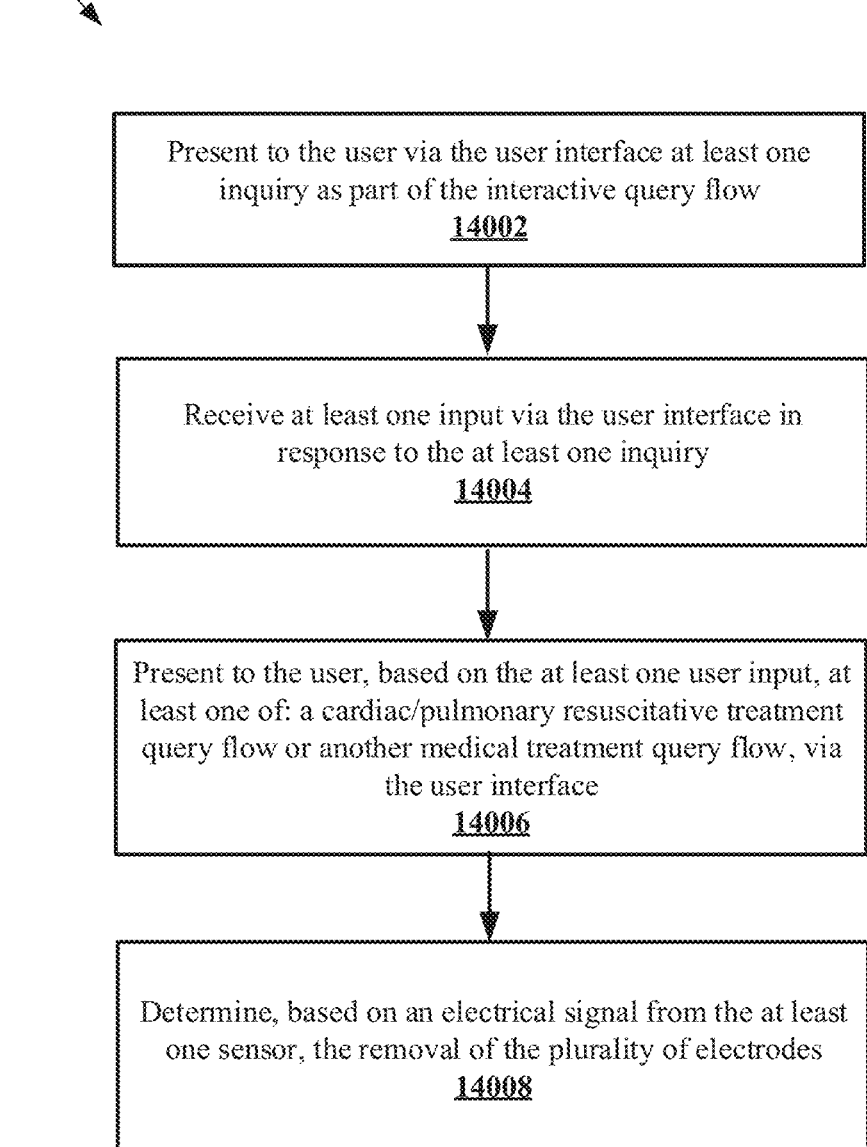

14000

Present to the user via the user interface at least one inquiry as part of the interactive query flow
14002

Receive at least one input via the user interface in response to the at least one inquiry
14004

Present to the user, based on the at least one user input, at least one of: a cardiac/pulmonary resuscitative treatment query flow or another medical treatment query flow, via the user interface
14006

Determine, based on an electrical signal from the at least one sensor, the removal of the plurality of electrodes
14008

Navigate to the cardiac/pulmonary resuscitative treatment query flow and present, via the user interface, guidance related to use of the removed plurality of electrodes
14010

FIG. 14

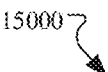

15000

Analyze, by a portable medical treatment apparatus during a first time period, heart rhythm of a patient that is sensed using a plurality of defibrillation electrodes of the portable medical treatment apparatus
15002

Determine, by the portable medical treatment apparatus, that the heart rhythm that is sensed during the first time period does not satisfy criteria for delivering a shock to the patient
15004

Present, by the portable medical treatment apparatus in response to the portable medical treatment apparatus having determined that the heart rhythm that is sensed during the first time period does not satisfy criteria for delivering the shock to the patient, an interactive query flow configured to guide a user of the portable medical treatment apparatus in assessing and treating non-cardiac arrest medical emergencies
15006

Analyze, by the portable medical treatment apparatus during a second time period that occurs after the portable medical treatment apparatus has presented multiple prompts and received multiple user responses as part of the interactive query flow, the heart rhythm of the patient using the plurality of defibrillation electrodes
15008

FIG. 15

PORTABLE MEDICAL TREATMENT APPARATUS WITH INTERACTIVE GUIDANCE AND CARDIOPULMONARY RESUSCITATIVE FUNCTIONALITY

CROSS-REFERENCE TO RELATED APPLICATIONS

The present application claims priority to and is the 35 U.S.C. 371 United States National Phase application based on International Patent Application No. PCT/US21/24421, filed on Mar. 26, 2021, entitled "PORTABLE MEDICAL TREATMENT APPARATUS WITH INTERACTIVE GUIDANCE AND CARDIOPULMONARY RESUSCITATIVE FUNCTIONALITY," which claims priority to U.S. application Ser. No. 63/002,962 filed on Mar. 31, 2020, entitled "PORTABLE MEDICAL TREATMENT APPARATUS WITH INTERACTIVE GUIDANCE AND CARDIOPULMONARY RESUSCITATIVE FUNCTIONALITY", which are hereby incorporated by reference in their entireties.

TECHNICAL FIELD

The present disclosure relates to portable medical treatment systems, apparatus and processes that provide both cardiac/pulmonary resuscitative functionality and interactive guidance in administering medical treatment.

BACKGROUND

Various different types of medical first aid kits exist to supply first aid to an injured person. Some such first aid kits also provide written and/or audible instructions for how to treat victims, using the medical supplies contained within the first aid kits. First aid kits may be stored at places where people congregate and therefore medical emergencies are likely to occur (e.g., at workplaces, stores, and schools). In an emergency, a caregiver may locate a portable first aid kit and carry the portable first aid kit to a location of a victim. The caregiver may use the supplies in the portable first aid kit to treat one or more medical emergencies from which the victim may be suffering.

SUMMARY

In one aspect, a system for portable medical treatment and guidance apparatus with resuscitative functionality is provided. The apparatus can include: a case having at least one compartment, a plurality of medical supplies housed within the at least one compartment, at least one capacitor housed within the case, the at least one capacitor configured to store energy sufficient for providing an electrical defibrillation discharge, a user interface mechanically coupled to the case and configured to provide an interactive query flow for assisting a user in providing medical treatment, a removable cardiac/pulmonary resuscitative subsystem being communicatively coupled to the case and including a plurality of electrodes configured to be electrically coupled to the at least one capacitor via an electrical connection between the removable cardiac/pulmonary resuscitative subsystem and the case, and at least one processor and memory mechanically coupled to the case and electrically coupled to the at least one capacitor and the user interface. The at least one processor and memory can be configured to: present via the user interface at least one inquiry as part of the interactive query flow, receive at least one user input via the user interface in response to the at least one inquiry, and present to the user via the user interface and based on the at least one user input at least one of: a cardiac/pulmonary resuscitative treatment protocol portion of the interactive query flow, and an other medical treatment portion of the interactive query flow.

In some implementations, the other medical treatment portion of the interactive query flow provides instructions for use of at least one of the plurality of medical supplies. The other medical treatment portion of the interactive query flow can include instructions for treating a condition other than cardiac arrest. The condition other than cardiac arrest can include at least one of: bleeding, seizure, burn, bone fracture, drug overdose, allergic reaction, choking, impaled object, trapped limb, severed body part, childbirth, or confusion. The plurality of medical supplies can include at least one of: gloves, a wound dressing, hemostatic gauze, a pressuring dressing, a burn dressing, a compression dressing, a splint, a tourniquet, a drug dosage, and an emergency blanket. The condition other than cardiac arrest can include bleeding and the at least one inquiry can include a request for the user to input where the patient is bleeding.

In some implementations, the condition other than cardiac arrest can include seizures and the at least one inquiry can include a request for the user to ensure the patient is lying in the supine position, and the condition other than cardiac arrest can include choking and the at least one inquiry can include a request for the user to perform an abdominal thrust. The request for the user to input where the patient is bleeding can include a presentation on the user interface of a body with selectable regions to indicate where the patient is bleeding. The at least one input can include a selected region that indicates where the victim is bleeding and the instructions for use of the at least one of the plurality of medical supplies include guidance for use of at least one of: the wound dressing, the hemostatic gauze, the pressuring dressing, the burn dressing, the compression dressing, and the tourniquet. The cardiac/pulmonary resuscitative treatment portion of the interactive query protocol provides instructions for treating at least one of: a cardiac arrest condition and a respiratory distress condition. The cardiac/pulmonary resuscitative treatment portion of the interactive query protocol provides instructions for use of the plurality of electrodes. The plurality of electrodes can be configured to provide electrotherapy from the at least one capacitor to a patient, and to obtain ECG signals of the patient. The at least one processer and memory can be configured to analyze the obtained ECG signals to determine whether the patient is in need of a defibrillation shock and, if needed, provide the defibrillation shock via the plurality of electrodes. The at least one processor and memory can be configured to interrupt the interactive query flow to analyze the obtained ECG signals. The at least one processor and memory can be configured to provide continuous background monitoring via the plurality of electrodes to determine whether to interrupt the interactive query flow. The instructions for treating the cardiac arrest condition include prompts to apply cardiopulmonary resuscitation. The instructions for treating the cardiac arrest condition include prompts to apply at least one of: chest compressions and ventilations. The apparatus can further include a motion sensor configured to provide chest compression information during the application of the chest compressions. The apparatus can further include a manual ventilation unit for applying manual ventilations and a flow sensor configured to provide ventilation information during the application of the ventilations. The at least one user input can include an indication that the patient is unconscious and not breathing, and based at least in part on the indication, the at least one processor and memory can be configured to present the user with the cardiac/pulmonary resuscitative treatment portion of the interactive query protocol. The user interface can include at least one of: buttons, soft keys, a knob, a dial, or a touchscreen display, configured to receive the at least one input in response to the at least one inquiry. The apparatus can further include a handle or strap coupled to the case of the apparatus, wherein the handle or strap allows the apparatus to be human carryable. The at least one processor and memory can be configured to start a timer upon beginning the interactive query flow. The at least one processor and memory can be configured to provide continuous background monitoring during the interactive query flow. The apparatus can further include a sensor adapted to identify removal of a medical item from among the plurality of medical supplies, the plurality of electrodes, or both a medical item from among the plurality of medical supplies and the plurality of electrodes. The at least one processor and memory can be configured to determine that the sensor has identified removal of a removed medical item from among the plurality of medical supplies. The at least one processor and memory can be configured to navigate to a portion of the interactive query flow related to use of the removed medical item responsive to having determined that the sensor has identified removal of the removed medical item. The removed medical item can include gauze, and the portion of the interactive query flow related to use of the gauze can include a portion of the interactive query flow related to an injury that causes blood loss. The removed medical item can include the plurality of electrodes, and the portion of the interactive query flow related to use of the plurality of electrodes can include part of the cardiac/pulmonary resuscitative treatment protocol portion of the interactive query flow. The at least one processor and memory can be configured to present via the user interface an inquiry as to a level of medical training of the user, and receive a response to the inquiry as to the level of medical training of the user. The at least one processor and memory can be configured to adjust the interactive query flow based on the response to the inquiry as to the level of medical training of the user.

In another aspect, a portable medical treatment and guidance apparatus with electrotherapy functionality is provided. The apparatus includes: a case having at least one compartment, a plurality of medical supplies housed within the at least one compartment, at least one capacitor housed within the case, the at least one capacitor configured to store energy sufficient for providing an electrical defibrillation discharge, a plurality of electrodes housed within the at least one compartment and configured to be electrically coupled to the at least one capacitor, a sensor adapted to identify removal of a medical item from among the plurality of medical supplies, the plurality of electrodes, or both a medical item from among the plurality of medical supplies and the plurality of electrodes, a user interface mechanically coupled to the case and configured to provide an interactive query flow, and at least one processor and memory mechanically coupled to the case and electrically coupled to the at least one capacitor and the user interface. The at least one processor and memory can be configured to: present to a user via the user interface at least one inquiry as part of the interactive query flow, the interactive query flow including a cardiac/pulmonary resuscitative treatment protocol portion that involves the apparatus analyzing a heart rhythm of a patient using the plurality of electrodes, and an other medical treatment portion, receive at least one user input via the user interface in response to the at least one inquiry, present to the user, based on the at least one user input, at least one of: the cardiac/pulmonary resuscitative treatment protocol portion of the interactive query flow or the other medical treatment portion of the interactive query flow, via the user interface, determine that the sensor has identified removal of a removed medical item from among the plurality of medical supplies, and navigate to a portion of the interactive query flow related to use of the removed medical item responsive to having determined that the sensor has identified removal of the removed medical item.

In some implementations, the other medical treatment portion of the interactive query flow provides instructions for use of at least one of the plurality of medical supplies. The other medical treatment portion of the interactive query flow can include instructions for treating a condition other than cardiac arrest. The condition other than cardiac arrest can include at least one of: bleeding, seizure, burn, bone fracture, drug overdose, allergic reaction, choking, impaled object, trapped limb, severed body part, child birth, or confusion. The plurality of medical supplies can include at least one of: gloves, a wound dressing, hemostatic gauze, a pressuring dressing, a burn dressing, a compression dressing, a splint, a tourniquet, a drug dosage, and an emergency blanket. The condition other than cardiac arrest can include bleeding and the at least one inquiry can include a request for the user to input where the patient is bleeding. The condition other than cardiac arrest can include the seizing and the at least one inquiry can include a request for the user to ensure the patient is on the back, and the condition other than cardiac arrest can include choking and the at least one inquiry can include a request for the user to perform an abdominal thrust. The request for the user to input where the patient is bleeding can include a presentation on the user interface of a body with selectable regions to indicate where the patient is bleeding. The at least one input can include a selected region that indicates where the victim is bleeding and the instructions for use of the at least one of the plurality of medical supplies include guidance for use of at least one of: the wound dressing, the hemostatic gauze, the pressuring dressing, the burn dressing, the compression dressing, and the tourniquet. The cardiac/pulmonary resuscitative treatment portion of the interactive query protocol provides instructions for treating at least one of: a cardiac arrest condition and a respiratory distress condition. The cardiac/pulmonary resuscitative treatment portion of the interactive query protocol provides instructions for use of the plurality of electrodes. The plurality of electrodes can be configured to provide electrotherapy from the at least one capacitor to a patient, and to obtain ECG signals of the patient. The at least one processer and memory can be configured to analyze the obtained ECG signals to determine whether the patient is in need of a defibrillation shock and, if needed, provide the defibrillation shock via the plurality of electrodes. The at least one processor and memory can be configured to interrupt the interactive query flow to analyze the obtained ECG signals. The at least one processor and memory can be configured to provide continuous background monitoring via the plurality of electrodes to determine whether to interrupt the interactive query flow. The instructions for treating the cardiac arrest condition include prompts to apply cardiopulmonary resuscitation. The instructions for treating the cardiac arrest condition include prompts to apply at least one of: chest compressions and ventilations. The apparatus can further include a motion sensor configured to provide chest compression information during the application of the chest compressions. The apparatus can further include a manual ventilation unit for applying manual ventilations and a flow sensor configured to provide ventilation information during the application of the ventilations. The at least one user input can include an indication that the patient is unconscious and not breathing, and based at least in part on the indication, the at least one processor and memory can be configured to present the user with the cardiac/pulmonary resuscitative treatment portion of the interactive query protocol. The user interface can include at least one of: buttons, soft keys, a knob, a dial, or a touchscreen display, configured to receive the at least one input in response to the at least one inquiry. The apparatus can further include a handle or strap coupled to the case of the apparatus, wherein the handle or strap allows the apparatus to be human carryable. The at least one processor and memory can be configured to start a timer upon beginning the interactive query flow. The at least one processor and memory can be configured to provide continuous background monitoring during the interactive query flow. The removed medical item can include gauze, and the portion of the interactive query flow related to use of the gauze can include a portion of the interactive query flow related to an injury that causes blood loss. The removed medical item can include gauze, and the portion of the interactive query flow related to use of the gauze can include part of the other medical treatment portion of the interactive query flow related to an injury that causes blood loss. The removed medical item can include the plurality of electrodes, and the portion of the interactive query flow related to use of the plurality of electrodes can include part of the cardiac/pulmonary resuscitative treatment protocol portion of the interactive query flow. The apparatus can further include a removable cardiac/pulmonary resuscitative subsystem to which the plurality of electrodes are adapted to attach, the removable resuscitative subsystem being electrically connected to the case and including a user input device or a user output device, wherein the at least one processor and memory can be configured to interact with the user input device or the user output device during presentation of the cardiac/pulmonary resuscitative treatment protocol portion of the interactive query flow. The at least one processor and memory can be configured to present via the user interface an inquiry as to a level of medical training of the user, and receive a response to the inquiry as to the level of medical training of the user. The at least one processor and memory can be configured to adjust the interactive query flow based on the response to the inquiry as to the level of medical training of the user.

In another aspect, an automated external defibrillator for providing guidance in administering emergency medical treatment is provided. The automated external defibrillator includes: at least one capacitor configured to provide electrotherapy, a plurality of electrodes configured to be electrically coupled to the at least one capacitor, a sensor adapted to identify removal of the plurality of electrodes, a user interface configured to provide an interactive query flow that can include a cardiac/pulmonary resuscitative treatment protocol portion that involves analysis of a heart rhythm of a patient using the plurality of electrodes and an other medical treatment portion, and at least one processor and memory electrically coupled to the at least one capacitor, the plurality of electrodes, and the user interface, the at least one processor and memory configured to: present to the user via the user interface at least one inquiry as part of the interactive query flow, receive at least one input via the user interface in response to the at least one inquiry, present to the user, based on the at least one user input, at least one of: a cardiac/pulmonary resuscitative treatment protocol portion of the interactive query flow or an other medical treatment portion of the interactive query flow, via the user interface, determine that the sensor has identified removal of the plurality of electrodes, and navigate to part of the cardiac/pulmonary resuscitative treatment protocol portion of the interactive query flow responsive to having determined that the sensor has identified removal of the plurality of electrodes.

In some implementations, the other medical treatment portion of the interactive query flow provides instructions for use of at least one medical supply. The other medical treatment portion of the interactive query flow can include instructions for treating a medical condition other than cardiac arrest. The medical condition other than cardiac arrest can include at least one of: bleeding, seizure, burn, bone fracture, drug overdose, allergic reaction, choking, impaled object, trapped limb, severed body part, childbirth, or confusion. The instructions for use of the at least one medical supply can include a prompt to obtain the at least one medical supply from an external source that is external to the automated external defibrillator. The automated external defibrillator can further include a plurality of medical supplies referenced by the instructions for use of the at least one medical supply. The plurality of medical supplies can include at least one of: gloves, a wound dressing, hemostatic gauze, a pressuring dressing, a burn dressing, a compression dressing, a splint, a tourniquet, a drug dosage, and an emergency blanket. The condition other than cardiac arrest can include bleeding and the at least one inquiry can include a request for the user to input where the patient is bleeding. The condition other than cardiac arrest can include the seizing and the at least one inquiry can include a request for the user to ensure the patient is on the back, and the condition other than cardiac arrest can include choking and the at least one inquiry can include a request for the user to perform an abdominal thrust. The request for the user to input where the patient is bleeding can include a presentation on the user interface of a body with selectable regions to indicate where the patient is bleeding. The at least one input can include a selected region that indicates where the victim is bleeding and the instructions for use of at least one medical supply can include guidance for use of at least one of: the wound dressing, the hemostatic gauze, the pressuring dressing, the burn dressing, the compression dressing, or the tourniquet. The cardiac/pulmonary resuscitative treatment portion of the interactive query protocol provides instructions for treating a cardiac arrest condition. The cardiac/pulmonary resuscitative treatment portion of the interactive query protocol provides instructions for use of the plurality of electrodes. The plurality of electrodes can be configured to provide electrotherapy from the at least one capacitor to the patient, and to obtain ECG signals of the patient. The at least one processer and memory can be configured to analyze the ECG signal to determine whether the patient is in need of a defibrillation shock and, if needed, provide the defibrillation shock via the plurality of electrodes. The at least one processor and memory can be configured to interrupt the interactive query flow to analyze the ECG signals. The instructions for treating a cardiac arrest condition include prompts to apply cardiopulmonary resuscitation. The instructions for treating a cardiac arrest condition include prompts to apply at least one of: chest compressions or ventilations. The instructions for treating the cardiac arrest condition include prompts to apply chest compressions, and the automated external defibrillator further can include a motion sensor configured to provide chest compression information during the chest compressions. The automated external defibrillator can further include a manual ventilation unit for applying manual ventilations, and a flow sensor configured to provide ventilation information during the ventilations. The at least one user input can include an indication that the patient is unconscious and not breathing, and based at least in part on the indication, the at least one processor and memory can be configured to present the user with the cardiac/pulmonary resuscitative treatment portion of the interactive query protocol. The user interface can include at least one of: buttons, soft keys, a knob, a dial, or a touchscreen display, configured to receive the at least one input in response to the at least one inquiry. The at least one processor can be configured to start a timer upon beginning the interactive query flow. The apparatus can further include a plurality of medical supplies, wherein the other medical treatment portion of the interactive query flow provides instructions for use of at least one of the plurality of medical supplies, wherein the sensor or another sensor is adapted to identify removal of a removed medical item from the plurality of medical supplies, wherein the at least one processor and memory can be configured to navigate to part of the other medical treatment portion of the interactive query flow responsive to having determined that the sensor has identified removal of the removed medical item. The removed medical item can include gauze, and the part of the other medical treatment portion of the interactive query flow is part of the interactive query flow related to an injury that causes blood loss. The apparatus can further include a removable cardiac/pulmonary resuscitative subsystem to which the plurality of electrodes is adapted to attach. The removable cardiac/pulmonary resuscitative subsystem can be electrically connected to the case and including a user input device or a user output device, wherein the at least one processor and memory can be configured to interact with the user input device or the user output device during presentation of the cardiac/pulmonary resuscitative treatment protocol portion of the interactive query flow.

In another aspect, a method for treating a patient using a portable medical treatment apparatus is provided. The method includes: analyzing, by the portable medical treatment apparatus during a first time period, heart rhythm of the patient that is sensed using a plurality of defibrillation electrodes of the portable medical treatment apparatus, determining, by the portable medical treatment apparatus, that the heart rhythm that is sensed during the first time period does not satisfy criteria for delivering a shock to the patient, presenting, by the portable medical treatment apparatus in response to the portable medical treatment apparatus having determined that the heart rhythm that is sensed during the first time period does not satisfy criteria for delivering the shock to the patient, an interactive query flow configured to guide a user of the portable medical treatment apparatus in assessing and treating non-cardiac arrest medical emergencies, and subsequently analyzing, by the portable medical treatment apparatus during a second time period that occurs after the portable medical treatment apparatus has presented multiple prompts and received multiple user responses as part of the interactive query flow, the heart rhythm of the patient using the plurality of defibrillation electrodes.

In some implementations, the method can further include: interrupting, by the portable medical treatment apparatus, the presentation of the interactive query flow in order to perform the subsequent analysis of the heart rhythm of the patient during the second time period, determining, by the portable medical treatment apparatus, that the heart rhythm that is sensed during the second time period does not satisfy criteria for delivering the shock to the patient, and continuing, by the portable medical treatment apparatus, the presentation of the interactive query flow, responsive to the portable medical treatment apparatus having determined that the heart rhythm that is sensed during the second time period does not satisfy criteria for delivering the shock to the patient. Interrupting the presentation of the interactive query flow in order to perform the subsequent analysis of the heart rhythm of the patient can include presenting, by the portable medical treatment apparatus, an instruction to not touch the patient. Interrupting the presentation of the interactive query flow in order to perform the subsequent analysis of the heart rhythm of the patient can include changing a presentation on a display of the portable medical treatment apparatus from a first interface that relates to assessment or treatment of a non-cardiac arrest medical emergency to a second interface that indicates that the portable medical treatment apparatus is performing the subsequent analysis of the heart rhythm, and continuing the presentation of the interactive query flow can include changing the presentation on the display of the portable medical treatment apparatus from the second interface that indicates that the portable medical treatment apparatus is performing the subsequent analysis of the heart rhythm back to the first interface that relates to assessment or treatment of the non-cardiac arrest medical emergency. Continuing the presentation of the interactive query flow can include the portable medical treatment apparatus presenting a plurality of prompts and receiving a plurality of user responses as part of the interactive query flow, and the method further can include: identifying, by the portable medical treatment apparatus responsive to the portable medical treatment apparatus having presented the plurality of prompts and having received the plurality of user responses as part of the interactive query flow, that the patient is suffering from a first non-cardiac arrest medical condition, instructing, by the portable medical treatment apparatus responsive to the portable medical treatment apparatus having identified that the patient is suffering from the first non-cardiac arrest medical condition, the user to retrieve a first medical supply item from storage of the portable medical treatment apparatus and treat the first non-cardiac arrest medical condition of the patient using the first medical supply item. The first non-cardiac arrest medical condition can include bleeding by the patient, the first medical supply item can include a dressing, and instructing the user to treat the first non-cardiac arrest medical condition of the patient using the first medical supply item can include the portable medical treatment apparatus presenting information that indicates how to apply the dressing to the patient. The method can further include: interrupting, by the portable medical treatment apparatus, the interactive query flow in order to perform the subsequent analysis of the heart rhythm of the patient during the second time period, determining, by the portable medical treatment apparatus, that the heart rhythm that is sensed during the second time period does satisfy criteria for delivering the shock to the patient, delivering, by the portable medical treatment apparatus in response to the portable medical treatment apparatus having determined that the heart rhythm that is sensed during the second time period does satisfy the criteria for delivering the shock to the patient, the shock to the patient using the plurality of defibrillation electrodes of the portable medical treatment apparatus, subsequently analyzing, by the portable medical treatment apparatus during a third time period that occurs after the portable medical treatment apparatus delivered the shock to the patient, the heart rhythm of the patient using the plurality of defibrillation electrodes, determining, by the portable medical treatment apparatus, that the heart rhythm that is sensed during the third time period does not satisfy criteria for delivering the shock to the patient, and continuing, by the portable medical treatment apparatus, the presentation of the interactive query flow responsive to the portable medical treatment apparatus having determined that the heart rhythm that is sensed during the third time period does not satisfy criteria for delivering the shock to the patient. The method can further include: starting, by the portable medical treatment apparatus, a timer responsive to the portable medical treatment apparatus determining that the heart rhythm that is sensed during the first time period does not satisfy criteria for delivering a shock to the patient, determining, by the portable medical treatment apparatus, that the timer satisfies criteria for initiating an analysis of the heart rhythm of the patient, wherein the portable medical treatment apparatus initiates the subsequent analysis of the heart rhythm of the patient during the second time period responsive to the portable medical treatment apparatus having determined that the timer satisfies the criteria for initiating the analysis of the heart rhythm of the patient. The method can further include presenting, by the portable medical treatment before the portable medical treatment apparatus analyzes the heart rhythm of the patient during the first time period, the interactive query flow configured to guide the user of the portable medical treatment apparatus in assessing and treating non-cardiac arrest medical emergencies, wherein the portable medical treatment apparatus performs the analysis of the heart rhythm of the patient during the first time period after the portable medical treatment apparatus has presented a plurality of prompts and received a plurality of user responses as part of the interactive query flow, the plurality of user responses indicating that the patient is not suffering from at least one non-cardiac arrest medical emergency and indicating that the patient has a condition indicative of a cardiac arrest medical emergency. The portable medical treatment apparatus performs the analysis of the heart rhythm of the patient during the first time period before the portable medical treatment apparatus has received any user response as part of the interactive query flow that indicates that the patient is not suffering from a non-cardiac arrest medical emergency.

BRIEF DESCRIPTIONS OF THE DRAWINGS

Many advantages of the present disclosure will be apparent to those skilled in the art with a reading of this specification in conjunction with the attached drawings, wherein like reference numerals are applied to like elements and wherein:

FIGS. 12-15 depict example processes performed by a portable medical treatment apparatus.

DETAILED DESCRIPTION

Figure 1A:
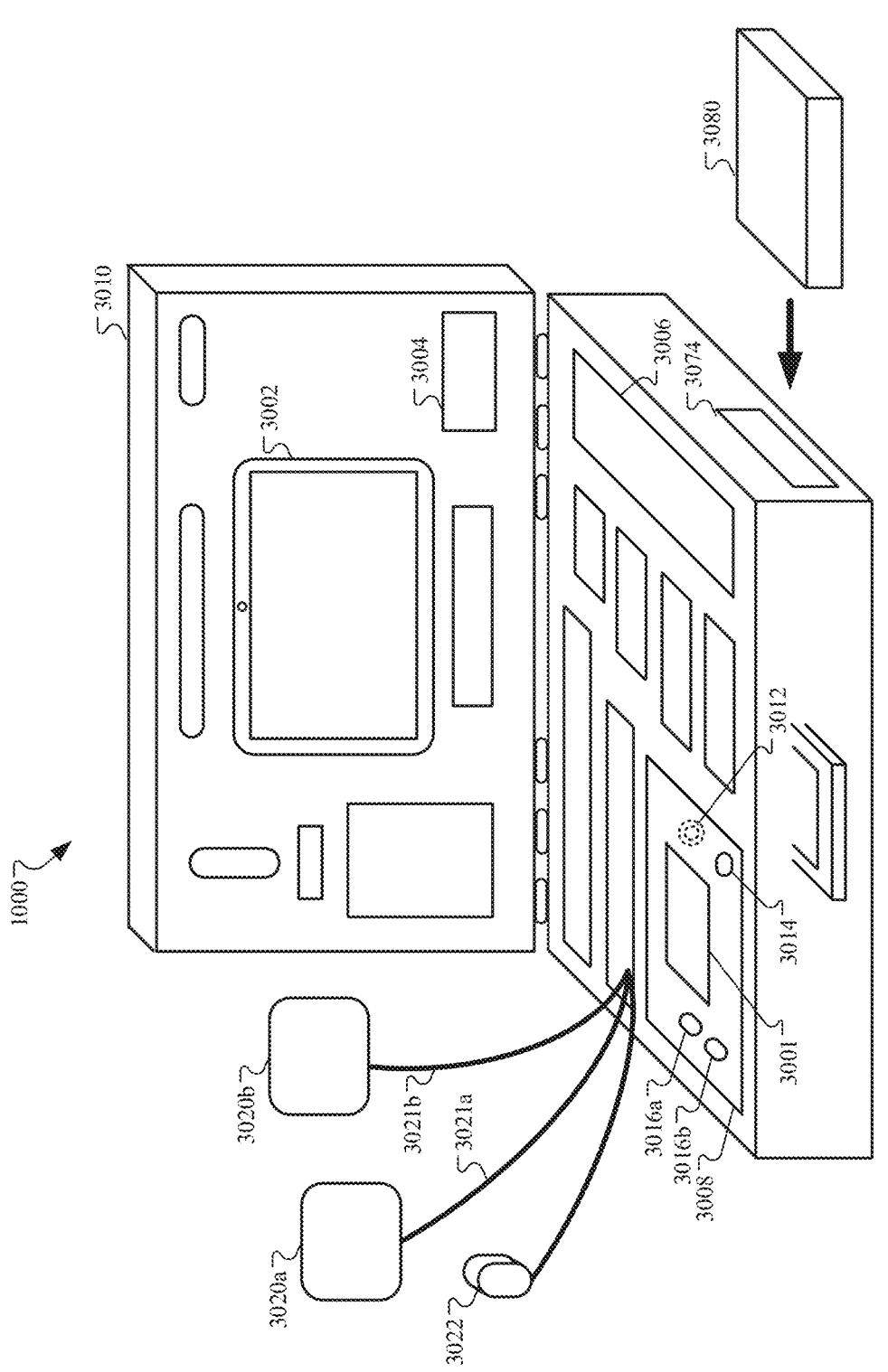
FIGS. 1A and 1B show example views of a portable medical treatment apparatus that provides both electrotherapy functionality and includes a display for guiding a user in treating non-cardiac emergencies in accordance with some embodiments.

Emergency medical personnel face the problem of not being immediately present at the scene of a medical emergency, and often do not arrive quickly enough with the most appropriate equipment for treating various types of emergency medical conditions. As a result, for at least the time period in which the proper emergency medical personnel are absent, it is left to whoever happens to be present at the emergency scene to determine the appropriate course of action for administering medical treatment. This responsibility can be intrinsically stressful, particularly for those who have little to no medical training, as well as for those who have even a basic level of training. And without appropriate guidance, such situations may result in those present at the scene to make ill-advised decisions.

The medical apparatuses described in this disclosure empower lay persons, whether trained or untrained, who may happen to be present at the scene of a medical emergency to treat different types of emergency medical conditions from which one or more victims may be suffering. For example, the portable medical treatment apparatus may contain a variety of triage-related medical instruments and supplies, and provide interactive guidance for a caregiver present at the scene to diagnose and treat a wide variety of emergency medical conditions using the items provided by the apparatus until professionally trained emergency medical personnel arrive on the scene. Example supplies that may be located inside such a case may include (but are not limited to) a tourniquet, hemostatic gauze, cardiopulmonary resuscitation (CPR) face shields, pressure dressings, CPR equipment for assisting caregivers providing manual chest compressions or ventilations, defibrillation electrodes, and the like. Examples of treatable emergency medical conditions in accordance with the present disclosure may include bleeding wounds, bone fractures, drug overdoses, respiratory distress, allergic reactions, and cardiac arrest, amongst others. The ability of a lay person to treat such a wide range of emergency medical conditions with a single, portable medical treatment apparatus (e.g., a single, human-carryable case), can decrease the likelihood of severe permanent injury or death due to treatment being applied almost immediately, or at the very least sooner than when a more trained caregiver is immediately present.

Embodiments of the present disclosure may be equipped with equipment and guidance for treating a substantially wide range of medical conditions, including emergency life-threatening cardiac/pulmonary conditions such as cardiac arrest. Accordingly, portable medical treatment apparatuses described herein may include a comprehensive all-in-one collection of medical items/equipment, along with interactive guidance for victim triage, selection and use of each of the components. What is more, certain embodiments described herein optionally provide for an arrangement of sub-components of the portable medical treatment apparatus, which allows for further modularity of the apparatus, so as to enhance overall usability for treating different medical conditions.

Take for instance a lay rescuer having little to no prior medical experience who may be presented with a medical emergency where he/she needs to find and retrieve nearby medical equipment, for example, in a medical storage cabinet or repository. It is not uncommon for such a repository to be filled with a large variety of items/equipment (e.g., tourniquets, medical blanket, public access automated external defibrillator (AED), chest seals, airway management tools, etc.) from which the lay rescuer would need to choose to bring back to the emergency scene. However, given the stress of the situation, the lay rescuer may not know exactly what items/equipment would be most appropriate to retrieve. Thus, the lay rescuer may then opt to take as many items/equipment (e.g., tourniquet, medical blanket, public access AED) that he/she can carry back to the scene using untrained judgment which may or may not be useable, or may simply leave certain items/equipment at the repository hoping to return for another trip. Yet, such time inefficiency and, at times, uncertainty runs the risk that the most appropriate item(s) are not made immediately present at the scene; such a course of action takes away valuable time from actually attending to the victim. Or, when emergency medical services arrives at the scene, rescuers typically need to bring a number of items of medical equipment to the victim, such as an AED, a patient monitor, a ventilator, medical supplies, or other items/equipment. In the rush to reach the victim, even EMS personnel may leave a vital piece of equipment back in the ambulance for later retrieval, or inadvertently so; again, potentially taking away precious time from the rescue.

Furthermore, even if rescuers, whether lay rescuers or those with prior medical training, arrive at the scene with the proper equipment, given that the diagnosis (and therefore treatment) is not yet determined, the equipment may not immediately be properly positioned. Thus, once the diagnosis and treatment is determined, the equipment (which may at times be rather heavy and cumbersome) may need to be moved, albeit awkwardly. Furthermore, a carry case that encompasses comprehensively the full range of equipment needed for a wide variety of patient conditions and treatments will likely require a significant storage volume, and as a result occupy a large footprint when placed on the ground nearby the patient. Such a large footprint adjacent the patient will impede caregiver access to the patient and potentially degrade the quality of care that a patient receives.

Figure 2A:
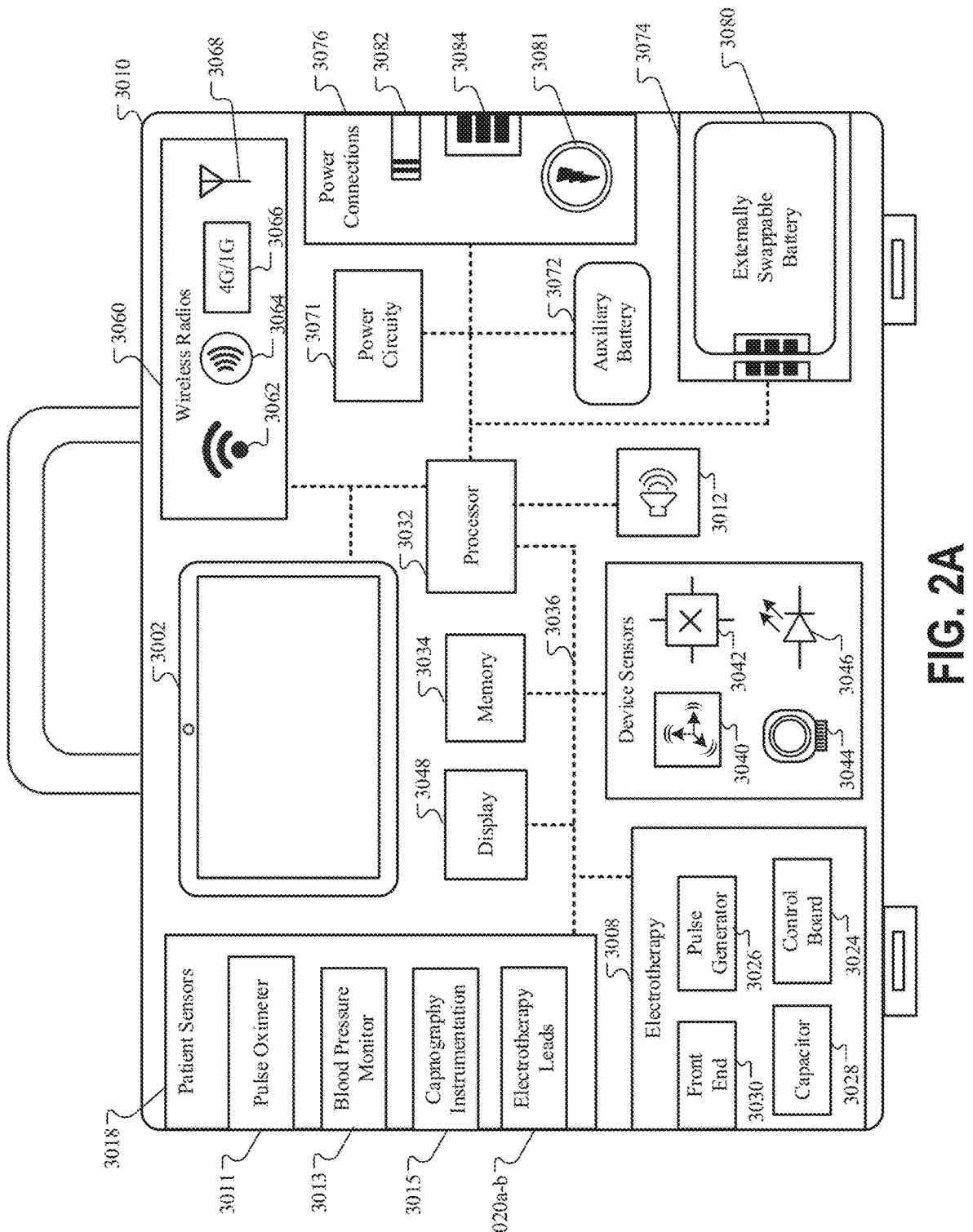
FIGS. 2A and 2B show a diagram of the portable medical treatment apparatus of FIGS. 1A and 1B that also shows some internal components.
Figure 2B:
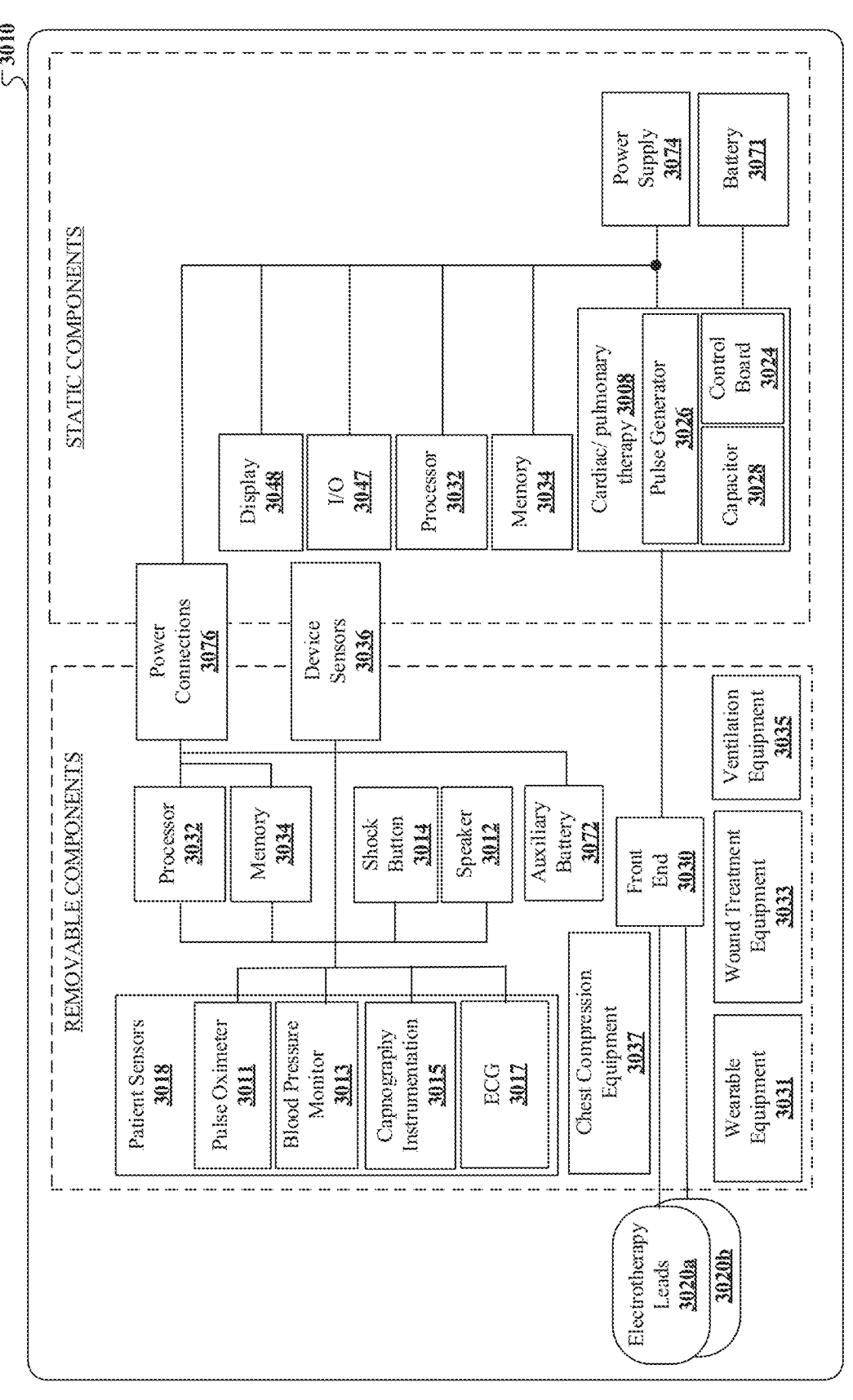

Accordingly, it may be advantageous not only for embodiments of portable medical treatment apparatuses described herein to comprehensively be able to support diagnosis and treatment for an array of acute medical conditions, modular aspects of such embodiments may further streamline care. As cardiac arrest, characterized by a sudden loss of blood flow resulting from a failure of the heart to pump effectively, is one of the most common causes of death, it is vitally important for rescuers in an emergency to have the tools necessary to carry out the necessary treatment for this condition, which includes cardiopulmonary resuscitation and defibrillation therapy. Hence, embodiments of the present disclosure include a portable medical treatment apparatus having a cardiac/pulmonary resuscitative subsystem. Such a subsystem may be optionally modular, i.e. some portion of the cardiac/pulmonary resuscitative subsystem (CPRS) is removable from the carry case, in that it can be mechanically decoupled or otherwise removed from the overall apparatus. Modular configuration of the cardiac/pulmonary subsystem allows for the larger main carry case to be placed outside the immediate vicinity of the patient's side with key components of the cardiac/pulmonary resuscitative subsystem being optimally located immediately adjacent or in contact with the patient, e.g. defibrillation electrodes or shock delivery control or other AED controls, and detachable/removable from the carry case thus providing the rescuer unimpeded physical access to the patient while at the same time conveniently locating at their side only the components needed for the task at hand. Other portions of the cardiac/pulmonary resuscitative subsystem (CPRS) may be physically and/or electrically integrated with the main carry case. The non-removable portion of the CPRS may be termed herein as the static CPRS. Some examples of static CPRS components are: larger and heavier components such as the high voltage defibrillator circuit, high voltage capacitor and larger display are more efficiently packaged in the main carry case; other components of the CPRS such as the power supply, display and battery may use the display, battery and power supply already housed in the main case thereby eliminating duplicative components. FIGS. 2A and 2B show examples of such a partition of components between the removable CPRS and the static CPRS. As discussed above and further herein, it is often the case that the overall apparatus is not initially positioned in an optimal manner to treat a cardiac/pulmonary condition, where such treatment involves electrotherapy. And, having to reposition the apparatus in its entirety may be onerous or sometimes inconvenient. For example, if the larger case of the apparatus is initially placed several feet away from the victim, in the event that a cardiac arrest is suspected, only the necessary components of the cardiac/pulmonary resuscitative subsystem may be removed from the larger storage unit and placed immediately adjacent the victim and caregiver(s) so as to optimally provide resuscitative treatment while at the same time providing the rescuer unimpeded physical access to the patient.

Figure 1B:
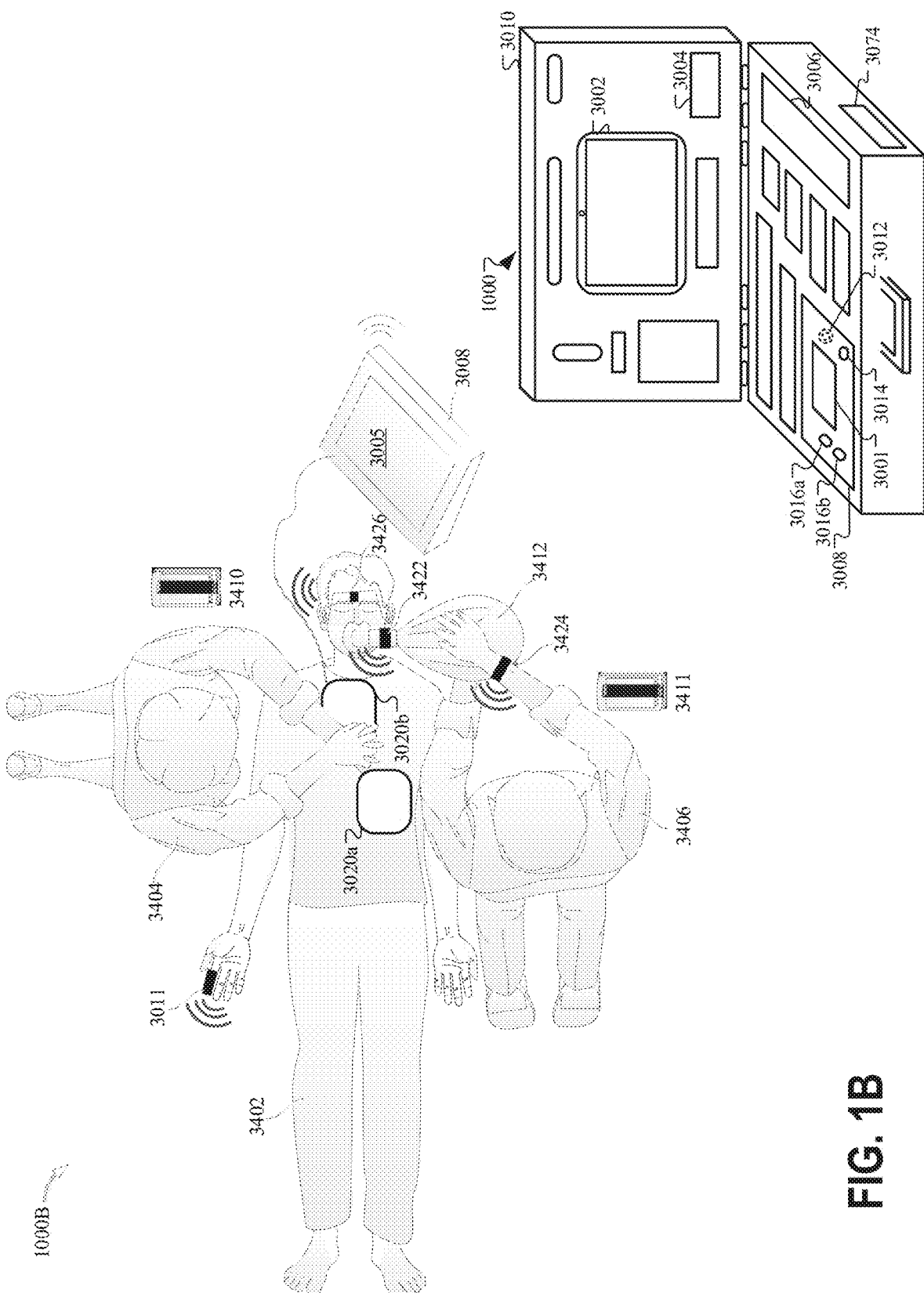

FIGS. 1A and 1B show a portable medical treatment apparatus 1000 in accordance with the present disclosure, integrating components and functionality added thereto allowing for more comprehensive treatment options than had been previously available. While FIGS. 1A and 1B show perspective views of the portable medical treatment apparatus 1000, FIG. 2 shows a complementary diagram of the portable medical treatment apparatus 1000 that shows additional components that are internal to the apparatus and therefore are not explicitly illustrated in FIGS. 3A-3C. The illustrations in FIGS. 1 and 2 are examples and are not intended to limit the portable medical treatment apparatus 1000 to a specific type of physical implementation. Indeed, while FIGS. 1 and 2 illustrate a hinged case with a rigid housing, the case of the portable medical treatment apparatus 1000 may take various different forms, such as a backpack, softer storage housing, or an unhinged housing. Stated another way, the description that is presented with respect to FIGS. 1 and 2 represents functionality that can be incorporated into various implementations presented throughout this disclosure.

Some features illustrated in FIGS. 1 and 2, for example, the portable medical treatment apparatus 1000 may include a defibrillator system 3008 that includes at least some of the components that enable caregivers using the portable medical treatment apparatus 1000 to diagnose and treat a cardiac or respiratory arrest victim as well as patients in respiratory distress, either apneic or dyspneic. Treatments may include electrotherapy (e.g., defibrillation or transthoracic pacing), or non-electric therapy including chest compressions, drug delivery and ventilation. These components that enable caregivers using the portable medical treatment apparatus 1000 to diagnose and treat a cardiac or respiratory arrest victim may be referred in some embodiments as "cardiac/pulmonary resuscitative components."

FIGS. 2A and 2B illustrate some of the user-visible cardiac/pulmonary resuscitative components, for example, a secondary display device 3005 that can display content specific to analysis of a victim's heart rhythms and administration of electrotherapy and CPR. Other user-visible cardiac/pulmonary resuscitative components in this illustrative embodiment may include: a speaker 3012; a button to initiate an electrocardiographic (ECG) analysis of the heart rhythm to determine whether a defibrillation shock is needed ("Analyze"); a shock button 3014; and indicator lights 3016a-b.

Some cardiac/pulmonary resuscitative components (e.g., static CPRS components) may be internal to the portable medical treatment apparatus 1000 and therefore may not be visible to a user. Such components (illustrated in FIGS. 2A and 2B) include a control board 3024 that electrically and operationally connects different components involved in the administration of electrotherapy or non-electric therapy. Other components may be involved in the administration of electrotherapy and may include one or more capacitors 3028 designed to receive electricity from one or more batteries and charge to high voltage energy levels, a pulse generator 3026 configured to receive the high voltage energy from the one or more capacitors and form therefrom an electrical shock with therapeutic waveform characteristics, and an electrode connection end including ECG sensor circuitry to which electrodes 3020a-b connect via electrical leads 3021a-b.

The portable medical treatment apparatus 1000 may include a sensor compartment 3018, in which a plurality of electrodes 3020a-b are stored, along with other sensors capable of monitoring health attributes of a victim, such as a pulse oximeter 3011, an electrocardiographic (ECG) sensor, a blood pressure monitor 3013 (e.g., a blood pressure cuff), ventilation air flow sensor such as the AccuVent™ flow sensor (which is able to measure rate of air flow to and from a patient's airway for providing feedback to a caregiver in administering manual ventilations according to desired tidal volume, minute volume, ventilation rate, for example) provided by ZOLL Medical Corporation, motion sensors (integrated in the chest compression equipment 3037) for measuring the quality of delivery of non-electric therapy (e.g., CPR chest compressions) such as those provided with the Real CPR Help® technology (which provides feedback for a caregiver in administering manual chest compression providers to improve the quality of compressions according to desired compression depth, compression rate, release, for example) provided by ZOLL Medical Corporation, and capnography instrumentation 3015, which monitors the concentration or partial pressure of carbon dioxide in respiratory gas.

An air flow sensor (e.g., differential pressure sensor or other sensor for measuring flow rate and volume) may be provided together with a bag-valve mask to form ventilation equipment 3035 in the case of the apparatus 1000 for providing manual ventilations to a victim. The interactive query flow may include a portion for assisting those suffering from respiratory distress where an instruction may be given to provide positive pressure breaths using a bag-valve mask. In such a situation, the apparatus 1000 may instruct the user to take the ventilation equipment 3035 (e.g., flow sensor and bag-valve mask) from the case 3010 and apply them to the victim's airway so that when the ventilation bag is squeezed, the flow sensor is able to obtain air flow information for assessing ventilation parameters such as respiratory minute volume (volume of inspiratory air per minute), ventilation tidal volume (volume of inspiratory air per breath) and/or ventilation rate (breaths per minute) provided thereto, and optionally providing feedback guidance regarding whether the ventilation parameters for manually applied ventilations are within target ranges. Embodiments of a flow sensor and the ventilation feedback provided therewith are described in U.S. Publication No. 20170266399, entitled "Flow Sensor for Ventilation," the contents of which are hereby incorporated by reference in their entirety. A chest compression sensor (e.g., accelerometer, motion sensor) may be provided in the case of the apparatus for providing manual chest compression to a victim. As discussed herein, the interactive query flow may include a portion for assisting those who are in need of circulatory assistance (e.g., cardiac arrest, heart failure, etc.) where an instruction may be given to provide chest compressions. Here, the chest compression sensor may be taken from the case and placed on the victim's sternum such that when chest compressions are given, the chest compression sensor is able to obtain information for assessing compression parameters such as compression depth, compression rate and/or release velocity of compressions, and optionally provided feedback guidance regarding whether the compression parameters for manually applied compressions are within target ranges. Embodiments of a compression sensor and the compression feedback provided therewith are described in U.S. Pat. No. 9,788,734, entitled "Defibrillator Display," the contents of which are hereby incorporated by reference in their entirety. Each of these sensors may physically and electrically connect to the case 3010 with electrical leads. For example, the electrodes 3020a-b connect to case 3010 through electrical leads 3021a-b. The electrodes 3020a-b are typically able to both provide ECG sensor functionality as well as deliver electrical therapy. In order to use a sensor for the diagnosis and/or treatment of a victim, a user may have to remove the sensor from the sensor compartment 3018 and attach a respective sensor lead to an interface terminal provided by the case 3010. For example, the electrodes 3020a-b may be stored within sterile packaging, and a user may have to remove the electrodes 3020a-b from the sterile packaging and then attach the electrical leads 3021a-b to one or more terminals provided by the electrode connection end 3030 of the electrotherapy system. In other embodiments, the sensors may be preconnected to the interface terminal whilst still remaining sealed in their packaging, for instance as implemented in the Stat-Padz electrodes provided by ZOLL Medical Corporation, Chelmsford, Mass., USA.

For instance, referring to FIG. 1B, at an emergency care scene 1000B, a caregiver 3404 can perform a treatment (e.g., CPR) on a victim or patient 3402 (the terms are used interchangeably here to indicate a person who is the subject of emergency medical treatment, or other medical treatment), such as an individual who has apparently undergone sudden cardiac arrest. The emergency care scene 1000B can be, for instance, at the scene of an accident or health emergency, in an ambulance, in an emergency room or hospital, or another type of emergency situation. The caregiver 3404 can be, for example, a civilian responder with limited or no training in lifesaving techniques; a caregiver, such as an emergency medical technician (EMT), police officer, or firefighter; or a medical professional, such as a physician or nurse. The caregiver 3404 may be acting alone or may be acting with assistance from one or more other caregivers, such as a partner EMT 3406. In the example of FIG. 1B, the caregiver 3404 is delivering chest compressions to the patient 3402 and the caregiver 3406 is delivering ventilations to the patient using a manual ventilation unit.

The caregivers 3404, 3406 can be assisted to deploy a subsystem of the portable medical treatment apparatus 1000 that can be used to treat one of a wide variety of emergency medical conditions until professionally trained emergency medical personnel arrive on the scene. For example, if a user input indicates that the patient might not be getting enough oxygen (e.g., patient is experiencing rapid breathing, shortness of breath, fast heart rate, coughing or wheezing, sweating, confusion, and/or changes in the color of the skin) the caregivers 3404, 3406 can be instructed to remove the pulse oximeter 3011 from the case 3010 and attach it to the victim to measure oxygen levels. As another example, if a user input indicates that the patient might be experiencing hypo/hypertension (e.g., patient is experiencing headaches, shortness of breath, nosebleeds, flushing, dizziness, chest pain, and/or visual changes) the caregivers 3404, 3406 can be instructed to remove the blood pressure cuff and monitor 3013 from the case 3010 to measure the blood pressure of the victim. As another example, if a user input indicates that the patient may be experiencing a cardiac event (e.g., patient is experiencing palpitations, shortness of breath, weakness, fatigue, dizziness, chest pain, and/or pain in the left arm) the caregivers 3404, 3406 can be instructed to remove the ECG pads 3017 from the case 3010 to analyze the cardiac condition of the victim. In some implementations, simultaneously with the removal of the ECG leads 3017, or at a later time (e.g., after confirmation of the ongoing cardiac event) the caregivers 3404, 3406 can be instructed to remove the electrotherapy leads 3020a, b (defibrillation electrodes) and a shock button 3014.

Additional example supplies that may be located inside the case 3010 may include (but are not limited to) wearable equipment 3031 (e.g., gloves, masks, face shields, glasses, medical uniform, etc.), wound treatment equipment 3033 (e.g., tourniquet, hemostatic gauze, sterile bandages, pressure dressings, etc.), ventilation equipment 3035 (e.g., face masks, straps, tubes, oxygen tank, pump, etc.) and chest compression equipment for assisting caregivers providing manual or automatic chest compressions. Examples of treatable emergency medical conditions in accordance with the present disclosure may include, seizure, burn, choking, impaled object, trapped limb, severed body part, child birth, confusion, bleeding wounds, bone fractures, drug overdoses, respiratory distress, allergic reactions, and cardiac arrest, amongst others. The caregiver can be guided to treat any of a preset range of emergency medical conditions using one or more submodules of the portable medical treatment apparatus 1000 (included in the case 1000), can decrease the likelihood of severe permanent injury or death due to treatment delay.

In the example illustrated in FIG. 1B, the caregivers 3404, 3406 can deploy the cardiac/pulmonary resuscitative subsystem of the portable medical treatment apparatus 1000 to treat the patient 3402. The cardiac/pulmonary resuscitative subsystem 3008 may provide electrodes 3020a-b intended to be placed on the patient's chest via one or more cables. The cardiac/pulmonary resuscitative subsystem 3008 may be equipped to provide defibrillation therapy to the patient 3402 as appropriate through the electrodes 3020a-b. In some examples, the portable medical treatment apparatus 1000 or cardiac/pulmonary resuscitative subsystem 3008 can provide instructions for one or more of the caregivers 3404 to administer CPR or other treatment to the patient 3402. As noted herein, the cardiac/pulmonary resuscitative subsystem 3008 may include a removable portion that can be decoupled from the main carry case, and a non-removable or static portion that remains with the main carry case during use.

One or more sensors (e.g., sensors 3011, 3013, 3015, and 3017) can be used to monitor the patient 3402. For instance, the sensor 3011 can monitor parameters indicative of the patient's health status, e.g., physical parameters such as the patient's heart rate, electrocardiogram (ECG), blood pressure, temperature, respiration rate, blood oxygen level, end-tidal carbon dioxide level, pulmonary function, blood glucose level, or other parameters indicative of the patient's health status. Some sensors, such as heart rate or ECG sensors, can be included in electrodes 3020a-b of the cardiac/pulmonary resuscitative subsystem 3008. One or more sensors (e.g., a sensor 3424) can monitor the treatment delivered to the patient 3402. For instance, the sensor 3424 can monitor shocks delivered to the patient 3402 by the cardiac/pulmonary resuscitative subsystem 3008; a rate, depth, or duration of compressions delivered to the patient 3402; or other parameters indicative of treatment delivered to the patient. Some sensors can monitor both parameters indicative of the patient's health status and parameters indicative of the treatment delivered to the patient. The sensors 3011, 3013, 3015, and 3017 can provide information about the patient's health status or information about the treatment delivered to the patient to the cardiac/pulmonary resuscitative subsystem 3008, one or more of the mobile devices 3410, 3411, or other computing devices at the emergency care scene 3400 or to remote computing devices.

In some implementations, one or more sensors may be stored in the sensor compartment 3018 with their respective electrical leads already operably connected to electrical circuitry of the case 3010. In some implementations, one of more of the sensors stored in the sensor compartment 3018 may wirelessly communicate with electronics within the case of the portable medical treatment apparatus 1000, and therefore may not be physically tethered to the case 3010 with a physical electrical connection. In some implementations, the sensors 3011, 3013, 3015, and 3017 may be stored in different compartments, rather than all in compartment 3018. In some implementations, the compartment in which one or more of the sensors are stored is a general compartment provided by the case as a whole, and not a sub-compartment, as illustrated in FIGS. 2A and 2B.

The portable medical treatment apparatus 1000 may include a processor 3032 that orchestrates computerized operations of the entire system (e.g., the portable medical treatment apparatus 1000). The processor 3032 can be configured to process instructions for execution using any of the submodules of the portable medical treatment apparatus 1000. The processor 3032 can be a single-threaded or a multi-threaded processor. The processor 3032 can be configured to process instructions stored in the memory 3034 or on a storage device to provide information for a caregiver using the input/output device 3047. The processor, for example, may communicate with various different components illustrated in FIGS. 2A and 2B over electrical power and communication busses 3036, receiving input signals from various sensors and devices, and sending output/instruction signals to various same and different sensors and devices. For example, the processor 3032 may interact with the touchscreen display device 3002 to indicate content for presentation by the touchscreen display device 3002 as part of the interactive query flow, and to receive caregiver input provided through user interaction with the touchscreen display device 3002. In some embodiments, there may not be a secondary display 3005, and all the information display content specific to analysis of a victim's heart rhythms and administration of electrotherapy and non-electric therapy may be presented in an integrated fashion with the query flow on the touchscreen display device 3002. In some examples the controls such as the Analyze and Shock buttons may be touchscreen controls displayed on the touchscreen display device 3002.

It may be helpful to limit the time that it takes for the touchscreen display device 3002 to initiate the interactive query flow (e.g., the time it takes before the touchscreen display device presents the "Take a Deep Breath" user interface of FIG. 73). In other words, once a user carries the portable medical treatment apparatus 1000 to a victim and opens the case, it is helpful for the interactive query flow to begin as soon as possible. To limit this "startup" time, the portable medical treatment apparatus 1000 can identify that a caregiver has begun to interact with the portable medical treatment apparatus 1000 and therefore that the portable medical treatment apparatus may be needed for an emergency.

One technique for the portable medical treatment apparatus 1000 to identify that it may be needed soon for an emergency is for the portable medical treatment apparatus 1000 to monitor whether the case 3010 has been opened. The system may determine that the case has been opened by monitoring whether a hall effect sensor 3042 (e.g., a sensor that measures magnetic field) integrated into the case of the apparatus has transmitted a signal indicative of the case 3010 opening (e.g., due to a magnetic field moving away from or closer to the hall effect sensor 3042). Another technique in which the system may be able to determine that the case has been opened includes processor 3032 analyzing whether a light sensor 3046 or an image sensor 3044 has transmitted a signal indicating that the light sensor 3046 or the image sensor 3044 light has sensed light (e.g., due to the case 3010 being opened in a lighted environment). Of course, the portable medical treatment apparatus 1000 may also or alternatively include a mechanical switch that can detect that the case 3010 has been opened.

In some examples, removal of the electrodes or other AED components from the case may cause, via the techniques described herein, either the portable medical treatment apparatus 1000 to power up as a complete system, or alternatively, the cardiac/pulmonary resuscitative subsystem may power up separately and more rapidly than the rest of the system, so as to allow for delivery of electrotherapy or non-electric therapy within less than e.g. 30, 20, or 10 seconds. The electrode package may have a magnet embedded in a sleeve, storage package or cassette housing by which its removal is detected via a Hall effect sensor located in its storage area. Alternatively, detection may be achieved via an optical photo-interrupter replacing the magnet/Hall effect combination.

Yet another mechanism in which portable medical treatment apparatus 1000 may be configured to identify that the portable medical treatment apparatus 1000 may be soon needed for an emergency is a determination by the portable medical treatment apparatus 1000 that the case 3010 has been physically moved, which may indicate that someone is carrying the case to a scene of an emergency. As such, the system may monitor signals received from an accelerometer 3040, a gyroscope (not shown), or another type of sensor, to determine whether the case is being moved. The movement may need to exceed a threshold level (e.g., a threshold amount of force and/or a threshold duration of movement), in order for the portable medical treatment apparatus 1000 to determine that it is likely to be soon needed for an emergency. In another example the motion sensing may be located in the electrodes or other AED component.

One possible reason that the portable medical treatment apparatus 1000 may monitor whether the case has been opened or moved is because the portable medical treatment apparatus 1000 may need to "wake" or "boot up" the interactive query process. As an illustration, in those implementations in which the touchscreen display device 3002 is a tablet computing device 3002, leaving that tablet computing device continuously running a start screen of the interactive query flow while the portable medical treatment apparatus 1000 is not being used will cause the tablet computing device 3002 to exhaust battery power in a relatively short period of time (at least in those implementations in which the portable medical treatment apparatus 1000 is not connected to a continuous supply of external wall power). Indeed, limiting the power that is consumed by the portable medical treatment apparatus 1000 when that medical apparatus is not in use can be particularly helpful, both to make sure that the portable medical treatment apparatus 1000 has battery power when needed, and to limit the frequency with which battery power must be replenished.

In one example, the power consumption when the portable medical treatment apparatus 1000 is not being used may be limited by configuring the tablet computing device 3002 to operate in a low-power "sleep" state, and wake the tablet computing device 3002 upon the portable medical treatment apparatus 1000 identifying that one of the above-described triggers has occurred (e.g., determining that the case 3010 has opened or has been moved). Another solution for limiting power consumption is for tablet computing device 3002 to remain "off" when the portable medical treatment apparatus 1000 is not being used, and to have electronics of the portable medical treatment apparatus 1000 monitor for occurrence of one of the above-described triggers (e.g., the case 3010 being opened or moved), or another suitable trigger for determining that the interactive query flow should be immediately ready. Upon detecting such a trigger, the apparatus 1000 may power on the tablet computing device 3002.

Still, it may be helpful to activate the touchscreen display device or tablet computing device 3002 faster than the amount of time that it takes to turn the tablet from an "off" state to an "on" state. Moreover, even if the tablet computing device 3002 is placed in a "sleep" state, the tablet computing device 3002 may consume more power than desired while asleep. As such, rather than using an off-the-shelf tablet computing device in conjunction with its off-the-shelf operating system, the tablet computing device 3002 may operate an open source operating system (e.g., LINUX or ANDROID) or a real-time operating system that launches a dedicated application program that provides the interactive query flow, without an extensive boot process. Configuring portable medical treatment apparatus 1000 to execute a single program or a limited set or programs rather than, for example, launching computer libraries for actions that are unnecessary to the interactive query flow, can reduce the time that it takes the tablet computing device 3002 to turn on from an "off" or "sleep" mode.

In some implementations, the portable medical treatment apparatus 1000 does not include a processor 3032 in addition to a tablet computing device 3002 that has its own integrated processor. Rather, the processor of the tablet computing device 3002 may serve as an only processor of—and may communicate with—components of the portable medical treatment apparatus 1000 through system busses 3036. In some implementations, device 3002 is not a full-featured tablet computing device 3002 with auxiliary functionalities common to full-featured tablet devices, and rather is a dedicated touchscreen display device 3002 that is controlled by the processor 3032. Using such a dedicated touchscreen display device 3002, rather than a tablet, computing device 3002 may limit power consumption and minimize the amount of time between a caregiver opening the case 3010 and content appearing on the touchscreen display device 3002. Moreover, use of a dedicated touchscreen display device 3002 may allow apparatus designers to further limit energy usage of the portable medical treatment apparatus 1000 when in its inactive, stored state. For example, the processor 3032 may be able to function in a low-power state that occasionally polls data from one or more of the device sensors 3011, 3013, 3015, and 3017, in order to determine whether the device is likely to be used in an emergency, and therefore should transition to a more full-featured mode in which an initial user interface of the interactive query flow presented by touchscreen display device 3002.

Other components of portable medical treatment apparatus 1000 that have not yet been described include auxiliary display device 3048, input/output device 3047, and auxiliary speaker 3050 (e.g., in addition to a speaker in tablet computing device 3002). The auxiliary display device 3048 may present content that is in addition to and/or different from the content that is presented by touchscreen display device 3002. For example, the auxiliary display device 3048 may present content that is specific to diagnosis and treatment of cardiac or respiratory arrest. The use of the auxiliary display device 3048 may be particularly helpful in implementations in which some of the components of the portable medical treatment apparatus 1000 that provide electrotherapy are contained within a removable subsystem (implementations with removable subsystems providing electrotherapy functionality are described in further detail with reference to FIGS. 6-10). The input/output device 3047 provides input/output operations for the portable medical treatment apparatus 1000. In one implementation, the input/output device 3047 includes a keyboard and/or pointing device. The input/output device 3047 can be configured to communicate with the display device 3048 for displaying graphical user interfaces and the speaker 3012 to generate video and audio instructions for the caregivers.

The portable medical treatment apparatus 1000 may also include one or more wireless radios 3060 that enable the portable medical treatment apparatus 1000 to wirelessly communicate with various different systems. Example wireless radios 3060 include a Wi-Fi radio 3062, a near-field communication radio 3064, a 4G and/or 5G radio 3066 for communication with a distributed network of cellular towers, and a Bluetooth radio 3068. Longer range radios (e.g., the Wi-Fi radio 3062 and the 4G/5G radios 3066) may be used by the apparatus 1000 to communicate with remote systems that allow administrators to monitor inventory or status of the portable medical treatment apparatus 1000, and/or allow the portable medical treatment apparatus 1000 to communicate with a remote system to indicate that the portable medical treatment apparatus is being used in an emergency. For example, the portable medical treatment apparatus 1000 may be configured to call 911 or other appropriate emergency services and indicate that an emergency is happening at a specific location identified by a GPS system of the portable medical treatment apparatus 1000. Shorter range radios, such as Bluetooth radio 3068, may be used by the case 3010 to wirelessly communicate with other components of the portable medical treatment apparatus 1000 that may not be physically connected to the case 3010 (e.g., a wireless pulse oximeter 3011). The near-field communication radio 3064 can be used by the portable medical treatment apparatus 1000 to identify that the case 3010 has been placed near a particular location (e.g., a docking station or another portable medical treatment apparatus). In various embodiments, the interactive query flow may continuously provide throughout each inquiry page an input for the medical treatment apparatus to call emergency services, so that when the caregiver actuates the input to call emergency services, the connection may then be made. Or, in some embodiments, the medical treatment apparatus may automatically call emergency services, if not done so already, based upon caregiver answers to the interactive query flow. For example, if the caregiver inputs to the apparatus that the victim is unconscious and without a pulse, then the medical treatment apparatus may automatically prompt the victim to input whether emergency services has been called, along with proceeding immediately to the resuscitation portion of the query flow. If answered in the negative that emergency services has not been called, then the medical treatment apparatus may automatically do so or at least instruct the caregiver to do so, in a manner that does not detract from providing resuscitative treatment to the victim.

The portable nature of the medical treatment apparatus 1000 is facilitated by one or more batteries that are able to power the electronics of the portable medical treatment apparatus 1000, for example, an auxiliary battery 3072 and an externally-swappable battery 3080. The batteries may lose charge over time, either due to parasitic drain or due to use for occasional operations, such as a wireless communications with remote system that monitors inventory of the apparatus 1000. The portable medical treatment apparatus 1000 includes various different components to resupply power to the batteries. In some examples, one or more of the batteries may be charged by an external supply of power. For example, the portable medical treatment apparatus 1000 may be stored in a cabinet or docking system that is connected to an external supply of power, and that cabinet or docking system may electrically communicate with the portable medical treatment apparatus 1000 to provide power through an input power terminal 3082, input power contact pads 3084 (e.g., pads that are contacted by pogo pins of the cabinet or docking system), or through a wireless power receiver 3085. The portable medical treatment apparatus 1000 may include power circuitry 3071 that controls charging of the auxiliary battery 3072 and/or the externally swappable battery 3080, and the distribution of power along the electrical busses 3036 of the portable medical treatment apparatus 1000.

In some situations, the portable medical treatment apparatus 1000 may be stored in a location that does not have a source of external power. As such, an individual may need to occasionally service the portable medical treatment apparatus 1000 to supply it with power. Opening the case 3010 to change one or more batteries, however, may be burdensome, particularly when several or dozens of such portable medical treatment apparatus 1000 are distributed throughout a facility. As such, the portable medical treatment apparatus 1000 may be designed so that the externally swappable battery 3080 may be accessed and replaced while the case 3010 remains closed. For example, the case may remain closed with latches keeping a top portion and bottom portion of the case together (or a zipper holding sides of the case together in backpack versions, for example), while a user accesses external battery bay 3074 to remove battery 3080 and replace battery 3080 with another such battery. An externally swappable battery 3080 can shorten the time required to service portable medical treatment apparatus 1000.

The portable medical treatment apparatus 1000 may include an interactive instructional device or component such as a tablet computing device or interactive system with printed circuit board built in to the portable apparatus that is configured to execute an interactive instructional computer application (also referred to in some examples herein as an "app," "MOBILIZE app," "application," "MOBILIZE application," or other reference). This computer application may be configured to guide a caregiver, who may range from an untrained layperson to a trained professional caregiver, through a triage process and may therefore empower the caregiver to treat one or more victims until medical help with more professional training arrives, as described with reference to FIGS. 3-7.

In reference to various embodiments in which different types of responders (trained or untrained) may use the apparatus, the level of detail of the instructions may vary accordingly. If the caregiver is a medically untrained layperson, then instructions having a greater level of detail may be provided for some treatments as compared to if the caregiver is someone who has an advanced or even a basic level of medical training who might not need basic instructions. In some situations, if the caregiver is someone who has a more advanced level of medical training (advanced life support training), then the apparatus may provide additional information at least in some portions of the interactive query flow that may be useful in treating the victim, such as physiological information/data of the victim. In some embodiments, the interactive query flow may include a question at the beginning that inquires how well trained the caregiver is in medical diagnosis and treatment, for example, whether the caregiver has any formal medical training, a basic life support (BLS) level of medical training, or an advanced life support (ALS) level of medical training. Depending on the selection of the caregiver, the query flow may vary accordingly. In some cases, the query flow may default to the series of inquiries and information relevant to what would be provided to an untrained caregiver (e.g., more detailed/graphic instructions with information that is understandable to the lay user), yet with an optional selection to use a query flow appropriate for a more trained caregiver. For example, the query flow may begin under the assumption that the caregiver lacks medical training and there may be a selection (e.g., touch input button located toward a peripheral part of the screen) to indicate that the caregiver has a requisite amount of medical training (e.g., BLS training or ALS training). Once the caregiver selects that he/she has medical training, then the query flow may be adjusted accordingly to suit the more trained caregiver and the caregiver instructions can be provided in an integrated and unified display, as illustrated in FIGS. 6 and 7.

As a more specific example for how the query flow may vary depending on the type of caregiver, when instructing the responder to apply a tourniquet, the query flow for an untrained caregiver may provide detailed instructions for where to access the tourniquet (as illustrated in FIG. 78), what the tourniquet looks like (as illustrated in FIG. 79) and how to apply the tourniquet (as graphically shown in FIG. 81). However, the query flow for a caregiver with more training (e.g., basic or advanced medical training) may be more simplified and streamlined, for example, such a query flow may present only instructions for where to access the tourniquet (as illustrated in FIG. 78) and a prompt to use the tourniquet (as illustrated in FIG. 80), without the more detailed graphic instructions which may otherwise distract or delay treatment.

Or, as another example of how the query flow may vary depending on the type of caregiver, when instructing the responder to apply CPR chest compressions and/or to use the (removable) cardiac/pulmonary resuscitative subsystem, the query flow for an untrained caregiver may provide graphics as to how to apply compressions, along with a metronome for compressing the chest at a desired rate (e.g., 100-120 compressions per minute). Or, with respect to use of the cardiac/pulmonary resuscitative subsystem, the query flow may provide graphical instructions for how to attach pads, start CPR, remove hands during ECG analysis, and pressing a shock button for administering defibrillation therapy, as illustrated in FIGS. 5-9.

Item Removal from the Portable Medical Treatment Apparatus

Figure 3A:
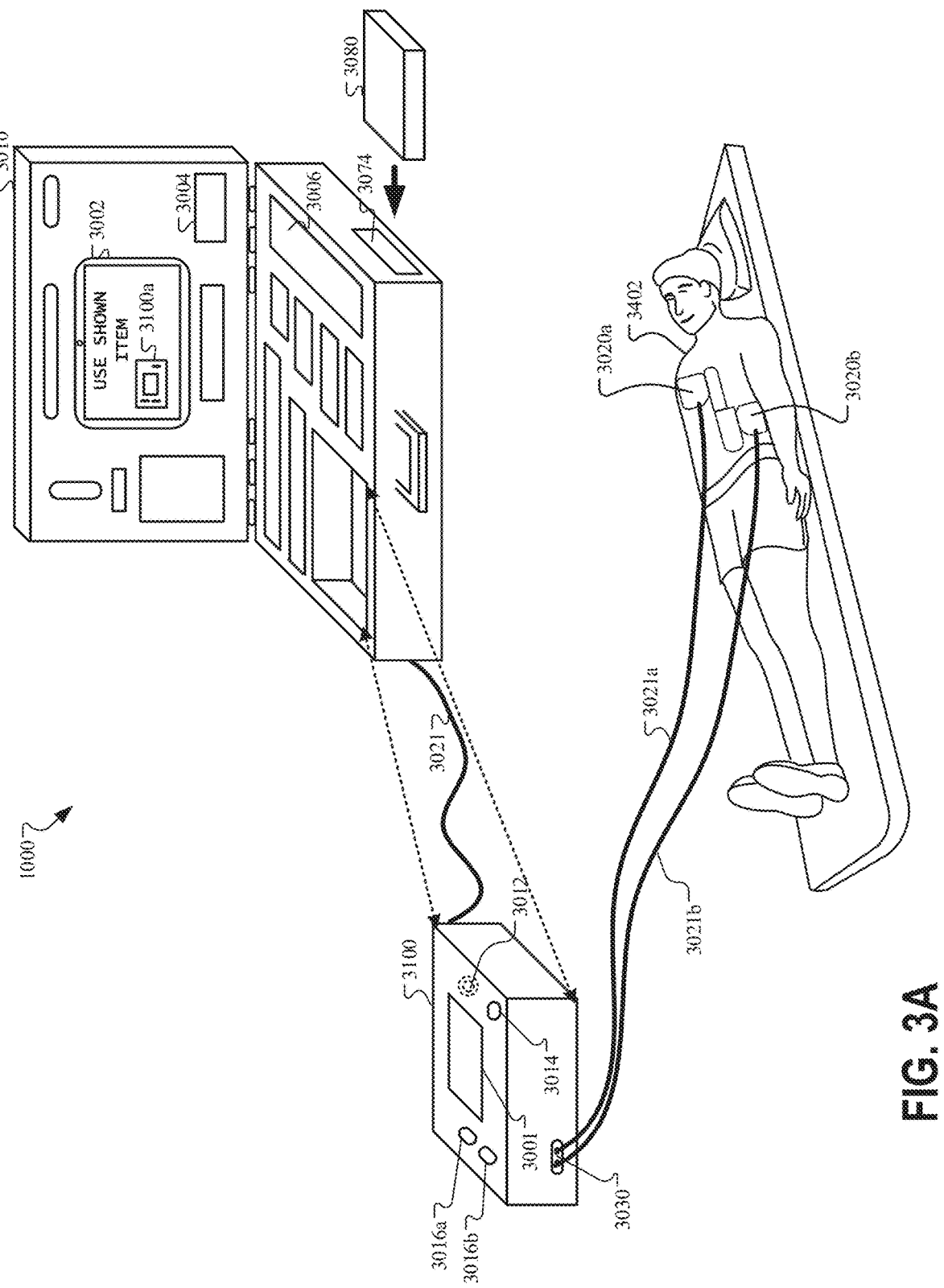
FIGS. 3A-3C show various implementations of the portable medical treatment apparatus of FIG. 1A that include removable modular resuscitative subsystems for administering electrotherapy.
Figure 3B:
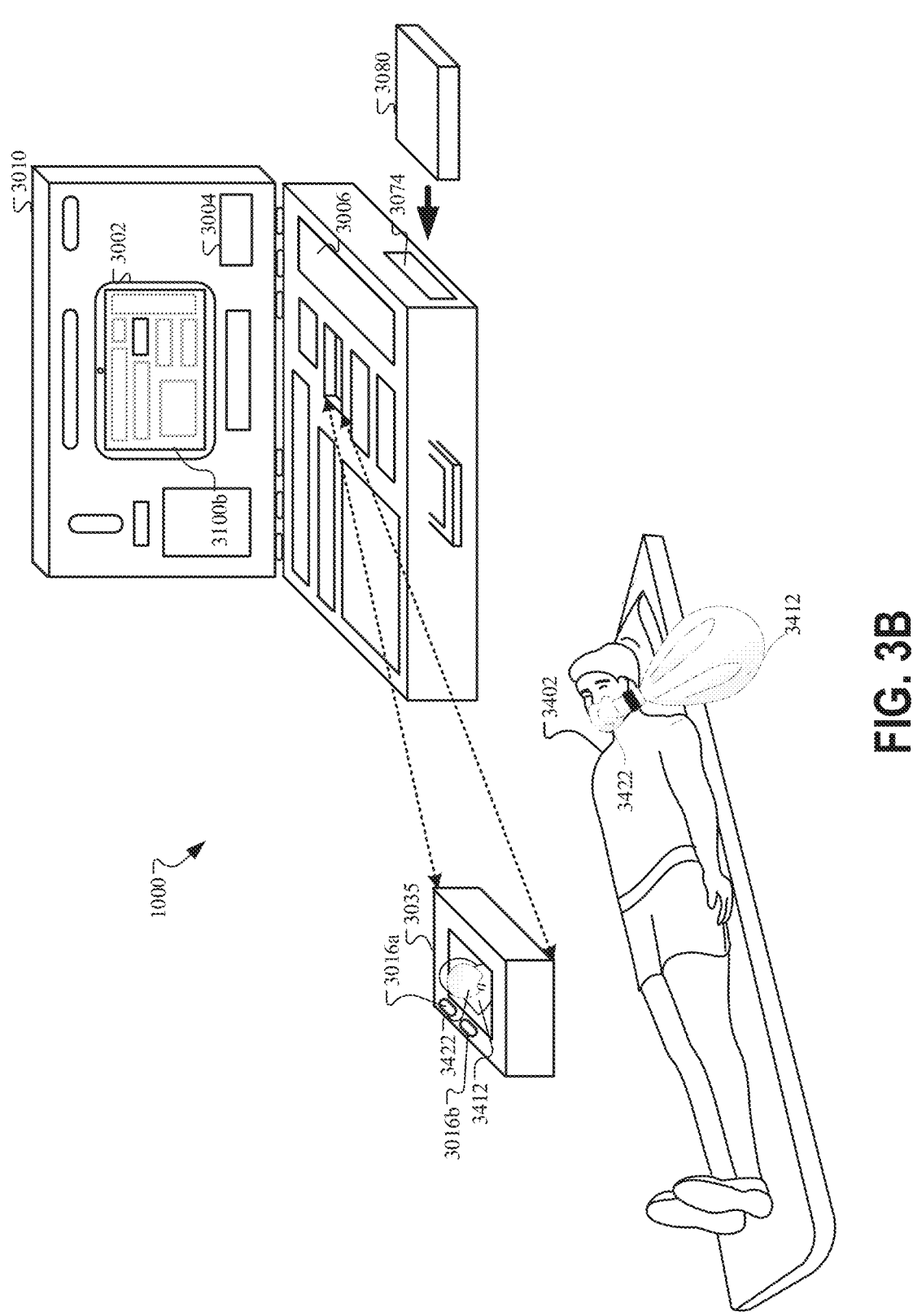
Figure 3C:
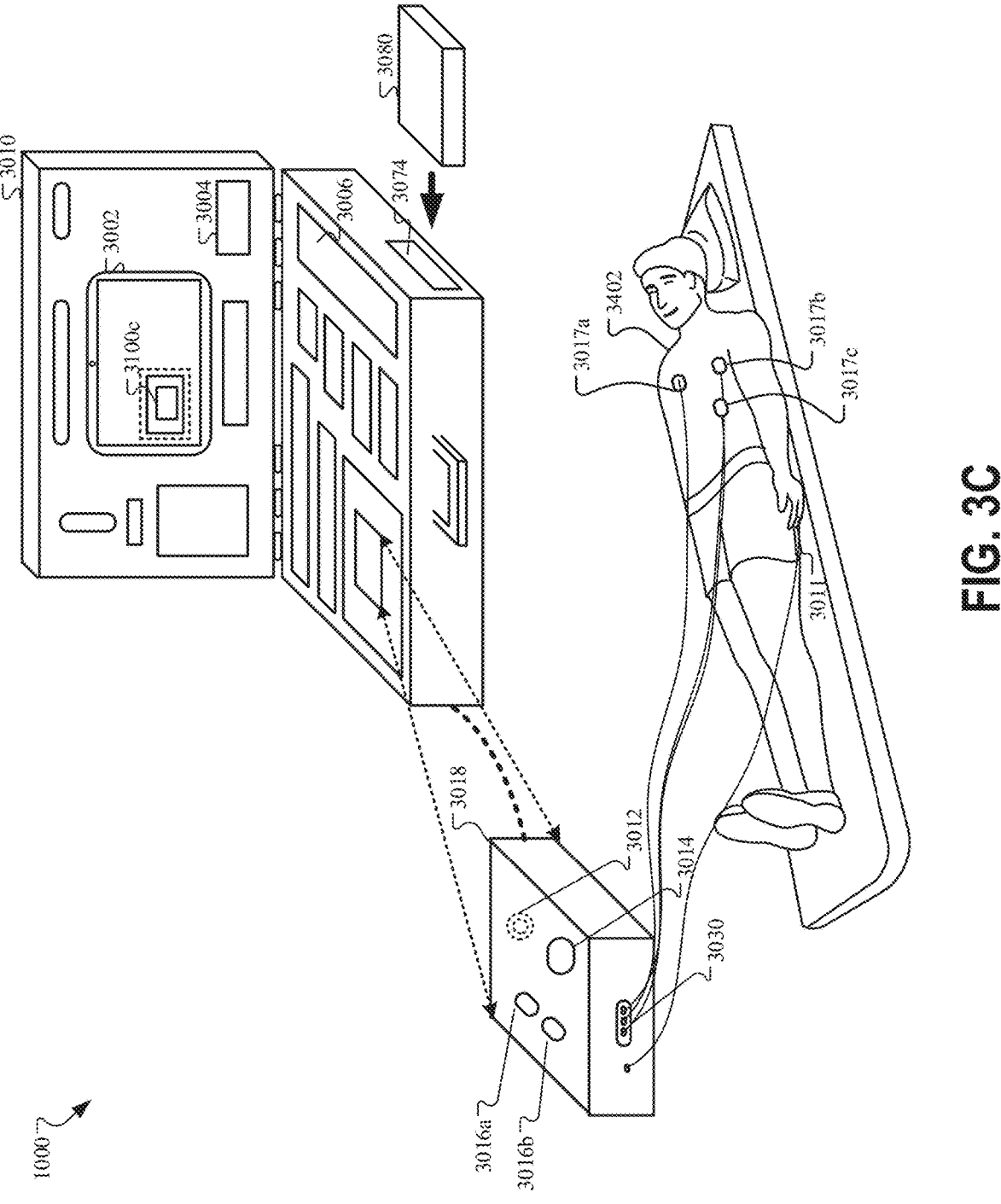

FIGS. 3A-C show various different implementations, in which the portable medical treatment apparatus 1000 includes a removable cardiac/pulmonary resuscitative subsystem 3100 that may be used in combination with a static cardiac/pulmonary resuscitative subsystem in the administration of electrotherapy treatment. As previously described, the portable medical treatment apparatus 1000 may be used to treat both non-cardiac emergencies (e.g., allergic reactions and seizures), as well as cardiac emergencies. Caregivers may not be aware of which emergency from which a victim is suffering. Indeed a purpose of the interactive query flow described throughout this disclosure is to enable a caregiver to assess from which type of emergency a victim may be suffering. As such, a caregiver may not initially place the case 3010 (which may be rather heavy to move and adjustment its position multiple times) close enough to the victim to both interact with the patient to provide non-electric therapy, listen for breath, measure pulse, apply electrodes, etc.; and easily view and/or control the user interface of the portable medical treatment apparatus 1000 and/or access some features of the case 3010 from where it is positioned. Due to the limited space in the vicinity of the patient during ongoing resuscitation efforts and the size of the case 3010 that may contain a variety of medical supplies, it may be advantageous to, for instance, place the case 3010 several feet away from the patient while having the removable portion of the cardiac/pulmonary resuscitative subsystem located immediately adjacent to the patient and caregiver or other personnel resuscitating the patient. Therefore, it can be helpful for some functionality related to diagnosis and treatment of cardiac and respiratory arrest and/or other controls to be located within a removable CPRS 3100 that the caregiver is able to remove from the case 3010 and place closer to the victim during treatment. And as further discussed herein, the removable CPRS may be in communication with a static CPRS located in the case of the apparatus.

There are many different manners in which the removable CPRS 3100 and static CPRS may be implemented. In particular, the electrotherapy-associated components included in the removable cardiac/pulmonary resuscitative subsystem 3100 rather than in the case 3010 may vary among different implementations. Multiple examples of such implementations are illustrated in FIGS. 3A-3C.

In the example of FIG. 3A, a light and compact version of the removable CPRS 3100 can be removed from the case 3010 and remain in a wired connection with the case 1000 through the cable 3021. The cable 3021 can be configured to transmit high voltage signals and/or low voltage signals. The CPRS 3100 includes electrodes 3020a,b and cable 3021a,b, along with the electrode storage. Electrode storage may be in the form of a cassette, envelope, pocket, etc. The storage may be sealed to prevent the electrodes from drying out. The cable 3021a,b houses the high voltage wires that deliver electrotherapy. In another example, a removable CPRS that contains the necessary controls for operating the AED functions is included along with the electrodes and electrode storage. The AED controls in this example may include an AED power-on button, an Analyze button, a Shock button, or any combination thereof. The cable 3021a,b additionally will house the low voltage signals necessary for the control module to communicate with the control board housed in the case 3010 along with power to the removable CPRS. The low voltage signals and power may take the form of a 4-wire USB or other serial communication interface. The removable CPRS may include a processor and memory for communication and processing of the sensor data such as ECG and motion. In another example, a chest compression motion sensor may also be part of the removable CPRS. The motion sensor may be part of the electrodes such as with the CPR Stat-Padz provided by ZOLL Medical Corporation, or be stand-alone from the electrodes. The AED controls may be integrated with the electrodes or motion sensor housing, or be stand-alone. The removable CPRS may also include either one or both a secondary display 3001 that can provide instructions to the caregiver or status lights 3016a-b.

Such an embodiment may illustrate a relatively full-featured implementation of the removable CPRS 3100. In some implementations, the CPRS 3100 can include a wireless or wired 3021 communicative connection with the static CPRS located in the main case 3010 that enables communication between the removable CPRS 3100 and the static CPRS of the main case 3010 both when inserted in or removed from the main case 3010. This implementation of the removable CPRS 3100 includes an electrode connection end 3030 to which electrodes connect, a shock button 3014 that enables a caregiver to administer a shock once a shockable rhythm is detected and all individuals are clear of and no longer contacting the victim, a secondary display 3001 (e.g., visual display, touchscreen) that can provide instructions to the caregiver, status lights 3016a-b and/or other user interactive features to indicate a status of the electrotherapy (e.g., "ready to shock" or "cardiac rhythm effective"), and a high-voltage board that includes high-voltage electrical components for delivering a high-voltage shock to the victim (e.g., one or more capacitors 3028 and the pulse generator 3026).

In this implementation, relatively few electrotherapy components are located in the static CPRS located back in the overall apparatus 3010, for example, the control board that analyzes the cardiac rhythms of the victim and determines whether to administer a shock to the victim, and the electrode storage 3112 may be located back in the case 3010 (i.e., the static CPRS). In this implementation, a caregiver would have to remove the electrodes from the main case 3010 and attach those electrodes to the electrode connection end 3030 of the removable CPRS 3100, although an alternative implementation could certainly include the electrode storage 3112 as part of the removable CPRS 3100. Another alternative implementation would involve the control board portion that analyzes cardiac rhythms for whether a shockable rhythm is present being in the removable CPRS 3100.

While for such an implementation, a majority of the AED components may be part of the removable CPRS 3100, the static CPRS in the case 3010 may have communications circuitry where the removable CPRS 3100 provides an update as to its status and/or enables the interface of the main case 3010 and the interface of the removable CPRS 3100 to operate in concert. For instance, the circuitry that controls the interactive query flow may be located back in the main case 3010, which may be preferable if the case 3010 stores the rest or at least most of the medical inventory for the caregiver to use. Accordingly, the ECG analysis circuitry (e.g., control board) of the removable CPRS 3100 may send signals, report in, or otherwise communicate with the primary circuitry located in the case 3010 so that the interactive query flow is able to incorporate the findings of the control board as further input for helping to assist the user in the medical triage effort. As an example, if the interactive query flow comes to a point where it is recommended to take out the removable CPRS for implementing a cardiac arrest protocol, then both interfaces (interface from the main case and interface from the removable CPRS) may effectively "mirror" one another such that input and associated instructions may be provided at either terminal. It can be appreciated that such a "mirror" does not require the interfaces to be exactly the same in display, although the relevant medical/instructional information provided would be substantially the same or similar in nature. Or, the interface of the removable CPRS and the interface of the main case may inform a user at either terminal that a cardiac arrest protocol has been entered and instruct the user to use the interface of the removable CPRS, so that there is no discrepancy or question as to the guidance provided by the removable CPRS or the overall interactive query flow.

There are various different manners in which electrotherapy, ventilation or CPR-associated components may be distributed among the removable CPRS (CPRS) 3100 and the static CPRS that is permanently housed in the case 3010, some of which are illustrated in FIGS. 3A-C. For example, in various implementations (e.g., FIGS. 3B-C) the high-voltage board may be located in the static CPRS of the case 3010 rather than in the removable CPRS 3100. A reason for locating the high-voltage board in the case 3010 is to limit the size of the removable CPRS 3100, due to the potentially large size of the capacitors and the associated circuitry. In some implementations, the electrode storage 3112 may be located in the removable CPRS 3100 (e.g., as illustrated in implementations FIG. 3C). Once a caregiver separates the removable CPRS 3100 from the static CPRS in the case 3010, the caregiver does not need to return to the case 3010 to retrieve the electrodes.

In some implementations, the removable CPRS 3100 includes a dedicated shock button 3014 (e.g., as in implementations FIGS. 3A-C) and/or an Analyze button. Locating a dedicated shock button 3014 and/or analyze button at the removable CPRS 3100 may be helpful in implementations in which defibrillation is semi-automatic and requires the caregiver to press a button to administer shock rather than the portable medical treatment apparatus 1000 delivering a shock on its own initiative. In other implementations, the shock button 3014 may be located at the case 3010 or implemented with a touchscreen control of a touchscreen display at either the removable CPRS 3100 or the case 3010.

In some implementations, the removable CPRS 3100 includes a limited set of electrotherapy-associated features. For example, the removable CPRS 3100 may include only an electrode connection end 3030 to which electrodes can attach or come pre-attached, and either an electrode storage 3112 or the loose electrodes themselves (e.g., as in implementation FIG. 3C). Similarly, in some implementations, the removable CPRS may have a cable providing power and communication from the case or be battery powered and have wireless communication with the processor in the case via Bluetooth or WiFi.

Referring to another example of a removable item from the case 3010, ventilation equipment 3035 for providing manual ventilation is shown in FIG. 3B. In the illustrated example, the removable ventilation equipment 3035 includes a face mask 3422 and a ventilation bag 3412. The ventilation equipment can include status lights 3016a-b, and/or may include other relevant user interactive display features for assisting the user in carrying out manual ventilation according to the interactive query flow. Accordingly, the manual ventilation portion of the interactive query flow may instruct the caregiver to take the removable ventilation equipment 3035 out from the case 3010, and attach the face mask 3422 to the victim using the straps, and to apply a bag-valve mask to the mask, so that manual ventilations can be administered. In some implementations, the facemask includes an airflow sensor to measure the effectiveness of the ventilations. For instance, the manual ventilation portion of the interactive query flow may provide feedback for the caregiver to administer manual ventilations according to desired targets (e.g., tidal volume, minute volume, ventilation rate). In some implementations, other patient sensors (e.g., a pulse oximeter 3011, a blood pressure monitor 3013, capnography instrumentation, or ECG electrodes 3017) can also be used. As illustrated in FIG. 2B, the patient sensors can be separated from the ventilation equipment 3035 and the 3010 can be configured for simultaneous use of multiple submodules.

In another embodiment shown in FIG. 3C, for a portion of the CPRS 3100 (the patient sensor submodule 3018) can be extracted from the case 3010 and the other components of the CPRS 3100 may remain in the case 3010 of the main apparatus 1000. Such an embodiment allows for the removable patient sensor submodule 3018 of the CPRS 3100 to be smaller and easier to handle. Accordingly, by effectively integrating only the sensor (physiological data acquisition) features of the CPRS 3100, the removable CPRS 3100 may be substantially less bulky than that of other embodiments. However, the caregiver may need to retrieve the sensors (e.g., pulse oximeter 3011 and/or ECG electrodes 3017a,b,c) from the case 3010 of the apparatus, plug them into the corresponding connection port (or a suitable connection to the high-voltage circuitry where the case is located), and adhere them to the victim. In some implementations the removable patient sensor submodule 3018 can be connected to the case 3010 with a wire or a wireless connection. In some implementations, the removable patient sensor submodule 3018 includes an auxiliary battery 3072 that powers the data detection systems integrated in the removable patient sensor submodule 3018.

Treatment-associated components may be split between the removable CPRS 3100 and the case 3010 in various different manners. The removable CPRS 3100 may be tethered by a data and/or high-voltage line to the case 3010, although removable CPRS 3100 may also include a wireless module that wirelessly communicates with the case 3010. In such wireless implementations, one or more capacitors 3028, charging circuitry and the pulse generator 3026 would be located in the removable CPRS 3100 while the control board would remain in the case 3010 and the control board would communicate with a secondary control board in the removable CPRS 3100 which would include one or more batteries to charge the capacitors 3028 where multiple shocks are required so that the capacitor(s) may be repeatedly charged. In various embodiments, when the high-voltage circuitry is located in the case 3010 of the apparatus, the removable CPRS 3100 may have circuitry that controls charging and/or discharge of the capacitor(s), via a control cable or wirelessly. That is, for such embodiments, a high-voltage cable may extend from the capacitor(s) located in the static CPRS of the case 3010 of the apparatus to the removable CPRS 3100 for the defibrillation electrodes to administer the electrotherapy to the victim.

Options to Operate the Portable Medical Treatment Apparatus

FIGS. 4A-D show diagrams that illustrate various different options A-D in which embodiments of the portable medical treatment apparatus 1000 disclosed herein may navigate through an interactive query flow. There are various different ways in which a single device (e.g., a portable medical treatment apparatus 1000) can integrate electrotherapy-related guidance and non-cardiac-related guidance into a single query flow. FIGS. 4A-D illustrate four such options for integrating both types of therapy/guidance into a single query flow. This discussion may also refer to the electrotherapy-related portion of the query flow as a "cardiac/pulmonary resuscitative treatment" portion of the query flow, and the non-cardiac-related guidance as an "other medical treatment" portion of the query flow.

Figure 4A:
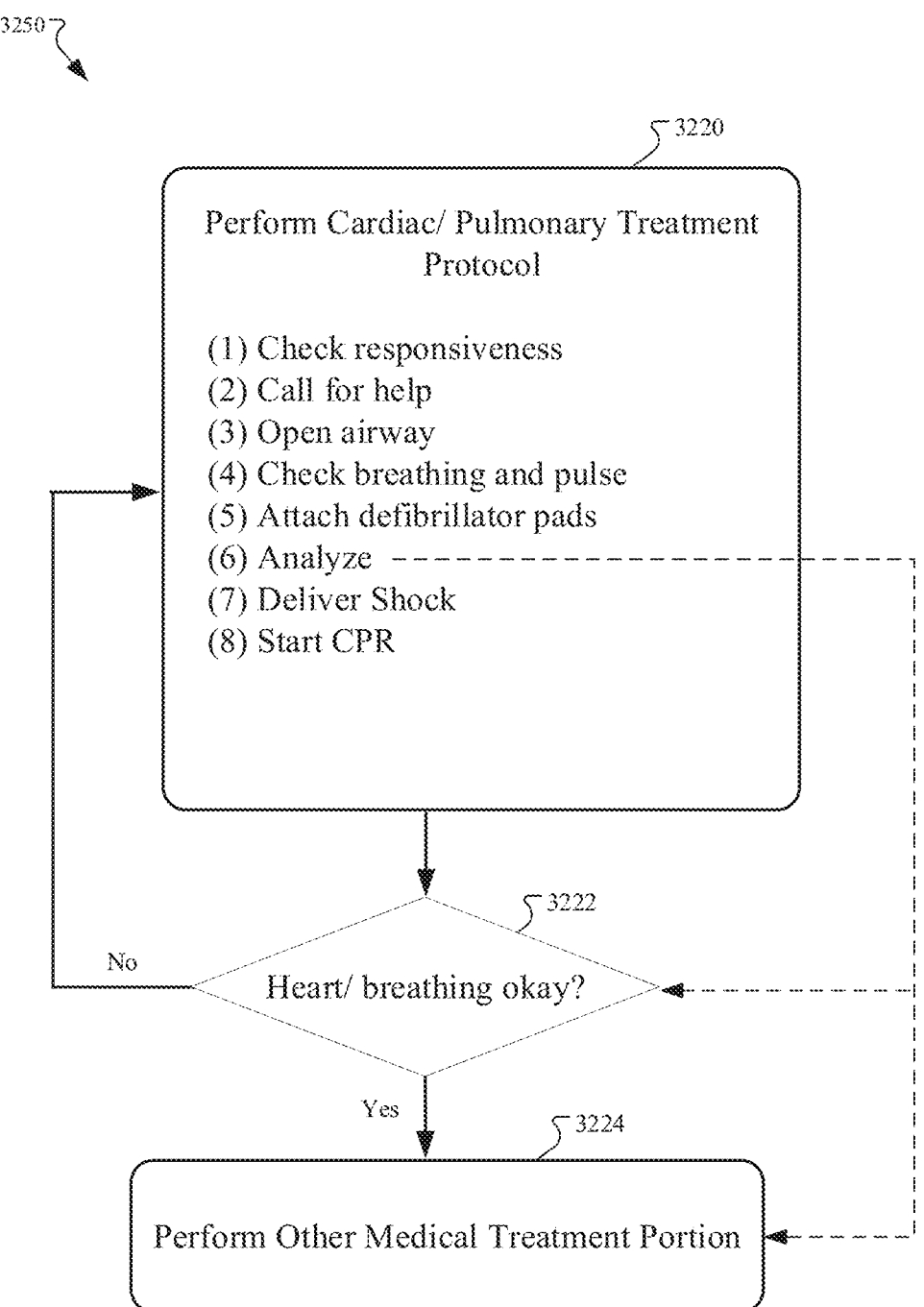
FIGS. 4A-4D show diagrams that illustrate various different options in which the portable medical treatment apparatus of FIG. 1A may navigate through an interactive query flow that involves a cardiac/pulmonary resuscitative treatment portion and another medical treatment portion.

A first option (option A) to integrate cardiac/pulmonary resuscitative treatment and other medical treatment into a single query flow is illustrated in FIG. 4A. According to option A 3250, the initial guidance provided to a caregiver is related to a cardiac/pulmonary resuscitative therapy. For instance, with the understanding that several of the steps illustrated may be applicable for non-cardiac arrest protocols and medical treatments the query flow may begin with the cardiac/pulmonary resuscitative treatment protocol 3220 by (1) instructing the caregiver to check the victim for responsiveness, (2) instructing the caregiver to call for help, (3) instructing the caregiver to open the victim's airway, (4) instructing the caregiver to check for breathing and check for a pulse, (5) instructing the caregiver to attach defibrillator pads (e.g., electrodes 3020a-b) so as to be able to obtain an ECG signal of the victim, (6) analyzing patient data (e.g., a heart rhythm of the victim) using a processor of the portable medical treatment apparatus 1000 (e.g., the processor 3032, the control board 3024, or a processor of tablet computing device 3002), (7) in response to determining that the victim is suffering from a shockable cardiac arrhythmia, delivering a shock to the victim via the defibrillator pads, and (8) instructing the caregiver to start CPR.

The CPR instruction may include a prompt to perform chest compressions and also an optional prompt to administer ventilations to the victim (e.g., using a ventilation unit such as a bag-valve mask provided by the portable medical treatment apparatus 1000). For instance, the apparatus may instruct the caregiver to administer CPR according to a 30:2 protocol (30 chest compressions:2 ventilation ratio). In some embodiments, the interactive query flow of the portable medical treatment apparatus 1000 may instruct the caregiver on how to find and use a ventilation unit (e.g., bag-valve mask) from the apparatus, and may optionally instruct the caregiver to find and use feedback equipment for assisting the caregiver in providing chest compressions and ventilations according to desired targets. If CPR feedback equipment is used from the apparatus 1000, the query flow may provide instructions and/or feedback for the caregiver to provide chest compressions according to desired compression parameters (e.g., 2.0-2.4 inches compression depth, 100-120 compressions per minute) and/or manual ventilations to the victim according to desired ventilation characteristics (e.g., tidal volume, minute volume, ventilation rate) in a safe and effective manner. In some embodiments, the ventilation portion of the query flow may be available only for those who have identified themselves as having more advanced medical training as compared to lay users who have little to no previous medical training so as to reduce the risk of lung injury to the patient in the event that the ventilation unit is misused.

Option A can include instructions for the caregiver to check again the breathing and the pulse of the victim 3222 to determine whether or not the resuscitation has been effective. In response to determining that the victim is breathing and has an effective heart rhythm, the query flow according to option A 3250 can continue to provide instructions for other non-cardiac medical treatment 3224. Note that in response to the ECG rhythm analysis, "(6) Analyze," indicating that the rhythm is not shockable, the query flow may jump to either the cardiac and/or respiratory analysis/instruction 3222 or jump to the other non-cardiac medical treatment protocol 3224.

The cardiac and/or respiratory analysis 3222, responsive to performance of the options described with respect to the cardiac/pulmonary resuscitative treatment protocol 3220, can be performed by the portable medical treatment apparatus 1000. The cardiac and/or respiratory analysis 3222 may determine whether the victim has been resuscitated, for example, by determining whether the victim is experiencing an effective heart rhythm and/or has started breathing. This determination may be performed through further analysis of the victim's heart rhythm sensed using the defibrillator pads and/or through user responses to prompts presented to the caregiver on a user interface of the portable medical treatment apparatus 1000 (e.g., "Is the victim breathing?"; "Does the victim have a pulse?"; and/or "Is the victim conscious?"). In response to determining by the portable medical treatment apparatus 1000 that the victim has yet to experience an effective heart rhythm and/or has yet to start breathing, the portable medical treatment apparatus 1000 may repeat at least some of the above-described operations of option A 3250 of the query flow. For example, the portable medical treatment apparatus 1000 may repeat operation #6 ("Analyze a heart rhythm of the victim") and operation #7 ("Deliver Shock").

The other non-cardiac medical treatment protocol 3224, can be initiated in response to determining by the portable medical treatment apparatus 1000 that the victim has effectively been resuscitated, or is no longer in need of the cardiac/pulmonary resuscitative portion of the interactive query flow. The portable medical treatment apparatus 1000 may transition from the cardiac/pulmonary resuscitative treatment portion of the query flow of option A 3250 to the other non-cardiac medical treatment protocol 3224 portion of the query flow of option A 3250. For instance, the portable medical treatment apparatus 1000 may present questions related to potential non-cardiac emergencies of which the victim may also or alternatively be suffering. For example, the portable medical treatment apparatus 1000 may present a user interface related to some other non-cardiac situation such as bleeding/blood loss, a broken bone, etc.

The option A 3250 of the query flow presents information related to cardiac/pulmonary resuscitation prioritizes analysis of potential cardiac/pulmonary emergencies over non-cardiac/pulmonary emergencies. The option A 3250 of the query flow may be particularly helpful in implementations of portable medical treatment apparatus 1000 that include few or no medical supplies that are non-cardiac in nature. For example, in an AED that can present a query flow able to help a caregiver treat non-cardiac emergencies but that does not include a comprehensive set of medical supplies, it may make sense to begin with cardiac/pulmonary resuscitative treatment because such treatment may be a strength and primary design goal of the AED Only upon determining that a victim is not suffering from a cardiac emergency may the AED then guide the caregiver in treating non-cardiac/pulmonary emergencies. The option for starting with a cardiac/pulmonary resuscitative portion of a query flow (i.e., Option A 3250) is not limited to devices or systems that are primarily AEDs, and may be used in any of the various different types of portable medical treatment apparatuses 1000 that are described herein.

Figure 4B:
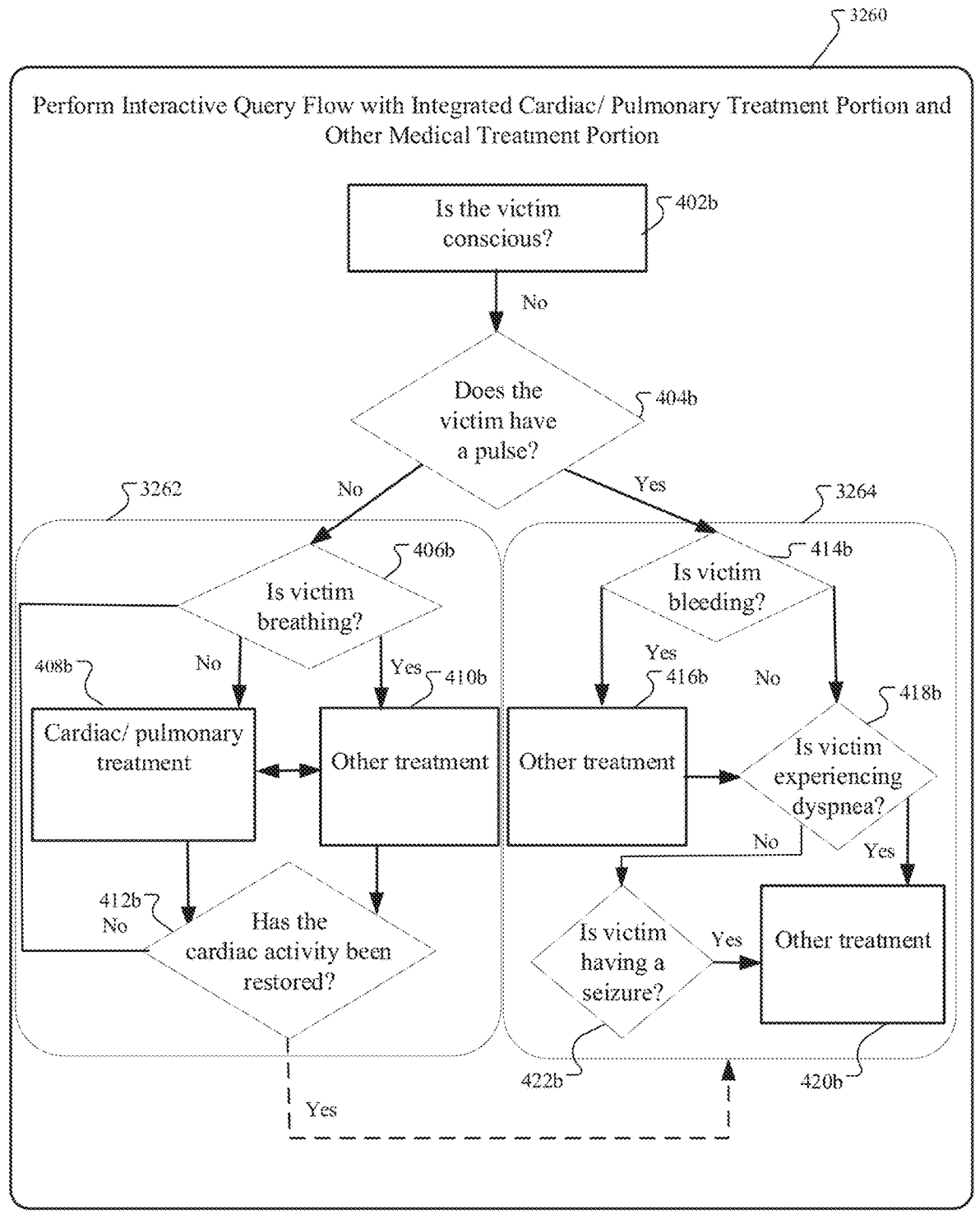

A second option to integrate cardiac/pulmonary resuscitative treatment and other medical treatment into a single query flow is illustrated by Option B 3260 in FIG. 4B. Option B 3260 can be labelled as being a "comprehensive query flow." Option B 3260 of the query flow can provide instructions to the caregiver to determine a type of injury which may span/integrate both cardiac and non-cardiac/pulmonary emergencies, agnostic to any particular medical condition, before guiding the user through treatment of the identified type of injury.

As illustrated in FIG. 4B, the portable medical treatment apparatus 1000 may begin the query flow according to option B 3260 in a same or similar manner to the query flow of FIGS. 4A, for example, by asking the caregiver whether the victim has suffered from a massive hemorrhage emergency, then transitioning to airway management, then respiratory management, then circulation, hypothermia, head injury, eye injury, and then everything else. The caregiver would interact with the query flow presented by the portable medical treatment apparatus 1000, answering various different questions and eventually being guided to an appropriate form of treatment.

An illustration of option B 3260 of the query flow can include a tree diagram, which begins with a question 402b for the user to indicate if the victim is conscious. The query flow according to option B 3260 proceeds from question 402b to a question 404b regarding a victim's cardiac condition, such as the determination of whether the victim has a pulse and potential identification of an ongoing cardiac event. Based on the answer to the question 404b, the query flow 3230 proceeds to either a cardiac/pulmonary query protocol 3262 or a non-cardiac/pulmonary query protocol 3264.

The cardiac query protocol 3262 can start with question 406b for the user to indicate if the victim is breathing. In response to receiving a user input indicating that the user is not breathing the portable medical treatment apparatus 1000 can proceed toward an electrotherapy-based protocol 408b for treating a cardiac/pulmonary emergency. In response to receiving a user input indicating that the user is breathing, the portable medical treatment apparatus 1000 can proceed toward a non-electrotherapy-based protocol. In some embodiments, the query flow may ask a further question 418b of whether the victim is breathing or experiencing respiratory distress (dyspnea). The non-electrotherapy-based treatments 410b may then lead toward instructions for administration of drugs or ventilations, for example, when the victim is experiencing shortness of breath or altered level of consciousness (e.g., decreased, combative) due to respiratory insufficiency. In some implementations, in response to determining that the cardiac/pulmonary therapy was successful, the portable medical treatment apparatus 1000 can continue the query flow with the non-cardiac/pulmonary query protocol 3264.

The non-cardiac/pulmonary query protocol 3264 can include a question 414b for the user to indicate if the victim is bleeding. In response to receiving a user input indicating that the user is bleeding, the portable medical treatment apparatus 1000 can provide an instruction 416b to the caregiver to deliver a non electrotherapy-based treatment (e.g., applying tourniquets, bandages, or pressure to control bleeding). In response to receiving a user input indicating that the user is not bleeding or after controlling bleeding, the portable medical treatment apparatus 1000 can provide a question 418b for the user to indicate if the victim is experiencing dyspnea. In response to receiving a user input indicating that the user is experiencing dyspnea the portable medical treatment apparatus 1000 can provide an instruction 420b to the caregiver to deliver a non-electrotherapy-based treatment. The non-electrotherapy-based treatments may include drugs (if appropriate drugs are available) or ventilation (e.g., manual ventilations according to that described above). In response to receiving a user input indicating that the user is not experiencing dyspnea the portable medical treatment apparatus 1000 can provide a question 422b for the user to indicate if the victim is having a seizure. In response to receiving a user input indicating that the user is having a seizure, the portable medical treatment apparatus 1000 can provide the instruction 420b to the caregiver to provide a non-electrotherapy-based treatment, such as keeping other people or objects (particularly sharp objects) away from the victim, and refraining from putting anything in the victim's mouth.

Figure 4C:
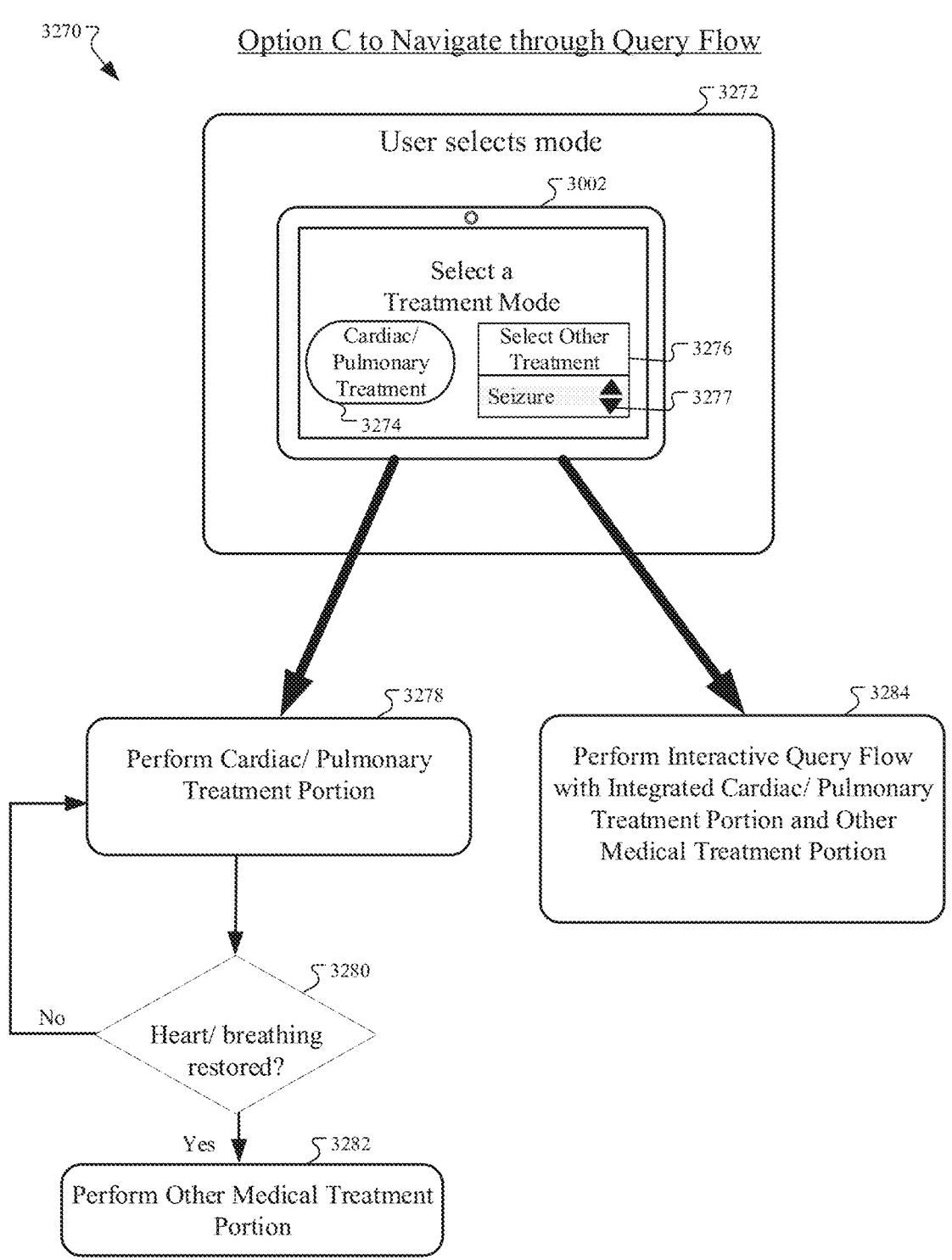
Figure 4D:
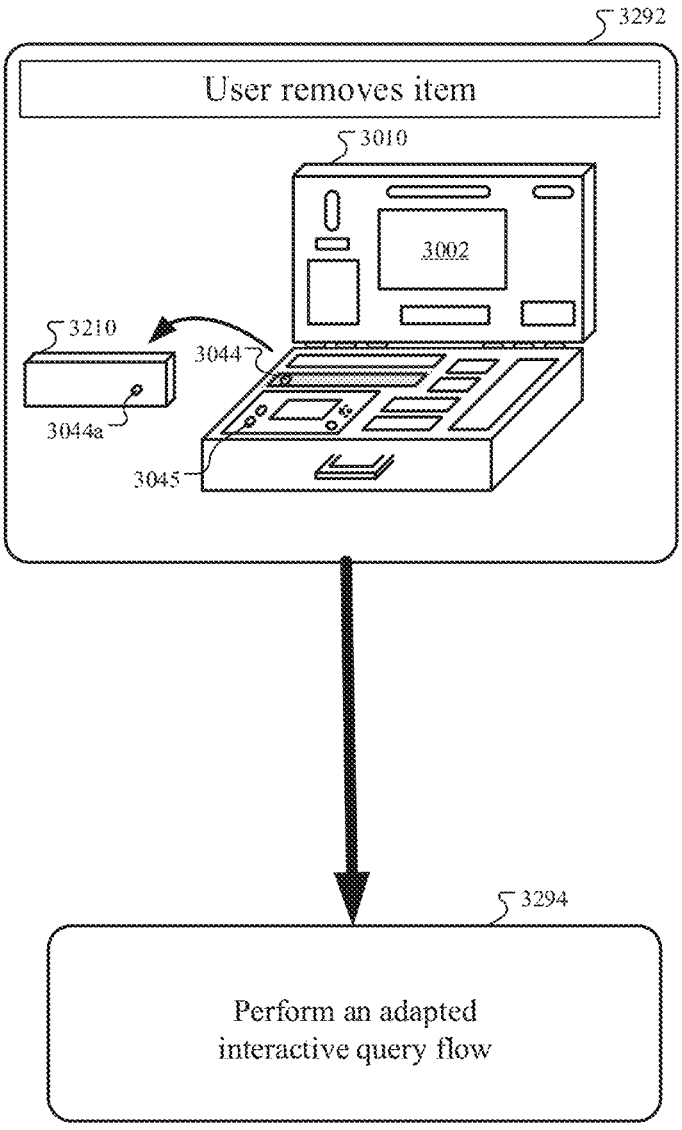

The query flow may provide a third option to select a treatment mode, as illustrated by Option C 3270 in FIG. 4C. With this option, the display 3002 may provide a user with a choice 3272 to bypass other inquiries of the interactive query flow and begin immediately with the cardiac/pulmonary treatment portion of the query flow 3274, or present a more generalized medical treatment portion of the query flow 3276 that can provide a treatment selection 3277, not immediately tailored to a cardiac/pulmonary treatment protocol. It may be advantageous to quickly move to the cardiac/pulmonary resuscitative portion of the query flow without taking up time that may otherwise be wasted by navigating through other inquiries that are not readily on point. For example, a touchscreen display device 3002 may request that a user "Select a Treatment Mode"—by either selecting a "Cardiac/Pulmonary Treatment" button 3274 or a "Select Treatment" (scrollable or drop down menu) option 3276. In such a case, the user may already know that the cardiac/pulmonary resuscitative portion of the query flow should be used, and so the appropriate input/button is actuated to jump directly to the appropriate portion of the query flow.

In response to receiving a user input including a selection of the "Cardiac/Pulmonary Treatment" button 3274, the portable medical treatment apparatus 1000 may start the cardiac/pulmonary resuscitative portion of the interactive query flow including instructions to perform cardiac/pulmonary resuscitative treatment portion 3278, providing questions regarding the cardiac and respiratory status of the victim 3280 and instructions to perform emergency medical treatment portion 3282, as described in detail with reference to FIG. 4A. In response to receiving a user input that selects the "Other Injury" button 3276, the portable medical treatment apparatus 1000 may start with the more comprehensive query flow 3284, as described in detail with reference to FIG. 4B and other sections of the present disclosure.

Note that regardless which button is selected, the portable medical treatment apparatus 1000 is still able to provide comprehensive guidance for a user to treat most types of major injuries or acute conditions. Whether the portable medical treatment apparatus begins by implementing cardiac/pulmonary resuscitative treatment (Option A) or interactive query flow (Option B), the portable medical treatment apparatus 1000 simply determines which treatments are given priority in the sequence of the query flow. In some example, the inputs or buttons 3274 and 3276 may include different text, for example, "Cardiac/Pulmonary Emergency" and "Non-Cardiac/Pulmonary Emergency." In some examples, the inputs or buttons 3274 and 3276 are physical or virtual buttons rather than touchscreen buttons.

It can be appreciated that for some embodiments, the user selection(s) provided by the inputs or buttons of the apparatus are not limited to a selection between cardiac/pulmonary treatment or more generalized emergency medical treatments, but may rather allow the user to jump directly to relevant portions of the overall interactive query flow to address other injuries/ailments. For example, other inputs/buttons available for user selection may allow the user to navigate directly to other portions of the query flow, such as for treating drug overdose, hemorrhage/bleeding, broken bone, difficulty breathing, seizures, etc.

Inventory Management

A fourth option to integrate cardiac/pulmonary resuscitative treatment and other medical treatment into a single query flow is illustrated with Option D 3290 of FIG. 4C. This option actually may be applied in combination with any of the described options A-C. In the context of Option D 3290, the portable medical treatment apparatus 1000 performs a detection operation 3292. The detection operation 3292 includes determining by one or more sensors that a user has removed an item from the case 3010. In response to the detection operation 3292, the portable medical treatment apparatus 1000 performs an adapted interactive query flow 3294. The adapted interactive query flow 3294 is configured to jump from a current position in the query flow to a portion of the query flow related to the removed medical item, similar to the previous embodiment where selection of a particular injury/condition may result in the interactive query flow jumping to the relevant section. In some embodiments, the detection operation 3292 may trigger the query flow to produce an additional screen/window or prompt that requests the user to confirm that the particular item has been removed. Such a confirmation may be helpful in case an item has been removed in error and interruption of the existing query flow is not warranted. Once the user has confirmed that the item has indeed been removed, then the apparatus may move to the adapted interactive query flow 3294 that relates to the particular removed medical item.

The portable medical treatment apparatus 1000 may include one or more sensors 3044 to determine whether a medical item has been removed and which medical item has been removed. In some examples, the case 3010 may include one or more sensors 3044 (illustrated in FIGS. 2A and 2B), and processor 3032 may analyze data captured by the one or more sensors 3044 to determine whether a medical item has been removed. The sensors 3044 can include image sensors, weight sensors, force sensors, photodetectors, optical sensors, electro-magnetic sensors, Hall effect sensors, capacitive sensors, or pairs of distance (proximity) estimation sensors 3044a (e.g., radiofrequency sensors, Bluetooth based sensors or magnetic sensors). In some implementations, the sensors include dedicated interrupters (e.g., photo-interrupters) that are located in the bottom of each storage cell. Each stored item can be housed in a structure with an interrupter vane that blocks the light across the photo-interrupter when the item is inserted in the storage cell. Alternatively, a QR-code or bar-code labels may be printed on each stored item and a camera of the lid of the case 3010 may read the codes. A camera may be provided in the case 3010 lid and may be positioned to have a field of view of the storage area and to perform image analysis to determine what has been put into and what has been removed from the case. This analysis may be performed through object recognition processes that identify which medical items are in the case 3010 at different points in time. The processor 3032 may compare the images to determine whether a medical item has gone missing or is in the process of being removed. In some embodiments, in the event that the removed item is not immediately in the field of view of the camera, the user may hold the removed item up to a camera integrated with the apparatus. The camera would then recognize that the particular item has been removed.

In some implementations, each removable item of the case 3010 may have a visible code displayed thereon (e.g., a QR code) that identifies the medical item. The processor 3032 may identify which visible codes are present in one or more captured images to determine which medical items are in the case and/or have been removed. Alternatively or additionally, the compartment in which each medical item is stored may include a visible code under a location at which the corresponding medical item is to be stored. As such, images that show an empty compartment (therefore exposing the visible code at the bottom of the empty compartment) may be analyzed to identify that a compartment is empty.

Other mechanisms in which the portable medical treatment apparatus 1000 may be able to determine that an item has been removed include each medical item being coupled to or contacting a mechanical switch (e.g., a pressure switch) that can detect removal of the respective medical item. Another mechanism to determine that an item has been removed involves each medical item including a radio frequency tag. In such an implementation, the near field communication radio 3064 may periodically broadcast signals and listen for replies transmitted from radio frequency tags that are proximate the near field communication radio 3064. Absence of a reply from a radio frequency tag that had previously been providing replies can indicate that a user has removed the radio frequency tag (and the associated medical item) from the case 3010.

In some versions, based for instance on image recognition or reading of bar codes or QR codes or other image-based inventory tracking methods, the system may detect the location of where an item is stored and then the user can be prompted as to its location when needed to use during a particular query flow. The visual prompt 3045 can be a highlight on the main display indicating which storage cell the target object is in. In some implementations, the display of the touchscreen display device 3002 can be dynamically adjusted to present an image of the target object to be removed 3100a, a location of the target object to be removed 3100b, or a highlighted representation of the target object to be removed 3100c and can include textual commands and graphical markers (e.g., arrows), as illustrated in FIGS. 3A-3C. The visual prompt 3045 can be an indicator proximate to or around the storage cell itself in the form of an LED or other type of light source (e.g., incandescent bulb, OLED, Laser etc.) to assist a user to find an item that is needed (e.g., storage cell lights up).

Each medical item in the case 3010 (or at least some of the medical items in the case 3010) may be associated with a specific location in the query flow that uses that medical item, to which the query flow is configured to jump upon removal of the corresponding item. For example, should a user remove a tourniquet from the case 3010, the query flow may jump to a portion of the query flow that either instructs the user how to use the tourniquet or asks the user questions regarding whether tourniquet use is appropriate before then instructing the user how to apply the tourniquet. Or, as discussed below, before even jumping directly to the tourniquet portion of the query flow, the apparatus may simply inform the user that the tourniquet has been removed and/or ask the user to confirm whether the query flow should navigate to the relevant section. Similarly, upon a user removing electrodes 3020a-b from the case 3010, the query flow may jump to a portion of the query flow related to electrotherapy (e.g., box 3220 in FIG. 4A).

In some examples, the query flow may not immediately jump to the portion of the query flow associated with a medical item that has been removed from the case 3010, and rather the portable medical treatment apparatus 1000 may prompt the user to indicate whether they would like to jump to the appropriate portion of the query flow. For example, the touchscreen display device 3002 may state "Removal of the tourniquet has been detected. Would you like guidance on how to use the tourniquet?" In response to the caregiver responding "Yes," the portable medical treatment apparatus 1000 may provide guidance regarding use of the tourniquet. Once guidance has been given for any item that has been removed, the query flow may continue onward in accordance with questions related to the removed item, or the query flow may revert back to the location of the query flow previously presented to the user before the portable medical treatment apparatus 1000 jumped to the location associated with the removed item.

Figure 5:
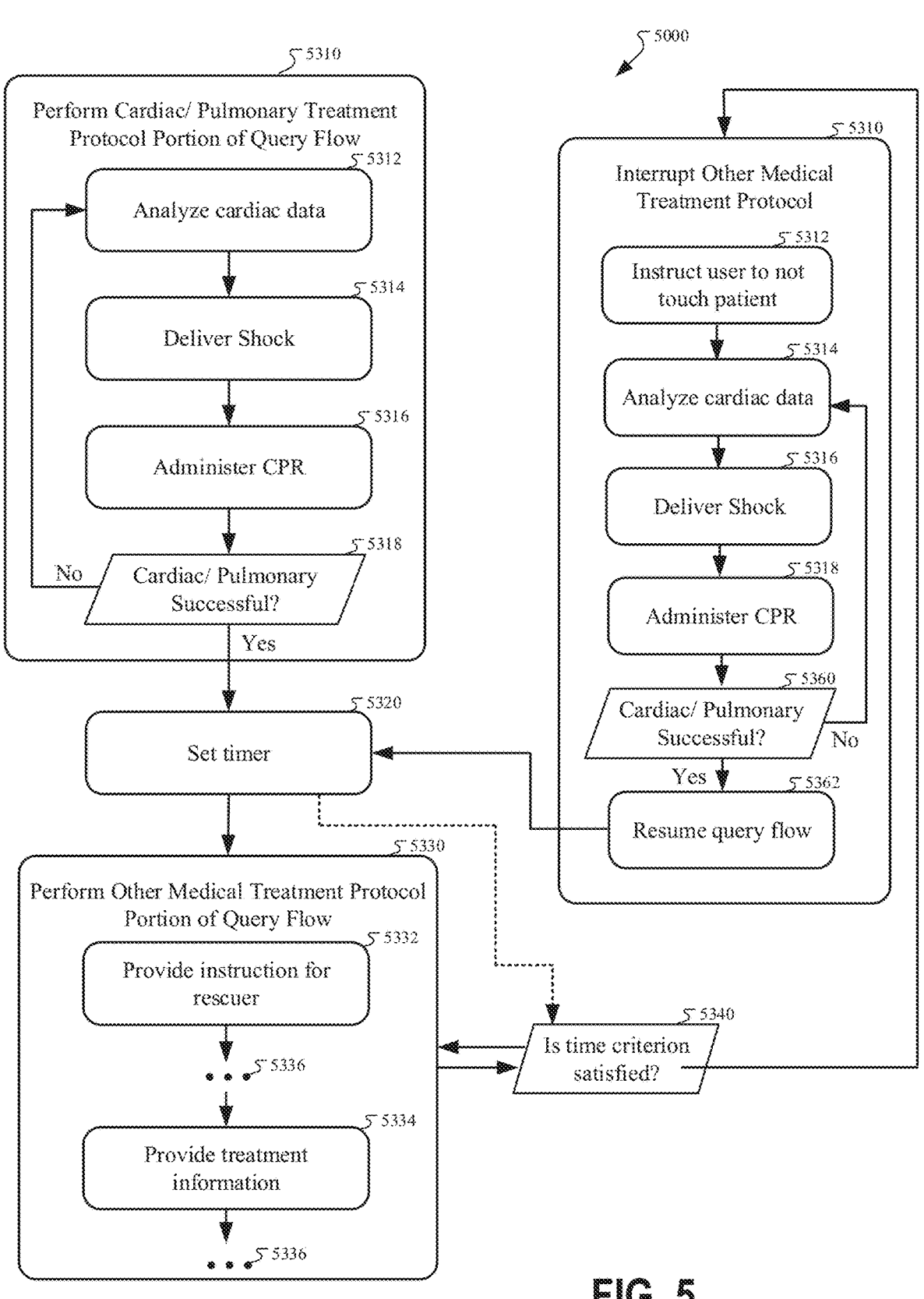
FIG. 5 shows a flowchart of a process in which the portable medical treatment apparatus of FIG. 1A transitions between a cardiac/pulmonary resuscitative treatment portion of a query flow and another medical treatment portion of the query flow.

FIG. 5 shows a flowchart of a process 5000 in which a portable medical treatment apparatus transitions between a cardiac/pulmonary resuscitative treatment portion of a query flow and another more generalized medical treatment portion of the query flow. The process begins at box 5310, which involves performance of a cardiac/pulmonary resuscitative treatment portion of the query flow. The portable medical treatment apparatus 1000 may perform the cardiac/pulmonary resuscitative treatment operations of box 5310 either at the beginning of a query flow (e.g., as illustrated with Option A in FIG. 4A) or in the middle of a query flow (e.g., as illustrated with Option B in FIG. 4B). Indeed, the operations of box 5310 may be the same as the operations of box 5220 (FIG. 4B), although box 5310 only shows a subset of the operations illustrated in box 5220 (FIG. 4B).

At box 5312, the portable medical treatment apparatus 1000 analyzes heart rhythms of the victim. For example, the portable medical treatment apparatus 51000 may have previously instructed a caregiver to place the electrodes 3020a-b on the victim, for example, by instructing the caregiver to do so and/or providing instructions for how to place the electrodes 3020a-b on the victim using one or more of displays 3002. In response to the caregiver placing the electrodes 3020a-b on the victim (e.g., as detected via transthoracic impedance measurements as measured between the electrodes) the portable medical treatment apparatus 1000 may use the electrodes 3020a-b to sense ECG signals indicative of the heart rhythm of the victim. A component of the portable medical treatment apparatus 1000 may analyze characteristics of the ECG using, for example, control board 5024 and/or processor 5032, in order to determine whether the victim is a candidate for application of a defibrillation shock. For example, the portable medical treatment apparatus 1000 may determine whether the sensed heart rhythm is indicative of the victim suffering from arrhythmia, and may determine characteristics of the arrhythmia. Should the portable medical treatment apparatus 1000 determine that the victim is not suffering from arrhythmia and is not a candidate for defibrillation, the portable medical treatment apparatus would not deliver a shock and may jump to the operations of box 5320 to set a timer and/or to enter into a continuous monitoring mode. In some implementations, the portable medical treatment apparatus 1000 can be configured to operate in a "continuous monitoring mode" in the background. In the "continuous monitoring mode" the portable medical treatment apparatus 1000 may monitor the cardiac activity of the victim in the background and continuously compare detected parameters to predetermined parameters based on one or more conditions that differentiate healthy (viable) cardiac activity from cardiac events that might require cardiac treatment to restore cardiac rhythm. In response to detecting (based on the monitored parameters) one or more conditions, the "continuous monitoring mode" can be terminated and replaced by a shock analysis determination. As context, performing an ECG shock analysis is a different type of processing based on an algorithm that is more complex and requires more computing resources than continuous background monitoring. For example, defibrillator/monitor devices can include a more basic ventricular fibrillation (VF)/ventricular tachycardia (VT) algorithm that sets an alarm for a caregiver to come and check on the patient if VF or VT is suspected. In this case, a typical VF/VT alarm may be used to trigger the apparatus initiating the shock analysis mode.

At box 5314, responsive to the portable medical treatment apparatus 1000 determining that the victim is a candidate for a shock (e.g., because the sensed heart rhythms are determined to be indicative of a shockable arrhythmia), the portable medical treatment apparatus 1000 may perform operations to deliver a shock. In "automatic" electrotherapy implementations, the portable medical treatment apparatus 1000 may deliver the shock without user input that presses a shock button (indeed, the portable medical treatment apparatus 1000 may not include a shock button). In "semi-automatic" electrotherapy implementations, the portable medical treatment apparatus 1000 may visually and/or audibly indicate that the device is ready to administer a shock, and may request that the caregiver press the shock button 5014 once all individuals have stood clear of the victim and are no longer contacting the victim.

At box 5316, after the portable medical treatment apparatus 1000 has administered the shock, the portable medical treatment apparatus 1000 may instruct the caregiver to administer CPR to the victim. For example, the portable medical treatment apparatus 1000 may provide instructions on one or more of the displays 3002 indicator lights or speaker for how to administer CPR to the victim, and/or may provide audible instructions for how to administer CPR to the victim. The portable medical treatment apparatus 1000 may also provide instructions on one or more of the displays 3002 or indicator lights or speaker on how to perform manual ventilation or other respiratory therapy such as delivery of a nebulizer bronchodilator for control of asthma or a diuretic for heart failure patients.

At box 5318, the portable medical treatment apparatus 1000 may perform an analysis to determine whether the victim has been resuscitated. For example, the portable medical treatment apparatus 1000 may analyze heart rhythms of the victim, as done at box 5312 (the "Analyze" step of the query flow), although the analysis may be more superficial (e.g., simply is the heart rhythm shockable, rather than a potentially more complex analysis performed at box 5312 to determine whether return of spontaneous circulation has been achieved). In some implementations, the analysis regarding whether the victim has been resuscitated involves the portable medical treatment apparatus 1000 querying the user to determine whether the victim is breathing and/or monitoring signals from the electrodes 3020a-b or other of the sensors in compartment 5018 to determine whether the victim is breathing. Should return of spontaneous circulation not been achieved, the portable medical treatment apparatus may provide an analysis as to whether to deliver another shock (box 5314) and/or request again that the user perform CPR (box 5316). The delivery of shock, performance of CPR, and determination of whether the victim has been resuscitated may cycle until the victim is determined to have been resuscitated or professional medical assistance has arrived.

At box 5320, upon the portable medical treatment apparatus 1000 determining that the victim has been resuscitated, the portable medical treatment apparatus 1000 may set a timer. In some implementations, the portable medical treatment apparatus 1000 can be configured to operate in a "continuous monitoring mode." In the "continuous monitoring mode" the portable medical treatment apparatus 1000 may monitor the victim in the background and then determine whether it should interrupt the non-cardiac portion of the query flow to return to the cardiac protocol, leading to a potential shock analysis and delivery. As described in additional detail below, the timer may be used by the portable medical treatment apparatus to determine a time at which to recheck the cardiac state of the victim. Setting the timer may include starting a countdown timer (e.g., starting a timer at five minutes that counts down to zero), although other mechanisms of starting a timer may be used. For example, the portable medical treatment apparatus 1000 may start a timer at 0 seconds that counts upwards, and, as described in detail later, the portable medical treatment apparatus 1000 may periodically check whether a threshold value (e.g., five minutes) has been met. In another example, the portable medical treatment apparatus 1000 starts the timer by recording a timestamp, for example, a time at which the victim was determined to have been resuscitated, and the portable medical treatment apparatus 1000 may periodically check whether a some amount of time (e.g., five minutes) has elapsed since recording the timestamp. Alternatively, if the patient is found not to have an arrhythmia that is treatable by cardiac/pulmonary resuscitative treatment based on step S312 and/or 5318, the query flow may jump to 5330 for other emergency medical treatment. For instance, if resuscitation fails more than a present number (e.g., 2, 3, or 5) times, the query flow may jump to 5332 and ask the caregiver to check for a collapsed lung (pneumothorax), which may give rise to sudden chest pain and shortness of breath.

At box 5330, the portable medical treatment apparatus 1000 performs the other medical treatment portion of the query flow. This performance of the other medical treatment portion of the query flow after the cardiac/pulmonary resuscitative portion of the query flow may occur in both Option A and Option B of FIGS. 4A and 4B. The performance of the other medical treatment protocol portion of the query flow can involve a series of questions and presentation of information by the portable medical treatment apparatus 1000. For example, box 5332 represents the presentation of one or more non-cardiac questions such as questions related to a broken limb, blood loss, or some other non-cardiac trauma or emergent situation. Box 5334 represents the presentation of treatment information related to the non-cardiac situation. The presentation of treatment information may include the presentation of multiple user interfaces and the operation of multiple flowchart boxes. The ellipses 5336 are intended to illustrate that the sequence of questions offered, user input solicited and received, and treatment information provided may take various forms, depending on user responses and where in the query flow the cardiac/pulmonary resuscitative protocol of box 5310 was performed (e.g., was the cardiac/pulmonary resuscitative treatment protocol an initial portion of the query flow as with Option A, was the cardiac/pulmonary resuscitative treatment protocol provided in the middle of the query flow as with Option B, or was the cardiac/pulmonary resuscitative treatment protocol provided as an interruption to the query flow, as when a user removes a medical item, as with Option D).

At box 5340, the portable medical treatment apparatus 1000 determines whether a specified timer criterion has been satisfied. The determination of whether the timer criterion has been satisfied may include a processor repeatedly checking whether the timer has reached the relevant criterion (e.g., whether the timer has counted down to "0," the timer has counted up to a threshold value, or a predetermined difference between a current time and the timestamp recorded during the operations of box 5320 has occurred). In some implementations, determining whether the timer criterion has been satisfied involves a processor including an interrupt that triggers upon one of the above-described criterions being satisfied.

At box 5350, upon the specified timer criterion being satisfied, the portable medical treatment apparatus 1000 performs the operations of box 5350 and interrupts the emergency medical treatment protocol portion of the query flow. The system may interrupt the query flow to perform a follow-up analysis of the heart rhythms of the patient (and/or perform other analysis of other health attributes of the victim using other of the sensors in compartment 3018).

It can be appreciated that a timer is not necessary for some embodiments where a portion of the interactive query flow such as a section of the other medical treatment protocol is interrupted. For example, the apparatus may provide for continuous background monitoring of the victim, particularly in cases where electrodes and/or other sensors are placed on the victim's body. In such cases, signals from the sensor(s) and/or electrode(s) may provide an indication that a particular medical condition is met, which would trigger an interruption where the interactive query flow immediately jumps to another section. In other words, the apparatus may incorporate a continuous monitoring algorithm that runs in the background while other medical activity/treatment is occurring, where the algorithm may be able to detect whether a more serious condition is present that would merit moving immediately to another part of the query flow. To provide a more specific example, the continuous monitoring algorithm may be able to detect whether the victim's ECG is indicative of a VF/VT arrhythmia, which would warrant a more deliberate complex shock analysis determination.

The query flow may then jump to a cardiac/pulmonary resuscitative portion where the responder is instructed to remove his/her hands from the victim so that a clean ECG analysis may be performed, to determine whether a shockable rhythm is present. If a shockable rhythm is then detected, then the appropriate electrotherapy may be immediately given. Though, if the continuous monitoring algorithm does not detect a rhythm indicative of VF/VT, then the query flow remains uninterrupted and the responder continues to follow the path of questions laid out for diagnosis and treatment with the monitoring algorithm continues to run in the background. If at a later time the monitoring algorithm detects the presence of a more severe condition, such as a VF/VT, then the interactive query flow is interrupted in favor of the more urgent care.

In some implementations, the portable medical treatment apparatus 1000 begins the interruption by instructing the user to not touch the patient (box 5352). For example, the portable medical treatment apparatus 1000 may present a message on a display, indicator light and/or an audible signal, to indicate that the portable medical treatment apparatus is going to re-check the victim's condition. As part of that message, the portable medical treatment apparatus 1000 may instruct users to step back from the victim and not touch the victim so that the portable medical treatment apparatus 1000 obtains accurate sensor readings. In some implementations, the portable medical treatment apparatus 1000 may instruct the user to press a button indicating that individuals are clear of the victim and not touching the victim before the portable medical treatment apparatus analyzes the victim's condition.

At box 5354, the portable medical treatment apparatus 1000 analyzes the victim's heart rhythm. The operations of box 5354 may be similar or the same as the operations of box 5312, which also relates to analyzing a patient's condition. Should the portable medical treatment apparatus 1000 determine that the victim's heart rhythms are effective and/or that the victim is breathing, the portable medical treatment apparatus may transition to the operations of box 5362 to resume the query flow (described in additional detail below). In some implementations, at box 5354, the portable medical treatment apparatus 1000 additionally or alternatively analyzes readings from other sensors from compartment 5018 at this stage of the interrupted query flow.

At box 5356, responsive to the portable medical treatment apparatus 1000 determining that the victim may benefit from a shock (e.g., because analysis of the victim's heart rhythms indicated a shockable arrhythmia), the portable medical treatment apparatus 1000 may administer a shock either automatically or semi-automatically, as described with respect to box 5312, for example.

At box 5358, responsive to the portable medical treatment apparatus 1000 administering a shock, the portable medical treatment apparatus 1000 may request that the caregiver perform CPR (e.g., chest compressions and/or ventilations), similar to the operations of box 5316.

At box 5360, the portable medical treatment apparatus 1000 may determine whether the victim has been resuscitated. For example, the portable medical treatment apparatus 1000 may determine whether the victim's heart rhythms are effective and whether the victim is breathing, similar or the same as the operations of box 5318. The portable medical treatment apparatus 1000 may continue to cycle through the operations of boxes 5354, 5356, 5358, and 5360 until the victim is determined to have been resuscitated.

At box 5362, responsive to the portable medical treatment apparatus 1000 determining that the victim has resuscitated, the portable medical treatment apparatus 1000 may resume the query flow 5362. Resuming the query flow may involve returning to the operations of box 5320 to set the timer and/or enable continuous background monitoring. The timer may be set with the same value as before (e.g., the same length of time), or the time value may be different. In some implementations, the value with which the timer is set depends on characteristics of the analysis of the victim, as performed at box 5360. For example, if the heart rhythms of the victim are effective and other measured victim health parameters appear strong, the timer may be set to a longer period of time than if the heart rhythms or other victim health parameters appear adequate, but not particularly strong. Furthermore, should the interruption in the emergency medical treatment protocol result in the victim needing a shock, the timer may be set to a shorter period of time because multiple instances of an irregular heart rhythm indicate that another instance of an irregular heart rhythm may be more likely to reoccur.

The resumption of the query flow (box 5362) may involve re-displaying the user interface that was presented before the timer and/or monitoring algorithm interrupted presentation of that same user interface with the operations of box 5340. As such, the query flow may return back to the previously-displayed user interface. In some implementations, the portable medical treatment apparatus 1000 may present information indicating that the emergency medical treatment portion of the query flow is resuming, for example, with a statement such as "The query flow is resuming where it left off before the analysis of the victim's heart."

In some implementations, the portable medical treatment apparatus 1000 may resume the query flow a few user interface screens earlier in the query flow than the user interface screen that was interrupted. In particular, it may be confusing to a user of the portable medical treatment apparatus 1000 if the system resumes at a question that was in the middle of a series of questions. Instead, the portable medical treatment apparatus 51000 may start at the beginning of a category of interrogation. For example, had the query flow been interrupted while the portable medical treatment apparatus 1000 was presenting a "Direct Pressure" with gauze animation, the query flow may not resume with an animation of the how to direct pressure with gauze, but may resume with a prompt such as "Locate Hemostatic Gauze", before presenting an operation or option such as "Looks like this," and then presenting the "Direct Pressure" with gauze animation.

In some implementations, the query flow may update based on information received from the analysis of the electrodes 1020-b and the other sensors described herein. For example, if the user is determined to have low blood pressure, the system may prioritize presentation of information related to potential emergencies that may contribute to low blood pressure (e.g., bleeding or fainting). The system may prioritize presentation of such information by either moving a current position of the user within the query flow to a different position, or by changing the order in which questions are presented in order to prioritize presentation of questions and/or information related to medical conditions that may be more likely based on sensor readings.

Figure 6A:
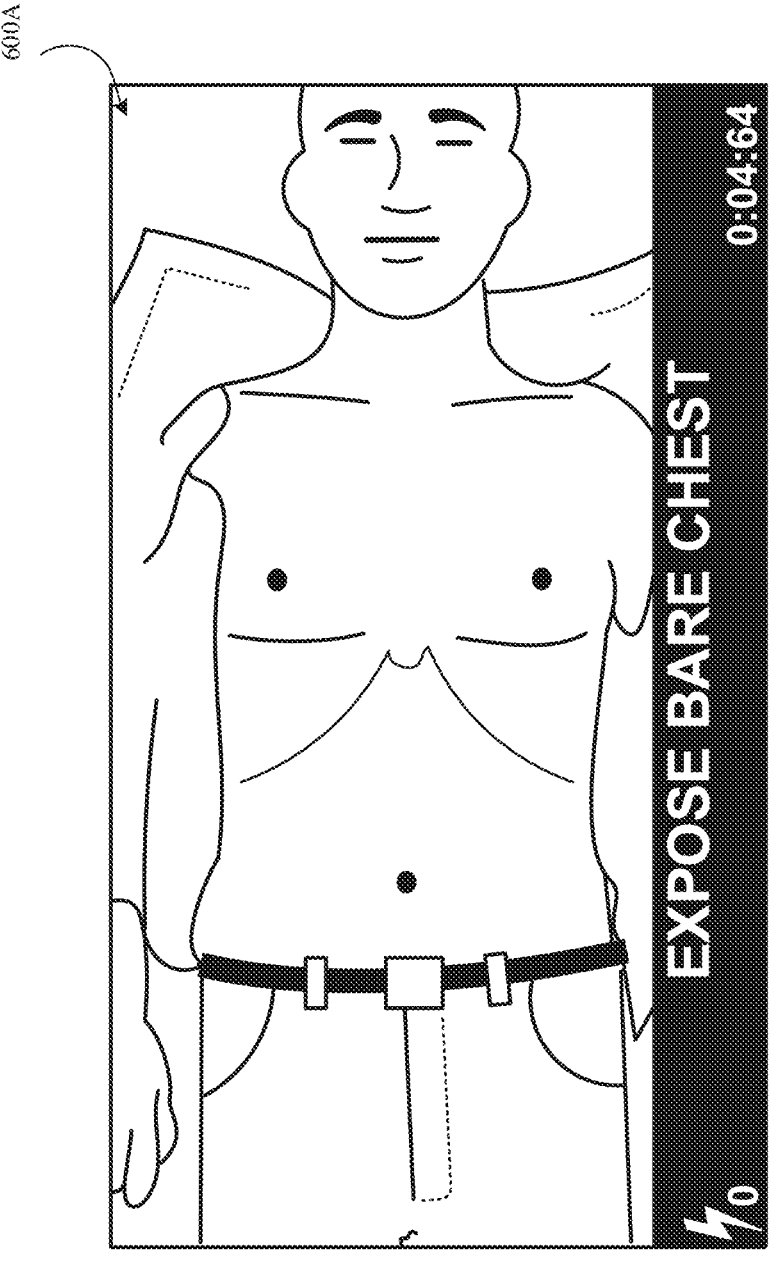
FIGS. 6A-8E show examples of the cardiac/pulmonary resuscitative treatment portion of a query flow provided by the portable medical treatment apparatus of FIG. 1A for a lay user without medical training.
Figure 6B:
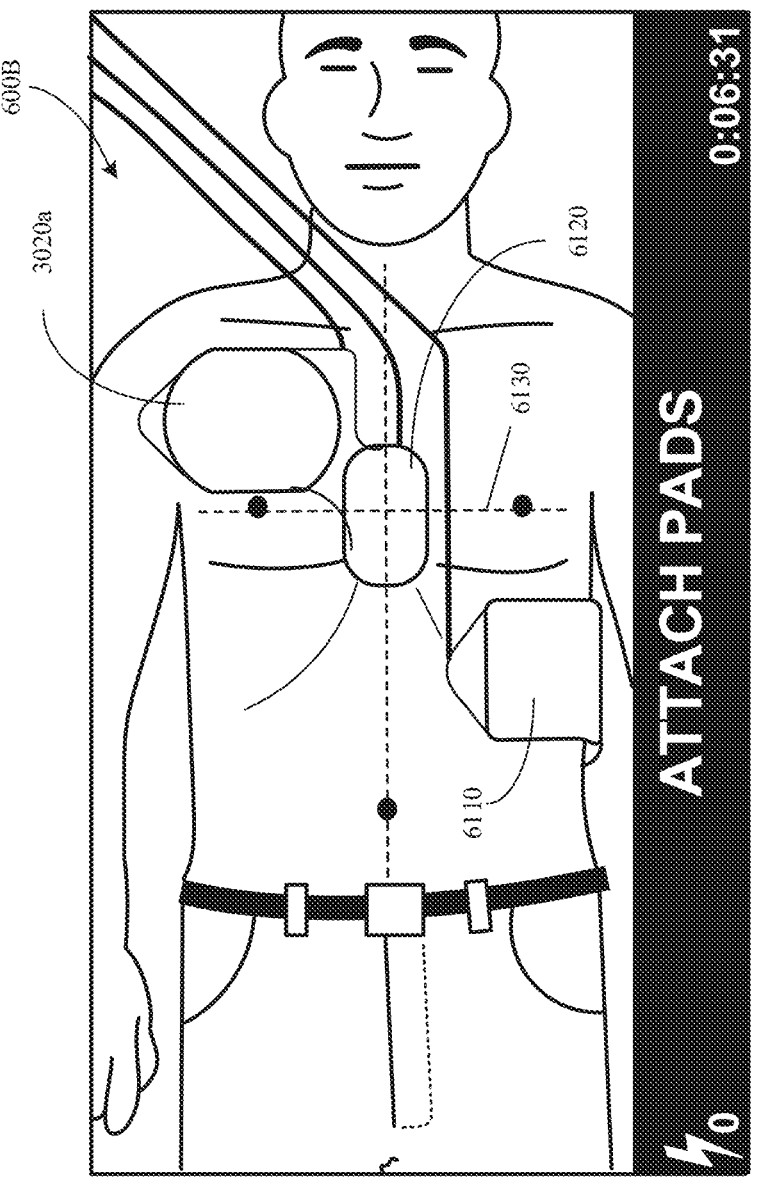
Figure 6C:
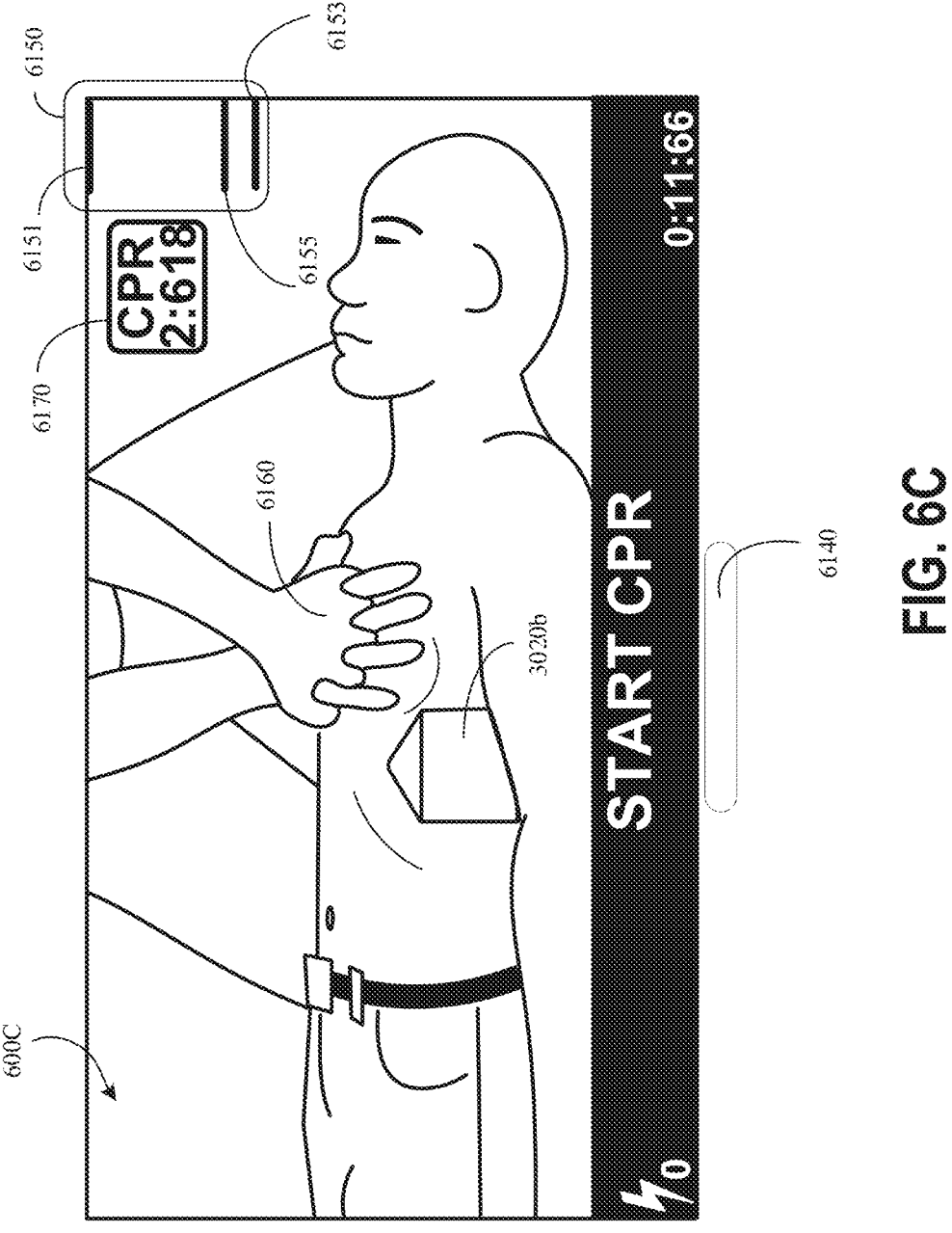

Referring now to FIGS. 6A-6C, examples of instructions for an untrained user that define portions of the query flows described with reference to FIGS. 4-5 are provided. As described herein, the interactive query flow may be tailored according to the level of medical training that is input by the user. For instance, the query flow may include options throughout each step for the user to identify themselves as having no previous medical training, a basic level of medical training and/or an advanced level of medical training, and otherwise default to the most basic level of prompting and instruction if no particular selection is made. FIG. 6A shows an example of an instruction 600A that can be displayed by display 3002 for an untrained caregiver to prepare an adult victim for treatment. As also described herein, the interactive query flow may provide a selection for the user to input whether the victim is adult or pediatric, and may further tailor the prompting and instructions accordingly. The display 3002 of the portable medical treatment apparatus 1000 FIG. 78 shows the instruction for exposing the bare chest for the mode-specific series of instructions for the adult patient (assuming that an input was provided that the victim is an adult). Since each piece of the electrode assembly can be placed on the chest of the adult patient during treatment, the instructions can show that a shirt need not be entirely removed from the adult patient. During treatment, a piece of the electrode assembly may need to be placed on the back of the patient, and so the shirt of the patient may inhibit treatment if it is not removed by the user. The images and text of the stage of instructions can be accompanied by audio prompts. For example, the audio prompt for the adult operating mode instruction of FIG. 3A can include instructions such as "expose bare chest," "cut or tear clothing to expose patient's bare chest," or similar verbal commands.

FIG. 6B shows examples of instructions 600B that can be displayed by display 3002 for an untrained caregiver to prepare the patient for placement of the electrode assembly 3020a, 3020b on the adult patient (e.g., the electrode placement stage). FIG. 6B shows an example of an electrode placement instruction 600B from the mode-specific series of instructions for the adult patient. The instruction can appear on the display 3002. The instruction can appear on the display 3002 after the patient has been instructed to remove the electrode assembly from a packaging stored in the case 3010. The patient's bare chest is exposed for placement of the electrode assembly 3020a, b. The electrode assembly 3020a,b is removed from packaging and the backing of each electrode is removed to expose the adhesive on the bottom surface of each electrode. An electrode 3020a is placed on the chest of the patient. The electrode 3020a can typically be placed on the right side of the adult patient's chest. The placement of the electrode 3020a can be assisted by the placement of an attached chest compression sensor 6120. The chest compression sensor 6120 can have a pattern, such as a dashed cross, on a top surface which guides the user for placing the chest compression sensor 6120 on the adult patient. The chest compression sensor 6120 is typically placed in the approximate center of the patient's sternum. The caregiver can orient the pattern on the chest compression sensor 6120 with an imaginary cross 6130 on the patient's chest and body. For example, a line can be imagined, drawn from the adult patient's chin to the adult patient's belly button intersecting with a line drawn across the adult patient's chest to form an approximate cross 6130 as shown in FIG. 6B. The user can place and orient the chest compression sensor 6120 such that the center or pattern of the sensor approximately corresponds with the intersecting point of the cross 6130. Such placement can correspond with where the user will perform chest compressions on the patient during CPR treatment as instructed during the query flow. The instruction can show text such as "attach pads as shown," "attach pads to patients bare chest," or similar.

In some examples, if the electrode 3020a is attached to the chest compression sensor 6120, the electrode 3020a may be automatically oriented to the approximate correct location for treatment on the chest of the adult patient if the chest compression sensor 6120 was placed and oriented as described above. In some examples, after the user has properly oriented and positioned the chest compression sensor 6120 and electrode 3020*a* on the adult patient's chest, the user can press the chest compression sensor 6120 and electrode 3020*a* into the skin of the adult patient so that the adhesive affixes the electrode 3020*a* and chest compression sensor 6120 firmly in place. A second electrode 3020*b* is affixed to the adult patient on an intercostal region. As shown in FIG. 1B, the electrode 3020*b* can be affixed to a lower left intercostal region of the adult patient such that the electrode 3020*b* wraps around the left intercostal muscles. Once the electrodes 3020*a* and 3020*b* have been affixed to the adult patient, the patient may be ready for treatment. If the user desires feedback on performing chest compressions during CPR, the chest compression sensor 6120 can be affixed to the patient as described above.

The first electrode 3020*a*, the second electrode 3020*b*, and the chest compression sensor 6130 can each be represented as a shaded object in the instructions. The color of the shading for the object can match a background color of piece of the electrode assembly represented by the object, such as the first electrode 3020*a*, the second electrode 3020*b*, or the chest compression sensor 6130. The relative shapes and sizes of the objects in the instructions can match the shapes, sizes, or both for each piece of the electrode assembly. The instructions on the display 3002 can match or be consistent with instructions on the electrode assembly, electrode assembly packaging, or both. Such consistency can help the caregiver associate the electrode assembly with the AED and facilitate use of the electrode assembly with the AED The instruction can show text such as "place pads as shown" or similar.

FIG. 6C shows examples of user instructions 600C for performing CPR for different mode-specific series of instructions, such as the query flow instructions described with reference to FIGS. 4A-4D. FIG. 6C shows an example adult CPR instruction 600C for performing CPR from the mode-specific series of instructions for adult patients. The instruction 600C can include one or more of pictorial instructions, textual instructions, and auditory instructions. The instruction 600C can appear on the display 3002.

The adult user configuration CPR instruction 600C can include CPR instructions as one or more pictorial instructions. For example, the CPR instruction 600C, as shown in FIG. 6C, shows the approximate hand placement for compressing the adult patient's chest during CPR. For example, the instruction 600C shows both the user's hands 6160 on the center of the adult patient's chest with fingers interlocked to perform CPR. The user is hunched over the patient such that the user can apply compression force with the user's full weight. The electrode 3020*b* is visible on the left side of the intercostal of the adult patient. The electrode can be depicted as faded, discolored or otherwise inconspicuous so as to deemphasize the importance of the electrode during CPR.

The adult CPR instruction 600C shows a compression feedback meter 6150. The meter 6150 can provide CPR feedback, such as in the form of an animated measurement, of the user's compression of the chest of the adult patient when the chest compression sensor 6130 is present. In one example, the meter 6150 can be two static bars 6153 and a third bar 6155. In some examples, the two static bars 6153 can represent an approximate suggested range of compression of the chest of the adult patient. The suggested range of chest compression for the adult patient may be set according to the most recent American Heart Association (AHA) Guidelines for CPR 6160 (e.g., between 2.0 and 2.4 inches). The third bar 6155 can represent a measured approximate depth of the compression of the chest of the patient. Hence, the caregiver may be advised to apply chest compressions such that the third bar 6155 remains within the region located between the two static bars 6153. In some examples, the area above the third bar 6155 can be shaded to illustrate a bar graph, rather than a single line, for assisting the user in visualizing the approximate measured depth of the compression being performed. The three bars can be approximately parallel. In an example representation of chest compression, the third bar 6155 can move within and outside of the range of the two static bars 6151, 6153. For example, when the chest of the adult patient is not compressed, the third bar 155 can be at approximately the same position on the display 3002 as the top of the display. When the chest is compressed, then the third bar 6155 may move down according to the depth of the compressions. In some cases, the third bar 6155 (or other bars or portions of the display) may be color coded depending on whether the compressions are within the desired range (e.g., according to AHA guidelines). For instance, when the compressions are within the desired range, one or more of the bars or other portions of the screen may be colored green (or another affirmative indicating color), though, when compressions are outside of the desired range, one or more of the bars or other portions of the screen may be colored red (or another color indicating an undesirable result). In one example, when the user compresses the chest of the adult patient, the third bar 6155 can move down the display 3002 toward the two static bars, which can provide a visual representation of the depth of the compression performed by the user. For example, the deeper the chest compression of the adult patient is measured, the lower the third bar 6155 can move on the display 3002. The meter 6150 can change colors when the measured chest compression is outside the suggested range of chest compression for an adult. For example, the meter 6150 can be a bright pink or green or other color indicating an affirmation in CPR performance when the chest compressions are within the approximate suggested chest compression range. When the measured chest compressions are out of the suggested range, the meter 6150 can turn a dark purple, yellow, red or other color indicating that the CPR applied needs to change. The chest compression feedback can include one or more of visual, auditory, textual, and haptic feedback. In general, CPR feedback may be provided in accordance with the latest AHA Guidelines for Cardiopulmonary Resuscitation and Emergency Cardiovascular Care.

The adult CPR instruction 600C can show a timer 6170. In one example, the timer 6170 can display the time elapsed since initiation of the CPR stage of treatment. Alternatively, the timer 6170 may display the amount of time remaining in the CPR interval. In some examples, the timer 6170 can countdown the appropriate time for the CPR stage of treatment before the user should progress to another stage of treatment such as ventilation, electric shock therapy or ECG measurement. The display may further show the elapsed event time (shown in the lower right corner of the figure), indicating the amount of time that has elapsed since the start of rescue and/or when the defibrillator is powered on.

Upon the cessation of chest compressions, the CPR instruction display may also show an idle timer, to provide the user with an indication of the time elapsed since CPR chest compressions have stopped. When the idle timer shows that a significant amount of time has elapsed, the caregiver may be more motivated to apply chest compressions to the patient. In some embodiments, the device may provide a series of escalating alerts to the caregiver to continue chest compressions based on how much time has elapsed as indicated by the idle timer.

The adult CPR instruction 600C can include textual instructions. Textual instructions on the display 3002 can change depending on the measured compression depth. For example, the textual instruction can read "push harder" if the compressions are too shallow, "reduce pressure" if the compressions are too deep, "good compression," "increase pace" if the compressions are being performed too infrequently, "push to match tone," "open airway," "check breathing," "continue CPR," "stop CPR," "breathe during CPR," and so forth.

The adult CPR instruction 600C can include one or more auditory instructions. The speaker 6140 can provide such instructions. The speaker 6140 can emit a metronome sound at regular intervals, such as a click, beep, tone, or other sound. The metronome sound can be at a pace that represents an approximate suggested pace (e.g., approximately 100 compressions per minute) for providing chest compressions during CPR. The speaker 6140 can emit spoken instructions which are relevant to the CPR treatment. For example, the spoken instructions can include "push harder" if the compressions are too shallow, "reduce pressure" if the compressions are too deep, "good compression," "increase pace" if the compressions are being performed too infrequently, "push to match tone," "open airway," "check breathing," "continue CPR," "stop CPR," "breathe during CPR," and so forth.

Figure 7A:
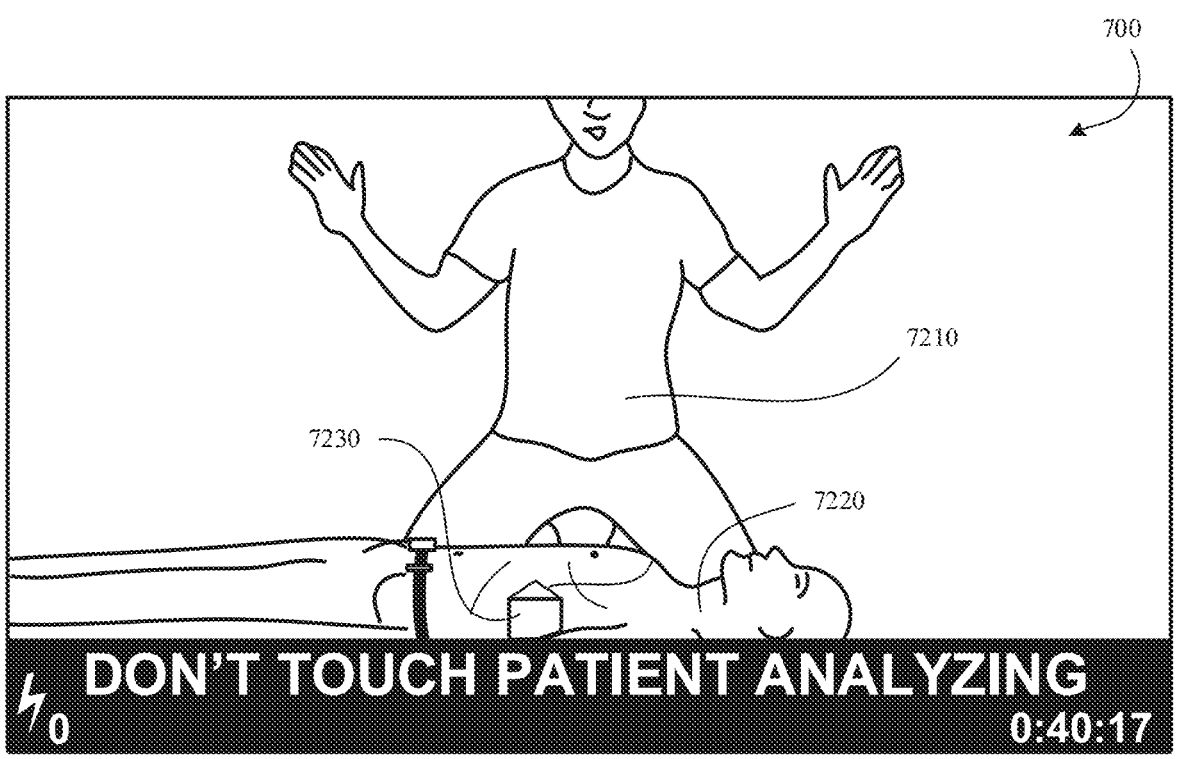
Figure 7B:
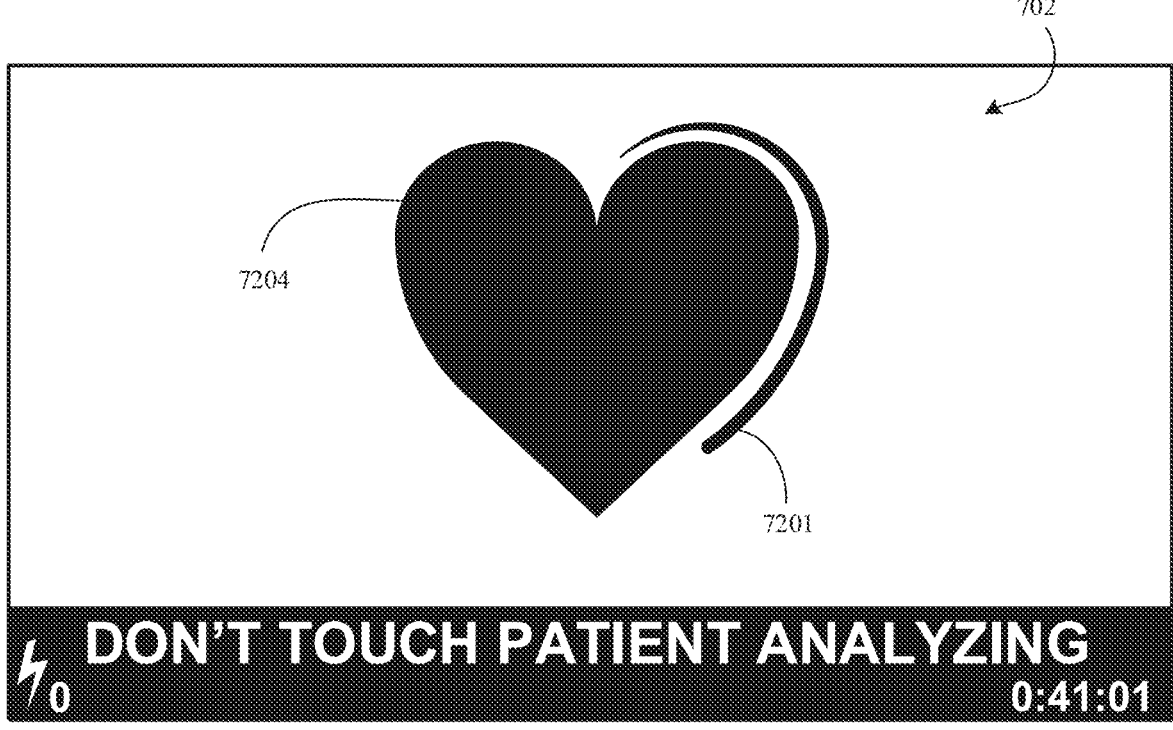

Referring now to FIGS. 7A and 7B examples of a shock therapy cycle are provided in graphical form for users with no previous medical training. FIG. 7A shows an example of an analyzing instruction 700 for the mode-specific series of instructions for the adult patient. The instruction 7200 can include one or more of pictorial instructions, textual instructions, and auditory instructions. The instruction 7200 can appear on the display 3002. For example, the analyzing instruction 7200 can display while the AED 6100 measures the adult patient's ECG signal to determine whether to prepare the AED to deliver an electric shock to the patient through the electrode assembly. The user 7210 is shown to be away from the adult patient 7220 such that the user is not in contact with the adult patient. The user 7210 can be advised not to contact the patient 7220 while the patient's ECG signal is being analyzed to determine whether a shockable or non-shockable ECG rhythm exists. In some examples, it is possible for such contact to disrupt the measurement of the patient's ECG signal. The user 7210 can be shown with his hands up and away from the patient 7220. The electrode 7230 is visible on the adult patient's abdomen. The color, size, and shape are approximately consistent with the adult instructions for electrode placement (e.g., as shown in FIGS. 6A-6C). The electrode can be represented inconspicuously so as to deemphasize the importance of the electrode during the analyzing stage of treatment.

The analyzing instruction 7200 can include textual instructions. Textual instructions can be used as input data for the analyzing stage and can appear on the display 3002 and can change depending on the measured vitals. For example, the textual instruction can read "don't touch patient analyzing" during analysis, "re-attach electrodes" if the electrodes detach from the patient, "plug in pads cable" if the cable detaches from the port 6180, "shock advised," "no shock advised," "check responsiveness," "call for help," and so forth.

The analyzing instruction 7200 can include one or more auditory instructions. The speaker 6140 can provide such instructions. The speaker 6140 can emit spoken instructions which are relevant to the analyzing stage of treatment. For example, the textual instruction can read "don't touch patient analyzing" during analysis, "re-attach electrodes" if the electrodes detach from the patient, "plug in pads cable" if the cable detaches from the port 180, "shock advised," "no shock advised," "check responsiveness," "call for help," and so forth.

FIG. 7B shows an example of an alternative analyzing instruction 7202 for the analysis stage. The instruction 7202 can be displayed in any operating mode, such as a layperson instructional operating mode. In the example of FIG. 7B, a symbol, such as a heart 7204, is displayed which has a cursor 7205 nearby. In some examples, the cursor 7205 can be animated to enhance the understanding of the instruction by an untrained layperson. For example, the cursor can move around the heart 7204 to indicate to the user that the AED is analyzing the patient's ECG, processing the results, or otherwise performing analysis. The instruction 7202 can include one or more of pictorial instructions, textual instructions, and auditory instructions which are similar to the described instructions In some implementations, a voting scheme can be employed to determine the presence or absence of shockability. A voting scheme uses fixed-length time segments. For example, data corresponding to three separate segments of ECG data can be processed to label the segments as either shockable or non-shockable, and the final decision can be based on the labels corresponding to at least two of the three labels. If the first two segments are labelled as shockable, the voting scheme can be terminated and the presence of a shockable rhythm can be identified. If the first segment is labelled as shockable and the second is labeled as non-shockable, a third segment is evaluated. In such a voting scheme, each segment is typically of fixed length, e.g., three seconds. Thus, when only using such a voting scheme, a minimum amount of time elapses before a determination can be made of whether a patient is in a shockable or non-shockable state. For example, if three-second segments are used, at least six seconds, and up to nine seconds, elapses before a determination can be made.

In contrast, in some implementations, the delay inherent in a voting scheme can be avoided, for example, by using high-accuracy clauses in determining the presence or absence of shockable rhythm. A clause is an expression that defines constraints on features of an ECG waveform underlying the ECG data; a clause is said to be met (or satisfied) if the criteria of the clause are met by the features of the ECG waveform being analyzed. In particular, if the criteria are met, then the ECG rhythm is said to be shockable or non-shockable, depending on the particular clause. High accuracy (e.g., low false positive rate) clauses may be created or defined in various ways. Using such high accuracy clauses can allow for identifying the presence or absence of shockable rhythms within a short time window (e.g., less than one second) thereby reducing analysis time as compared to, for example, the analysis time associated with a voting scheme. In some implementations, the high-accuracy clauses are determined heuristically by testing various candidate clauses for accuracy against a database of pre-stored patient data to determine clauses that have low false positive rates. In some implementations, the clauses can be determined, for example, by using a machine learning process on the database to identify conditions that indicate the presence of shockable rhythms with low false positive rates.

A display of an instruction may depend on the training level of the user. For example, because a trained user typically has a better understanding of medical data than a layperson does, the characteristics of the patient's ECG waveform will be differently displayed. Thus, even though data processing is independent of the user's training level, the display of the processing results can include different levels of details based on the training level of the user.

Although the use of high-accuracy clauses tends to be faster than the use of a voting scheme, a voting scheme can still be used in some situations (e.g., situations in which the user is medically trained and none of the high accuracy clauses are met and thus cannot be used in making the determination of whether a patient is in a shockable or non-shockable state). For example, normal-accuracy clauses may be used with the voting model described above.

The clauses with a sufficient level of accuracy for a particular time segment length ("high accuracy" clauses), as well as clauses with an insufficient level of accuracy for a particular time segment length ("normal accuracy") are defined with parameters that are calculated by processing ECG data stored in a memory buffer.

In some examples, high accuracy clauses are defined as having an accuracy threshold of 29% for a particular time length (width) of a waveform. In other words, if a clause is associated with a time length of 3 seconds and has an accuracy of at least 29%, the clause is a high accuracy clause.

In some examples, a particular clause is a high accuracy clause if the clause is applied to a portion of an ECG signal meeting a threshold time length (e.g., a length associated with the particular clause) needed to achieve some level of accuracy. Further, the same clause may be a normal accuracy clause if the clause is applied to a portion of an ECG signal that does not meet the threshold time length, e.g., the portion of the ECG signal has a length less than the threshold. In this way, as the length of the ECG signal portion increases, accuracy tends to increase as well. Thus, there will be a minimum time segment length below which a clause is only a normal accuracy clause, and is not suitable as a high accuracy clause, but for time segment lengths longer than this minimum time length, the clause is a high accuracy clause.

For instance, there may be clauses for which the minimum time segment length is 1 second, which are termed "1-second clauses." For instance, there may be clauses for which the minimum time segment length is 2 seconds, which are termed "2-second clauses." For instance, there may be clauses for which the minimum time segment length is 3 seconds, which are termed "3-second clauses." Segments for which the minimum time length is 6 seconds are termed "6-second clauses". Some examples of these are listed in Table 1.

TABLE 1

| Clause Timing | Intended Waveforms | Clause Logic | Result |
| --- | --- | --- | --- |
| 1 second | Normal sinus rhythm (one clear peak) | Maximum_slope > 200 microvolts ($\mu$v)/sample and relative_flatness > 100 | No Shock |
| 1 second | Asystole (low maximum and minimum amplitudes) | Max_amplitude < 50 $\mu$v and Min_amplitude < −50 $\mu$v | No Shock |
| 1 second | Slow VT | Peaks < 3 and average_peak_width > 160 milliseconds (ms) | No Shock |
| 1 second | PEA | Maximum_slope < 30 $\mu$v/sample and peaks < 3 | No Shock |
| 1 second | VFIB | Peaks > 3 and relative_flatness < 50 | Shock |
| 1 second | Fast VT | Peaks >= 4 and average_peak_width > 160 ms and peak_width_variability < 100 | Shock |
| 2 seconds | AFIB (many peaks but one or more tall peaks) | Maximum_slope > 200 $\mu$v/sample and relative_flatness > 80 and peak_tops_amplitude_variability < 250 | No Shock |
| 2 seconds | Slow PEA | Maximum_slope < 50 $\mu$v/sample and peak_tops_amplitude_variability < 250 and peak_tops_interval_variablity < 100 | No Shock |
| 2 seconds | VF (many peaks) | Maximum_slope > 50 $\mu$v/sample and relative_flatness < 50 and slope_zero_crossings > 20 | Shock |
| 2 seconds | VT (high rate and VT | R-R_ interval < 350 ms and QRS_Width > 140 ms and QRS_Width_Variation == 1 | Shock |
| 6 seconds | VT waveform (heart rate (HR) >150 bpm and wide complexes) | R-R_interval < 400 ms and QRS_Width > 140 ms and QRS_Width_Variation == 1 and flatness < 50 | Shock |
| 6 seconds | irregular PEA rhythm (intermittent flat areas and wide peaks) | flatness > 200 and pos_peak_width > 300 | No Shock |

Some additional 3-second clauses are found in Table 2.

TABLE 2

| Intended Waveforms | Clause Logic | Result |
|---|---|---|
| Few sharp peaks | ((Amplitude Variability < Threshold ) AND (Amplitude > 250 μv) AND (Maximum Slope > Threshold)) | No Shock |
| Stable HR and QRS width | ((QRS Rate > 220) AND (Width Variation == Stable) AND (Width < 100 ms)) OR ((SVT) AND (QRS Rate > 245)) | No Shock |
| Stable QRS width | ((Width Variation == Stable) AND ( QRS Width < 65) AND (Amplitude > 250) AND (QRS Rate > 300) | No Shock |
| Stable QRS amplitude, large QRS amplitude, clear peaks. HR > 180 | ((Amplitude Variability < Threshold) AND (Amplitude > 500) AND (Amplitude Variability <= Threshold) AND (QRS Variability < Threshold) AND (QRS Rate > 300) | No Shock |

Some additional 6-second clauses can be found in Table 3.

TABLE 3

| Intended Waveforms | Clause Logic | Result |
|---|---|---|
| Asystole waveform with very small electrical activity | (Average amplitude less than 100 μv) | No Shock |
| Fast PEA type waveform where HR > 160 with some variability and stable QRS width but maximum slope is low | (QRS Rate greater than 270 BPM) AND (QRS Variability < QRSV_Threshold) AND (Amplitude Variability < AV_Threshold) AND (Maximum Slope < Min_Slope_Threshold) AND (Width Variability > WV_Threshold) | No Shock |
| SVT type waveform, Number of SVT beats exceeds threshold, heart rate < 185, QRS width < 140 ms | ((SVT Beats Detected) OR ((NUMBER_OF_SVT_BEATS > SVT_CNT_Threshold) AND (QRS_Rate > QRS_Rate_Threshold) AND (QRS_Width < QRSW_Threshold)) OR ((NUMBER_OF_SVT_BEATS > SVT_CNT_Threshold) AND ( QRS Rate > QRS Rate Threshold 2) AND (QRS_Width < QRS Width Threshold)) | No Shock |

In a typical scenario, for some embodiments, a caregiver applies electrodes of a CPRS to a patient. The CPRS then collects ECG data, sometimes concurrent with a CPR treatment applied to the patient by the caregiver, or at times upon completion of a CPR treatment cycle or in between CPR treatment cycles. The CPRS collects and processes ECG data by evaluating clauses against time segments of the collected data. If at least one high-accuracy clause is met, the CPRS uses the state indicated by the clause (e.g., shockable or non-shockable) to direct the caregiver, or the defibrillating device itself, to administer a shock. In some implementations, in an adult operating mode, a shockable state may be identified in less than 6 seconds and sometimes within 2-3 seconds, within 1 second or less of the patient entering the state based on results of applying the clauses to the time segments of data. Other times, a three-step voting scheme employing fixed-length time segments predetermined prior to analysis is used, which may take at least 6-9 seconds or more to identify the patient's current state.

In some examples, the caregiver may halt the CPR treatment (e.g., due to express instruction to halt CPR treatment, during the natural course of repetitive CPR treatment, and/or during ventilations) while some of the data after completion of CPR treatment is being collected and analyzed for further confirmation of an initial determination of whether the rhythm is shockable or not shockable. Confirmation of an initial determination of shockability is sometimes referred to as a reconfirmation mode which may allow for filtered, eliminated or otherwise reduced CPR artifact in the signal during analysis, but it may pose a potential danger to the patient depending on how long the CPR treatment is halted. Thus, if the evaluation of clauses against time segments of the data is successful in determining the state of the patient after a relatively short amount of time, e.g., less than 6 seconds, the CPR treatment can resume relatively quickly, reducing risk to the patient. In some examples, reconfirmation mode is only available for adult patients, e.g., only available in an adult operating mode.

Figures 8A, 8B, 8C, 8D:
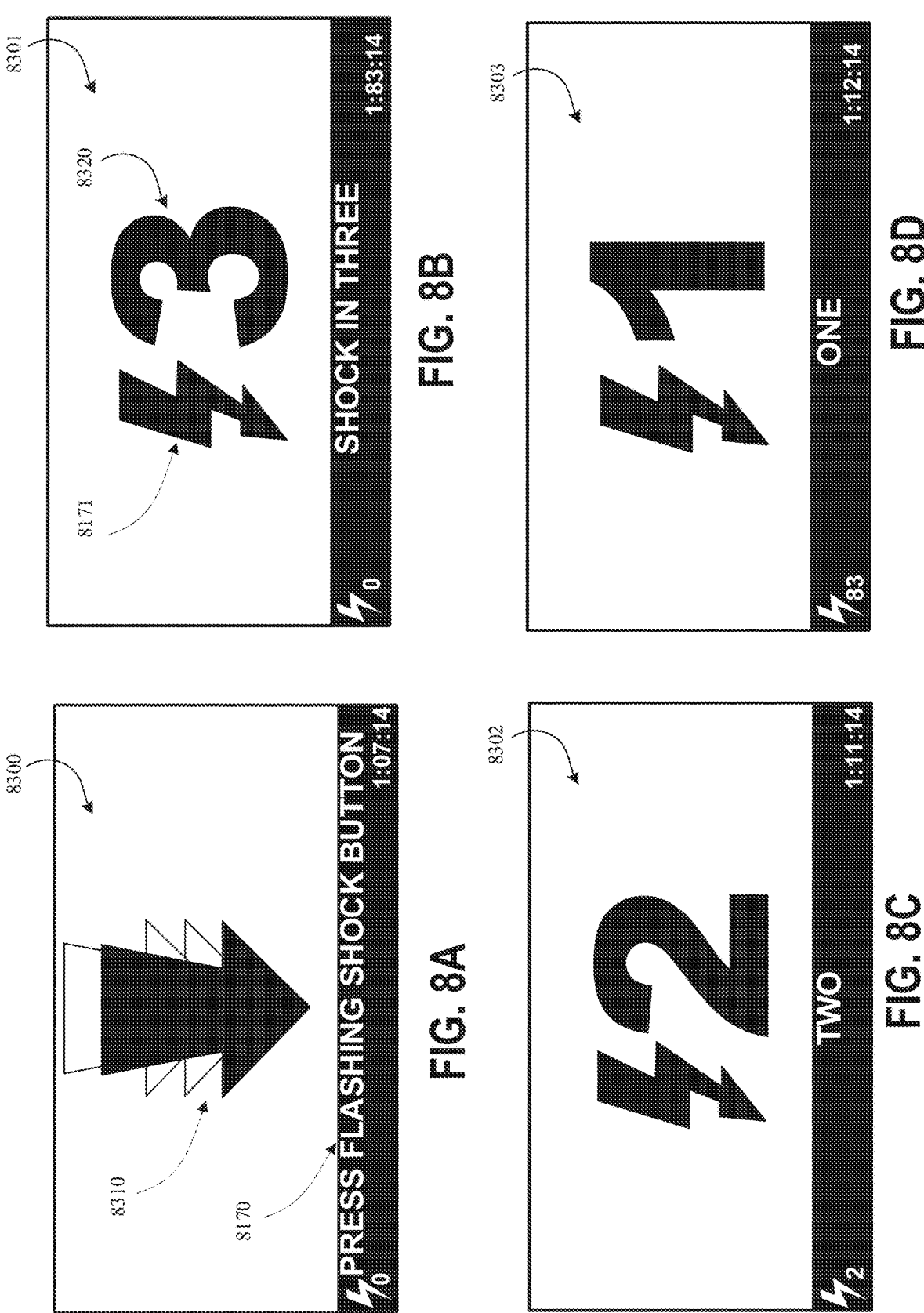

FIG. 8A shows an example of an instruction 8300 displayed if an electric shock is recommended. The instruction can be shown on the display 3002 and can include pictorial, textual, and/or auditory instructions. In some examples, the instruction can include a bright, vibrant color (e.g., orange, red, or similar). In some examples, the bright vibrant color can match the color of the shock button 8170 such that the user can associate the shock button 8170 with the instruction 300. The bright vibrant color can serve as a warning to the user to proceed with caution. The instruction 300 can include a large arrow 8310. The large arrow 8310 can be animated. For example, the arrow can move in a downward motion to suggest a pressing motion. In some examples, the instruction 8300 is skipped and the AED can automatically begin a countdown to electric shock.

The instruction 8300 can include textual instructions. For example, the textual instruction can advise a user to "press flashing shock button," "press shock button," "press shock button semi," "press shock button fully," or the like. The textual instruction can be delivered in auditory form, as discussed above.

Figure 8E:
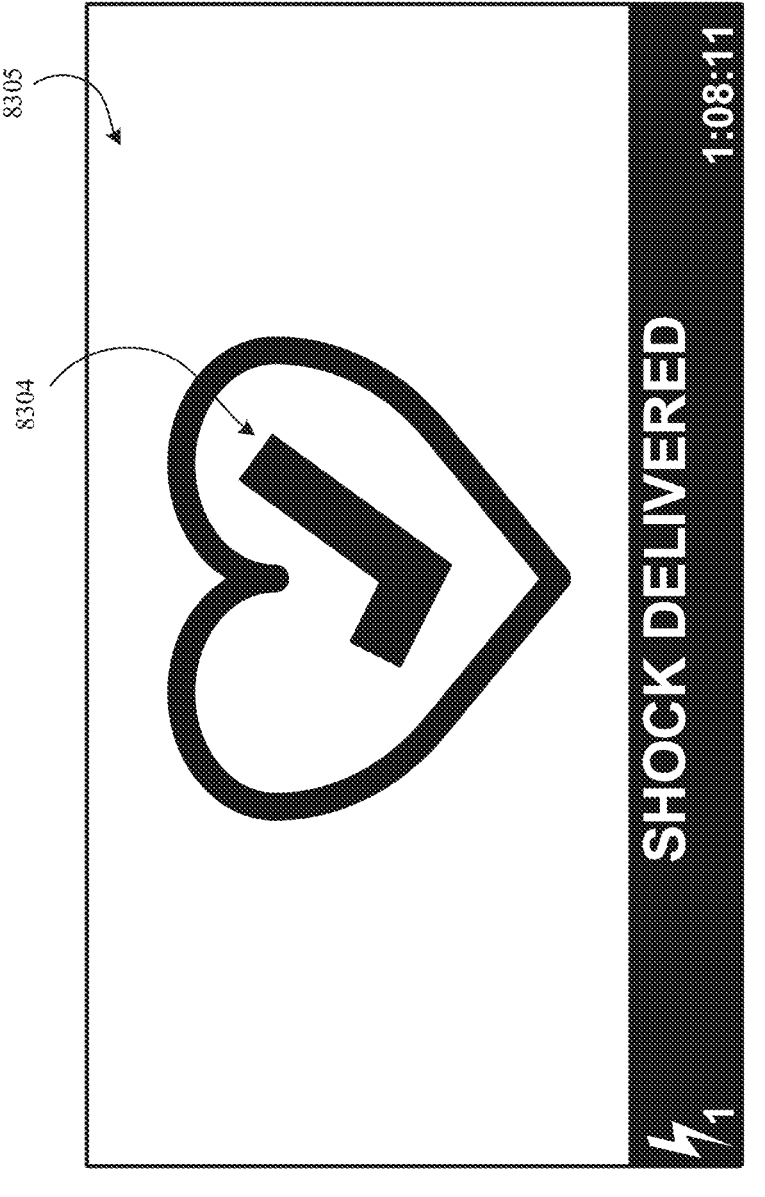

FIGS. 8B-8D show examples of a countdown during the electric shock therapy stage. In some examples, once the shock button has been pressed, the instructions in FIGS. 8B-8D can be shown in sequence to count down to the moment when the electric shock can occur. In some examples, the countdown can begin immediately once the computer processor determines that the electric shock is recommended. The countdown can serve as a safety measure such that the user is not accidentally shocked by the CPRS when handling the electrode assembly. The instructions of the interactive query flow can include large numerical digits 8320 which decrease in value in subsequent instructions. For example, the countdown can be from three to two to one before shocking. The numerical digits 8320 can be accompanied by the shock symbol 8171. The shock symbol 8171 can match a symbol on the shock button 8170 to enhance the ability of a layperson (untrained user) to perform the treatment. The shock symbol can be a symbol which connotes a relationship to electricity, such as a lightning bolt. In some examples, the countdown can be halted for various reasons, such as the pads disconnecting, subsystem malfunction, an abort by the user, and so on. If the computer processor detects that the electrode assembly has detached from the patient or is improperly configured, the query flow may return to the electrode assembly configuration stage. In response to determining that the shock was successfully delivered a confirmation 8304 can be provided, as illustrated by FIG. 8E. The confirmation 8304 can include a symbol and text to indicate the completion of the treatment.

Figures 9, 10:
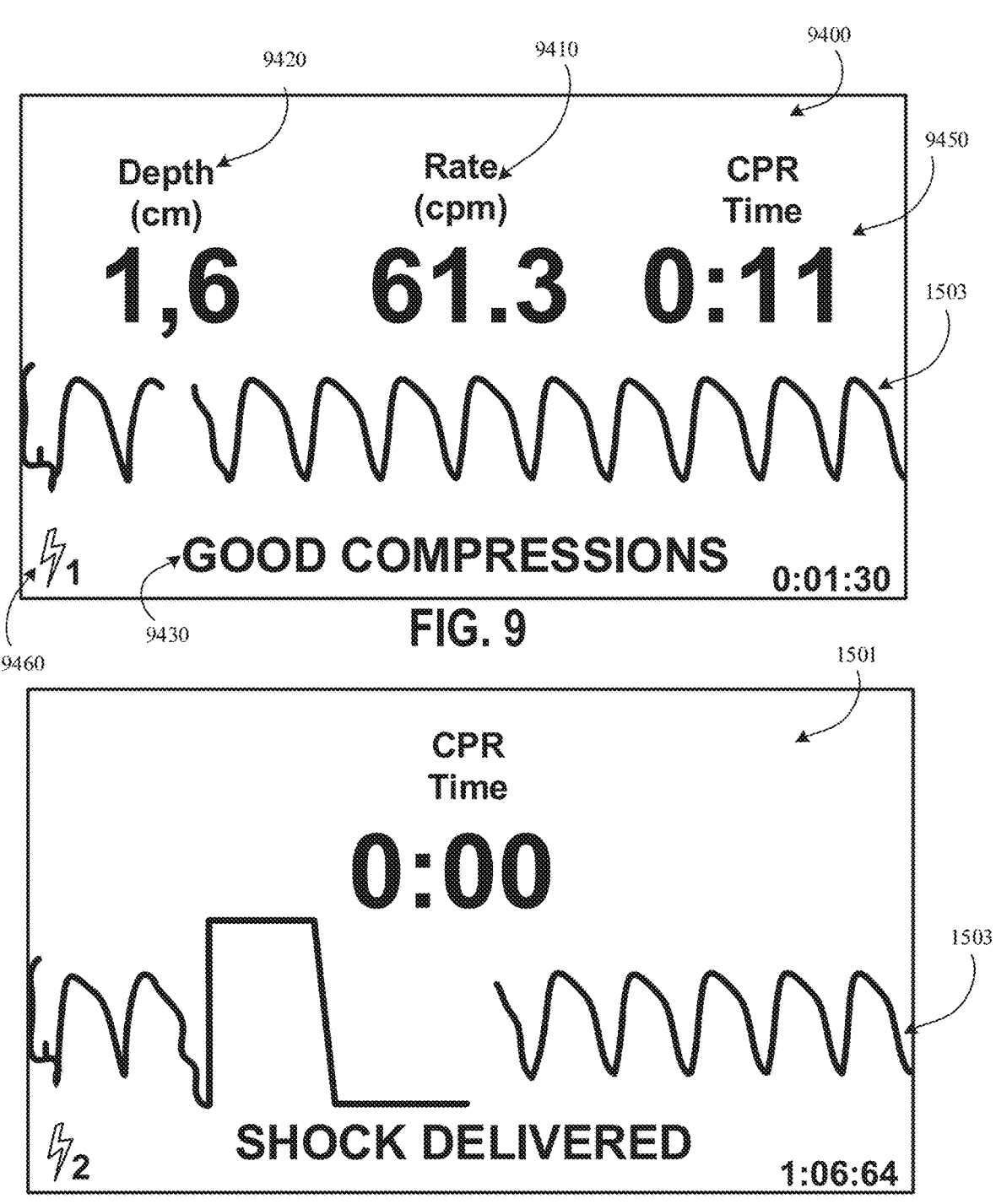
FIGS. 9-10 show examples of the cardiac/pulmonary resuscitative treatment portion of a query flow provided by the portable medical treatment apparatus of FIG. 1A for a user with more advanced medical training.

However, the query flow for a user with more training (e.g., professional ALS training) may include more detailed information (e.g., including real time measured data) for providing better treatment, such as compression depth and rate feedback and/or physiological information (e.g., ECG waveform) of the victim for the user to better assess the effectiveness of the treatment, as illustrated in FIGS. 9 and 10. For example, FIG. 9 shows an example of query flow for a user with more training to perform CPR therapy 9400. In some examples, the instruction can be shown on the display 3002 when the AED is configured to be used in professional mode. In some examples, the professional mode can be called a BLS mode, for personnel trained in BLS protocols. The instruction can be intended for a more experienced user, such as a professional responder or those trained in ALS protocols. The instruction 9400 can be more complex and include more feedback than the corresponding instruction in a non-professional (e.g., layperson) mode, so that the professional mode provides better support in assessing the rescue performance. For example, an ECG scale marker 410 measured by the CPRS can be displayed to the professional responder or user.

In some examples, numerical measurements of one or more of compression depth, rate, and time can be displayed. For example, a chest compression depth reading 9420 in centimeters can replace the compression feedback meter 6150 (FIG. 6). Numerical readings could confuse or distract a non-professional and so can be reserved for professional users. Though, because professional users may often be trained based on numerical values for chest compression, it may be preferable for professional users to view actual numbers to determine the quality of chest compressions that are provided. In some implementations, a chest compression rate number 9410 and a CPR countdown timer 9450 can be displayed. A user prompt can be displayed. For example, a text 9430 reading "Good Compressions" can be displayed to the user when the user is giving proper compressions to the patient. A number of shocks delivered 9460 to the patient can be displayed.

The professional mode instructions can be distinguished from the non-professional instructions such that it is quickly apparent in which mode the CPRS is operating. In some examples, the professional mode instructions each have a black background. As with the non-professional instructions, professional instructions can include pictorial, textual, and auditory instructions and feedback. In some cases, the display or other portion of the device may provide an indicator for informing a user of the current operational mode of the device. For example, when in BLS mode, the display might show a textual or graphical representation of the operational mode, such as "BLS," or a checkbox that is marked or unmarked to indicate whether the device is set to BLS mode, or another mode.

As discussed above, depending on the mode of operation to which the device is set, the type of chest compression feedback may vary. For example, when the device is operating in BLS mode and adult operating mode, the display may show numerical values of depth and rate of chest compressions, and the device may further provide CPR feedback, such as prompts for the caregiver to adjust the manner in which chest compressions are applied, for example, by pushing harder, pushing deeper, pushing softer, pushing faster, pushing slower, fully releasing from the chest, amongst others. The display may show numerical values of depth and rate of chest compressions based on user and patient's characteristics. As further depicted, the professional mode display provides other information. For example, the display may show a CPR countdown timer indicating the amount of time remaining in the CPR interval; an indication of the amount of time that has elapsed since the start of rescue or when the device has been powered on; and the number of defibrillation shocks that have been provided to the patient during rescue. The display may also show the ECG rhythm of the patient. The ECG rhythm provided on the display may be a raw ECG rhythm as detected by the electrodes or, in some cases, the ECG rhythm shown on the display may be a processed ECG rhythm that accounts for and filters out artifacts due to chest compressions.

FIG. 10 is example of a display 1501 during a professional mode where shock therapy is delivered. Similar to the example illustrated in FIG. 9, the instruction can be intended for a more experienced user, such as a professional responder. In some examples, the professional mode can be called a basic life support mode. The instructions provided in this mode can be more complex and include more feedback or information than the corresponding feedback or information provided in a non-professional (e.g., layperson) mode. For example, an ECG 1503 measured by the CPRS can be displayed to the professional responder or user. In some examples, in the basic life support mode, numerical measurements of one or more of compression depth, rate, and time can be displayed.

In order to provide compression depth and rate feedback, the medical apparatus may provide the user with a motion sensor (e.g., accelerometer) that provides signals for determining the depth and rate of compressions.

In some embodiments, the computer application may provide an objective system of questions or inquiries in accordance with the MARCHE triage protocol (Massive hemorrhage control, Airway management, Respiratory management, Circulation, Head injury/Hypothermia, Everything else) that leads a user through a course of treatment based on the user's responses to questions posed by the computer application. Specific choices are presented to the user based on where the user is in the query flow and based upon the user's answers to previous questions. For example, if during the query flow a user has indicated that the victim is currently awake and conscious, yet has subsequently lost consciousness, user interface screens presented thereafter may include a user selectable input (e.g., a soft key, button, etc.) that enables the user to inform the system that the victim has suddenly become unconscious, which may divert the query flow to another set of inquiries which may lead to respective treatment possibilities.

The computer application may direct the user to identify and first treat the worst injury, or the injury that would lead to death the soonest. The application also allows for the treatment of multiple victims and/or multiple injuries at the same time without having to exit and/or restart the query flow. In such a situation, the query flow can direct the user to locate and treat the injured party with the worst injury first, and then can continue to dynamically direct the user to locate and treat the remaining injured parties in descending order of injury severity.

Some implementations of the portable medical treatment apparatus may include— in addition to medical supplies such as gauze, a tourniquet, and pressure dressings— components that enable the treatment apparatus to record and analyze a victim's ECG rhythm, determine whether electrotherapy is required, and if needed, provide the electrotherapy to the victim. Such components may include a plurality of electrodes, an energy source and one or more capacitors to supply an electrical shock through the plurality of electrodes. Accordingly, user interface components of the treatment apparatus may include a touchscreen that enables a user to not only answer questions that are part of a portion of the query flow that is directed to non-cardiac injuries, but also may allow a caregiver to treat a victim suffering from cardiac arrest. As discussed further herein, the treatment apparatus may include a removable cardiac/pulmonary resuscitative subsystem that provides the user with flexibility in bringing only a portion of the apparatus necessary for providing cardiac treatment, without requiring the user to lift and re-position the entire apparatus closer to the victim.

Another type of medical treatment apparatus described herein is an AED with a display device that is adapted to present an interactive query flow that guides a user in treating not only cardiac arrest conditions, but also non-cardiac medical emergencies. For example, the AED may initially prompt a user to place electrodes on a victim's chest and may then analyze ECG and/or other cardiac parameters of the patient to detect whether a shockable rhythm exists. Should the AED determine that the victim is not suffering from life-threatening cardiac arrhythmia that would require defibrillation, or should the AED successfully treat the patient for cardiac arrhythmia (e.g., treating ventricular fibrillation or ventricular tachycardia through administration of a defibrillating shock), the AED may then present an interactive query flow to assess whether the victim is suffering from another type of medical emergency (e.g., blood loss, a seizure, an allergic reaction, drug overdose). Should a caregiver respond to questions posed by the query flow in a manner that is consistent with a victim suffering from another medical emergency, the interactive query flow may guide the user in treating that other medical emergency.

In some implementations, and described further below, the AED may include no additional medical supplies other than those typically found in traditional AEDs (e.g., defibrillation electrodes, CPR feedback equipment), or the AED may include a limited set of such additional medical supplies. As such, the interactive query flow presented by the AED may be similar or different than the interactive query flow presented by other medical aid apparatuses described herein. The interactive query flow may help a caregiver treat medical emergencies even though the AED may not come with a dedicated set of medical supplies. For example, in situations in which a victim may be suffering from a traumatic wound and a tourniquet may be helpful, the interactive query flow may suggest that the caregiver find a clean cloth and may instruct the caregiver on how to wrap the cloth above the injury. In other situations, the interactive query flow of the AED may suggest that the victim would benefit from a painkiller and may prompt the user to seek a painkiller elsewhere, such as from a first aid kit or from another person/source, if available.

As discussed herein, some implementations of portable medical treatment apparatuses may include a case or other housing that stores supplies and that includes a CPRS within the case that may be removable. This removable CPRS may include a subset of the components used to administer electrotherapy, for example, electrodes and optionally a shock button where electronics that analyze the heart rhythms and the capacitors may remain located in the body of the main apparatus, or simply controls for operating the defibrillator functions of the apparatus. Allowing some of these components to be located in a removable subsystem rather than fixed to the case may be helpful because a caregiver may not initially place the apparatus immediately adjacent a victim, and it may be easier to remove only a more portable module or subsystem from the case and bring that removable subsystem to the victim rather than move the entirety of the apparatus.

Different implementations of removable CPRSs can include different collections of components as part of the removable subsystem. For example, the removable CPRS may include a compartment within which electrodes are stored and from which the electrodes may be removed. The removable CPRS may also include a user interface (e.g., a speaker and a display) so that a caregiver that is applying the electrodes to the patient does not need to turn his or her attention away from the victim and to a comparatively larger apparatus that has been placed in an inconvenient location. The presence of a removable CPRS can enable an additional caregiver to interact with components in the case, for example a touchscreen of the case in order to provide responses to questions requested by the interactive query flow at the same time that the other caregiver is affixing the electrodes and directing his or her attention to prompts provided by the removable subsystem. The removable subsystem may be tethered to the case by an electrical cord that enables electrical communication and power transmission between the removable CPRS and the case, for example, high-voltage defibrillation energy transmission.

Different implementations of the portable medical treatment apparatus described herein may begin their query flows differently, for example, by initially inquiring about different types of medical emergencies. For example, a medical treatment apparatus can begin its interactive query flow with questions (e.g., inquiring whether the victim is unconscious and lacking a palpable pulse) that would lead the caregiver to provide cardiac arrest treatment (e.g., instructing the caregiver to place electrodes, removing his/her hands so that the device can analyze a heart rhythm of the victim, and providing cardiopulmonary resuscitation). Only once the apparatus has determined that the victim is not suffering from a shockable cardiac arrhythmia (or has successfully treated the victim for a shockable cardiac arrhythmia), may that device then continue to a portion of the interactive query flow related to potential non-cardiac emergencies, such as wounds, blood loss, fractures, burns, seizures, allergic reactions, and the like.

In another example, the interactive query flow may start with the beginning of the MARCHE protocol, initially asking the caregiver to answer questions related to whether the victim is bleeding. Only later in the interactive query flow may the system then prompt the caregiver to place electrodes on the victim in order to perform analysis of the victim's heart rhythms, such as after the caregiver has indicated that the victim is unconscious but not seizing, and without indication of a (palpable) pulse. In yet another example, the interactive query flow may begin with either of the above-described alternatives, but the medical treatment apparatus can include one or more sensors that are configured to detect that the caregiver or another person has removed an item from the case (e.g., an image sensor or more simple photodetector may capture images which are analyzed or assess the presence of a threshold amount of light to determine that electrodes, gauze, or a tourniquet has been removed). In response to the apparatus identifying that an item has been removed, the system may jump or otherwise direct the user to a portion of the query flow related to therapeutic use of the item. For example, upon the apparatus detecting that a user has removed the electrodes, the apparatus may interrupt the query flow by presenting on a touchscreen display the question "Electrode removal detected, would you like guidance on electrode use?", accompanied by selectable "Yes" and "No" buttons to confirm navigation to the appropriate section of the interactive query flow.

A benefit to combining cardiac/pulmonary resuscitative functionality with a device that provides guidance on treating non-cardiac medical emergencies (and potentially includes supplies to treat such non-cardiac medical emergencies), is that once electrodes have been applied to a victim and used for an initial electrotherapy analysis, those electrodes can remain on the victim and be used for subsequent analyses. These analyses can relate to non-cardiac medical emergencies, particularly where the system initially prompts the caregiver to apply not only electrodes, but also other sensors (e.g., a pulse oximeter, a blood pressure cuff) capable of measuring physiological activity. Moreover, the system can periodically re-analyze the heart rhythms of the victim to ensure that the victim has not transitioned from an effective heart rhythm to cardiac arrhythmia leading to cardiac arrest. For example, the apparatus can include a timer that, upon expiration, causes the apparatus to interrupt the query flow and prompt the caregiver to not touch the victim while the system monitors the heart rhythm of the victim with the electrodes. In response to determining by the portable medical treatment apparatus that the victim is experiencing an effective heart rhythm, the apparatus may transition back to the portion of the query flow that the apparatus presented before interruption.

Illustrative embodiments are described herein. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 11:
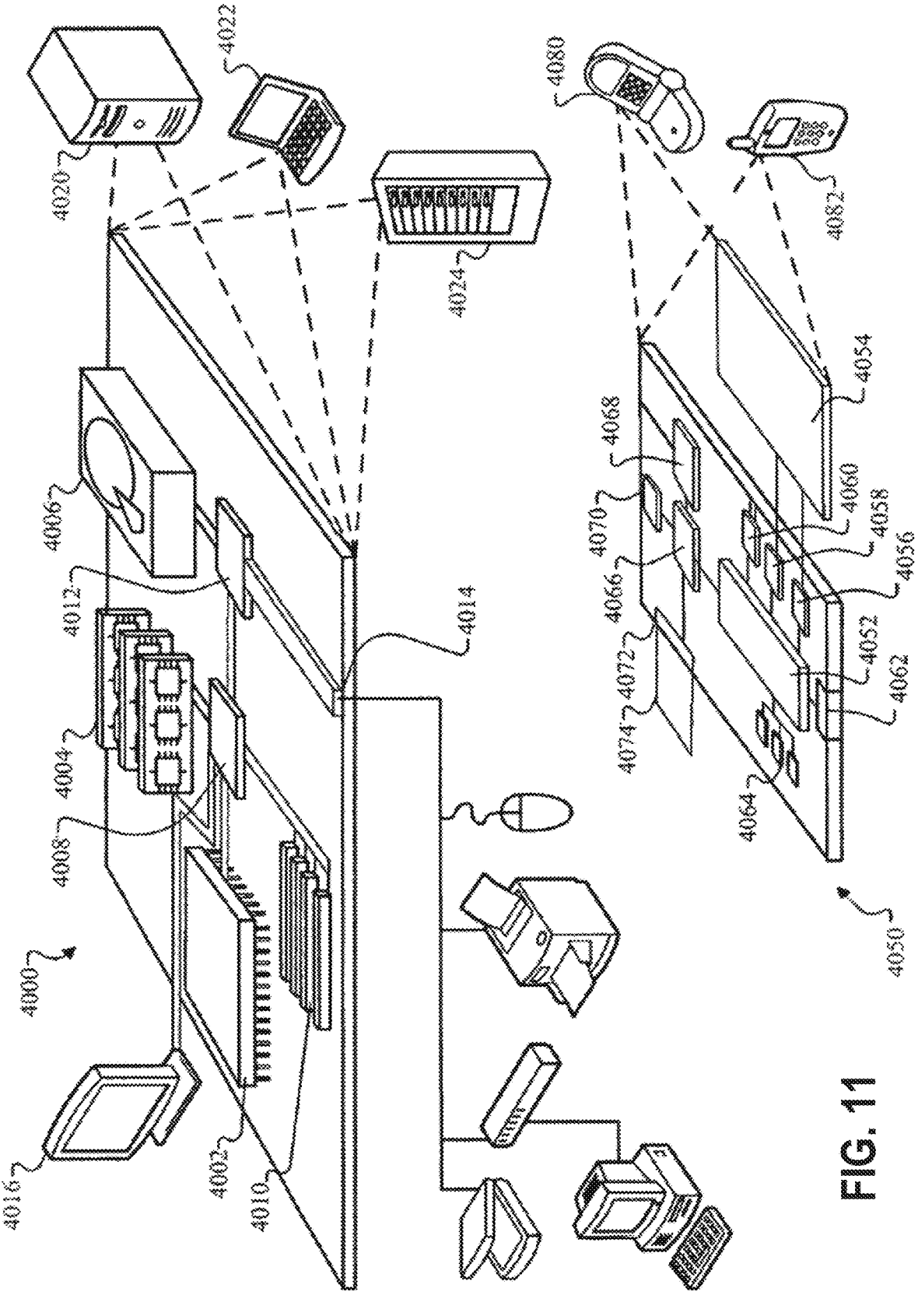
FIG. 11 is a block diagram of computer systems forming part of the portable medical tool kit of FIGS. 1A and 1B.

FIG. 11 is a block diagram of computing devices 4000, 4050 that may be used to implement the systems and methods described in this document, as either a client or as a server or plurality of servers. Computing device 4000 is intended to represent various forms of digital computers, such as laptops, desktops, workstations, personal digital assistants, servers, blade servers, mainframes, and other appropriate computers. Computing device 4050 is intended to represent various forms of mobile devices, such as personal digital assistants, cellular telephones, smartphones, and other similar computing devices. The components shown here, their connections and relationships, and their functions, are meant to be examples only, and are not meant to limit implementations described and/or claimed in this document.

Computing device 4000 includes a processor 4002, memory 4004, a storage device 4006, a high-speed interface 4008 connecting to memory 4004 and high-speed expansion ports 4010, and a low speed interface 4012 connecting to low speed bus 4014 and storage device 4006. Each of the components 4002, 4004, 4006, 4008, 4010, and 4012, are interconnected using various busses, and may be mounted on a common motherboard or in other manners as appropriate. The processor 4002 can process instructions for execution within the computing device 4000, including instructions stored in the memory 4004 or on the storage device 4006 to display graphical information for a GUI on an external input/output device, such as display 4016 coupled to high-speed interface 4008. In other implementations, multiple processors and/or multiple buses may be used, as appropriate, along with multiple memories and types of memory. Also, multiple computing devices 4000 may be connected, with each device providing portions of the necessary operations (e.g., as a server bank, a group of blade servers, or a multi-processor system).

The memory 4004 stores information within the computing device 4000. In one implementation, the memory 4004 is a volatile memory unit or units. In another implementation, the memory 4004 is a non-volatile memory unit or units. The memory 4004 may also be another form of computer-readable medium, such as a magnetic or optical disk.

The storage device 4006 is capable of providing mass storage for the computing device 4000. In one implementation, the storage device 4006 may be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 4004, the storage device 4006, or memory on processor 4002.

The high-speed controller 4008 manages bandwidth-intensive operations for the computing device 4000, while the low speed controller 4012 manages lower bandwidth-intensive operations. Such allocation of functions is by way of example only. In one implementation, the high-speed controller 4008 is coupled to memory 4004, display 4016 (e.g., through a graphics processor or accelerator), and to high-speed expansion ports 4010, which may accept various expansion cards (not shown). In the implementation, low-speed controller 4012 is coupled to storage device 4006 and low-speed expansion port 4014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 4000 may be implemented in a number of different forms, as shown in the figure. For example, it may be implemented as a standard server 4020, or multiple times in a group of such servers. It may also be implemented as part of a rack server system 4024. In addition, it may be implemented in a personal computer such as a laptop computer 4022. Alternatively, components from computing device 4000 may be combined with other components in a mobile device (not shown), such as device 4050. Each of such devices may contain one or more of computing device 4000, 4050, and an entire system may be made up of multiple computing devices 4000, 4050 communicating with each other.

Computing device 4050 includes a processor 4052, memory 4064, an input/output device such as a display 4054, a communication interface 4066, and a transceiver 4068, among other components. The device 4050 may also be provided with a storage device, such as a micro-drive or other device, to provide additional storage. Each of the components 4050, 4052, 4064, 4054, 4066, and 4068, are interconnected using various buses, and several of the components may be mounted on a common motherboard or in other manners as appropriate.

The processor 4052 can execute instructions within the computing device 4050, including instructions stored in the memory 4064. The processor may be implemented as a chipset of chips that include separate and multiple analog and digital processors. Additionally, the processor may be implemented using any of a number of architectures. For example, the processor 410 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 4050, such as control of user interfaces, applications run by device 4050, and wireless communication by device 4050.

Processor 4052 may communicate with a user through control interface 4058 and display interface 4056 coupled to a display 4054. The display 4054 may be, for example, a TFT (Thin-Film-Transistor Liquid Crystal Display) display or an OLED (Organic Light Emitting Diode) display, or other appropriate display technology. The display interface 4056 may comprise appropriate circuitry for driving the display 4054 to present graphical and other information to a user. The control interface 4058 may receive commands from a user and convert them for submission to the processor 4052. In addition, an external interface 4062 may be provided in communication with processor 4052, so as to enable near area communication of device 4050 with other devices. External interface 4062 may provide, for example, for wired communication in some implementations, or for wireless communication in other implementations, and multiple interfaces may also be used.

The memory 4064 stores information within the computing device 4050. The memory 4064 can be implemented as one or more of a computer-readable medium or media, a volatile memory unit or units, or a non-volatile memory unit or units. Expansion memory 4074 may also be provided and connected to device 4050 through expansion interface 4072, which may include, for example, a SIMM (Single In Line Memory Module) card interface. Such expansion memory 4074 may provide extra storage space for device 4050, or may also store applications or other information for device 4050. Specifically, expansion memory 4074 may include instructions to carry out or supplement the processes described above, and may include secure information also. Thus, for example, expansion memory 4074 may be provided as a security module for device 4050, and may be programmed with instructions that permit secure use of device 4050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, cause performance of one or more methods, such as those described above. The information carrier is a computer- or machine-readable medium, such as the memory 4064, expansion memory 4074, or memory on processor 4052 that may be received, for example, over transceiver 4068 or external interface 4062.

Device 4050 may communicate wirelessly through communication interface 4066, which may include digital signal processing circuitry where necessary. Communication interface 4066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 4068. In addition, short-range communication may occur, such as using a Bluetooth, WiFi, or other such transceiver (not shown). In addition, GPS (Global Positioning System) receiver module 4070 may provide additional navigation- and location-related wireless data to device 4050, which may be used as appropriate by applications running on device 4050.

Device 4050 may also communicate audibly using audio codec 4060, which may receive spoken information from a user and convert it to usable digital information. Audio codec 4060 may likewise generate audible sound for a user, such as through a speaker, e.g., in a handset of device 4050. Such sound may include sound from voice telephone calls, may include recorded sound (e.g., voice messages, music files, etc.) and may also include sound generated by applications operating on device 4050.

The computing device 4050 may be implemented in a number of different forms, some of which are shown in the figure. For example, it may be implemented as a cellular telephone 4080. It may also be implemented as part of a smartphone 4082, personal digital assistant, or other similar mobile device.

Additionally computing device 4000 or 4050 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the arespective computers and having a client-server relationship to each other.

FIG. 12 depicts a flowchart 12000 of an example process that may be performed by a portable medical treatment apparatus such as the portable medical treatment apparatus 1000, providing interactive guidance for a caregiver with little to no medical experience. The process includes presenting 12002 at least one first inquiry as part of an interactive query flow. The first query may be similar to elements 402b or 404b depicted above with respect to FIG. 4B. In some embodiments, the first query may distinguish whether to provide ALS instructions or BLS instructions as described above.

The process includes receiving 12004 at least one user input via the user interface in response to the at least one first inquiry. In embodiments, the at least one user input includes an indication that the patient is unconscious and not breathing, and based at least in part on the indication, the apparatus presents the user with the cardiac/pulmonary resuscitative treatment query protocol. In some embodiments, the user interface includes at least one of buttons, soft keys, a knob, a dial, or a touchscreen display, configured to receive the at least one input in response to the at least one inquiry, as described above with respect to portable medical treatment apparatus 1000.

The process includes presenting 12006, based on the at least one user input, at least one of a cardiac/pulmonary resuscitative treatment query flow and another medical treatment query flow. The cardiac/pulmonary resuscitative treatment query flow or the other medical treatment query flow may be similar to those depicted in, e.g., one or more of FIG. 4A, 4B, 4C, or 4D. In some embodiments, the other medical treatment query flow provides instructions for use of at least one of the plurality of medical supplies. In some embodiments, the other medical treatment query flow includes instructions for treating a condition other than cardiac arrest such as bleeding, seizure, burn, bone fracture, drug overdose, allergic reaction, choking, impaled object, trapped limb, severed body part, child birth, or confusion. In some embodiments, the cardiac/pulmonary resuscitative treatment query flow provides instructions for treating at least one of: a cardiac arrest condition and a respiratory distress condition and/or provides instructions for use of the plurality of electrodes. In some examples, user interface may include at least one of: touchscreen display device 3002, auxiliary display device 3048, input/output device 3047, auxiliary speaker 3050, secondary display device 3005, speaker 3012, or another appropriate user interface element, as described above with respect to FIGS. 2A-2B.

In some embodiments, the other medical treatment query flow relates to bleeding, and the inquiry at 12002, or an inquiry related to the other query flow at 12006, is a request for the user to input where the patient is bleeding. In some embodiments, the request for the user to input where the patient is bleeding includes a presentation on the user interface of a body with selectable regions to indicate where the patient is bleeding. In some embodiments, the at least one input includes a selected region that indicates where the victim is bleeding and the instructions for use of the at least one of the plurality of medical supplies comprise guidance for use of at least one of: the wound dressing, the hemostatic gauze, the pressuring dressing, the burn dressing, the compression dressing, and the tourniquet. In some embodiments, the other medical treatment query flow relates to seizing, and the at least one inquiry at 12002, or an inquiry related to the other query flow at 12006, includes a request for the user to ensure the patient is on their back. In some embodiments, the other medical treatment query flow relates to choking, and the at least one inquiry at 12002, or an inquiry related to the other query flow at 12006, includes a request for the user to perform an abdominal thrust.

FIG. 13 depicts a flowchart 1300 of an example process that may be performed by a portable medical treatment apparatus such as the portable medical treatment apparatus 1000, providing interactive guidance for a caregiver with little to no medical experience. The process includes presenting 13002 to a user via a user interface, at least one inquiry as part of the interactive query flow, the interactive query flow including a cardiac/pulmonary resuscitative treatment query flow that involves the apparatus analyzing a heart rhythm of a patient using the plurality of electrodes (e.g., electrodes 3020a or 3020b shown in FIG. 2B), and another medical treatment query flow. The at least one inquiry may be similar to elements 402b or 404b depicted above with respect to FIG. 4B. In some embodiments, the at least one inquiry may be to distinguish whether to provide ALS instructions or BLS instructions as described above. The cardiac/pulmonary resuscitative treatment query flow or the other medical treatment query flow may be similar to those depicted in, e.g., one or more of FIG. 4A, 4B, 4C, or 4D. In some embodiments, the other medical treatment query flow provides instructions for use of at least one of the plurality of medical supplies. In some embodiments, the other medical treatment query flow includes instructions for treating a condition other than cardiac arrest such as bleeding, seizure, burn, bone fracture, drug overdose, allergic reaction, choking, impaled object, trapped limb, severed body part, child birth, or confusion. In some embodiments, the cardiac/pulmonary resuscitative treatment query flow provides instructions for treating at least one of: a cardiac arrest condition and a respiratory distress condition and/or provides instructions for use of the plurality of electrodes.

The process may further include receiving 13004 at least one user input via the user interface in response to the at least one inquiry. In embodiments, the at least one user input includes an indication that the patient is unconscious and not breathing, and based at least in part on the indication, the apparatus is configured to present the user with the cardiac/pulmonary resuscitative treatment query protocol. In some embodiments, the user interface includes at least one of buttons, soft keys, a knob, a dial, or a touchscreen display, configured to receive the at least one input in response to the at least one inquiry, as described above with respect to portable medical treatment apparatus 1000.

The process may further include presenting 13006, based on the at least one user input, at least one of: the cardiac/pulmonary resuscitative treatment query flow or the other medical treatment query flow, via the user interface. The user interface may include one of touchscreen display device 3002, auxiliary display device 3048, input/output device 3047, auxiliary speaker 3050, secondary display device 3005, speaker 3012, or another appropriate user interface element, as described above with respect to FIGS. 2A-2B.

The process includes determining 13008, based on an electrical signal from at least one sensor, the removal of a medical item from among the plurality of medical supplies. The at least one sensor may include at least one of: a photodetector, an optical sensor, an image sensor, a Hall effect sensor, a capacitive sensor, a motion sensor, a weight sensor, a force sensor, an electro-magnetic sensor, a proximity sensor. The plurality of medical supplies may include at least one of: gloves, a wound dressing, hemostatic gauze, a pressuring dressing, a burn dressing, a compression dressing. a splint, a tourniquet, a drug dosage, and an emergency blanket.

The process includes navigating 13010 to a portion of the interactive query flow related to use of the removed medical item, and presenting, via the user interface, the interactive query flow related to use of the removed medical item, e.g., as described above with respect to FIG. 5.

In some embodiments, the other medical treatment query flow relates to bleeding, and the inquiry at 13002, or an inquiry related to the other query flow at 13006, is a request for the user to input where the patient is bleeding. In some embodiments, the request for the user to input where the patient is bleeding includes a presentation on the user interface of a body with selectable regions to indicate where the patient is bleeding. In some embodiments, the at least one input includes a selected region that indicates where the victim is bleeding and the instructions for use of the at least one of the plurality of medical supplies comprise guidance for use of at least one of: the wound dressing, the hemostatic gauze, the pressuring dressing, the burn dressing, the compression dressing, and the tourniquet. In some embodiments, the other medical treatment query flow relates to seizing, and the at least one inquiry at 13002, or an inquiry related to the other query flow at 13006, includes a request for the user to ensure the patient is on their back. In some embodiments, the other medical treatment query flow relates to choking, and the at least one inquiry at 13002, or an inquiry related to the other query flow at 13006, includes a request for the user to perform an abdominal thrust.

FIG. 14 depicts a flowchart 14000 of an example process that may be performed by a portable medical treatment apparatus such as portable medical treatment apparatus 1000. The process includes presenting, at 14002, to a user via a user interface, at least one inquiry as part of an interactive query flow. The process includes receiving 14004 at least one input via the user interface in response to the at least one inquiry. The process includes presenting 14006, to the user, based on the at least one user input, at least one of: a cardiac/pulmonary resuscitative treatment query flow or another medical treatment query flow, via the user interface. These steps may be respectively similar to steps 12002, 12004, and 12006 as described above with respect to FIG. 12.

The process includes determining 14008, based on an electrical signal from the at least one sensor, the removal of the plurality of electrodes, e.g., as described above with respect to one or more of FIG. 2A, 2B, 3A, 3B, or 3C.

The process includes navigating 14010 to the cardiac/pulmonary resuscitative treatment query flow and presenting, via the user interface, guidance related to use of the removed plurality of electrodes. The guidance may be as described above with respect to FIG. 4A and FIG. 5.

FIG. 15 shows a flowchart 15000 of an example process that may be performed by a portable medical treatment apparatus such as portable medical treatment apparatus 1000. The process includes analyzing 15002, by the portable medical treatment apparatus during a first time period, a heart rhythm of a patient that is sensed using a plurality of defibrillation electrodes (e.g., electrodes 3020$a$ or 3020$b$ shown in FIG. 2B) of the portable medical treatment apparatus. This analysis may be similar to the analysis described above with respect to FIG. 7A or 7B.

The process includes determining 15004, by the portable medical treatment apparatus, that the heart rhythm that is sensed during the first time period does not satisfy criteria for delivering a shock to the patient. This determination may be similar to that described above with respect to element 5310 shown in FIG. 5, or as described above with respect to FIG. 7A or 7B.

The process includes presenting 15006, by the portable medical treatment apparatus in response to the portable medical treatment apparatus having determined that the heart rhythm that is sensed during the first time period does not satisfy criteria for delivering the shock to the patient, an interactive query flow configured to guide a user of the portable medical treatment apparatus in assessing and treating non-cardiac arrest medical emergencies. This query flow may be similar to that described with respect to element 5330 shown in FIG. 5.

The process may further include subsequently analyzing, by the portable medical treatment apparatus during a second time period that occurs after the portable medical treatment apparatus has presented multiple prompts and received multiple user responses as part of the interactive query flow, the heart rhythm of the patient using the plurality of defibrillation electrodes. The second time period may be as discussed above with respect to elements 5320 or 5340, and the analysis may be similar to that discussed above with respect to element 5310, shown in FIG. 5.

The processes of FIGS. 12-15 are intended herein as example processes, and other embodiments may include more or fewer elements than are depicted, elements arranged in a different order than depicted (e.g., consecutively with one another or performed in a different order), or some other variation.

While the inventive features described herein have been described in terms of a preferred embodiment for achieving the objectives, it will be appreciated by those skilled in the art that variations may be accomplished in view of these teachings without deviating from the spirit or scope of the present disclosure.

What is claimed is:

1. A portable medical treatment and guidance apparatus with resuscitative functionality, the apparatus comprising:
   a case having at least one compartment;
   a plurality of medical supplies housed within the at least one compartment;
   at least one capacitor housed within the case, the at least one capacitor configured to store energy sufficient for providing an electrical defibrillation discharge;

a user interface mechanically coupled to the case and configured to provide an interactive query flow for assisting a user in providing medical treatment to a patient;

a cardiac/pulmonary resuscitative subsystem being communicatively coupled to the case and including a plurality of electrodes configured to be electrically coupled to the at least one capacitor via an electrical connection between the cardiac/pulmonary resuscitative subsystem and the case;

at least one sensor configured to sense a removal of a medical item from among the plurality of medical supplies and the plurality of electrodes; and at least one processor and memory mechanically coupled to the case and electrically coupled to the at least one capacitor, the user interface and the sensor, the at least one processor and memory configured to:

present via the user interface at least one first inquiry as part of the interactive query flow, receive at least one user input via the user interface in response to the at least one first inquiry, present to the user via the user interface and based on the at least one user input a selected one or both of: a cardiac/pulmonary resuscitative treatment query flow for guiding the user in providing the medical treatment to the patient, and an other medical treatment query flow for guiding the user in providing the medical treatment to the patient;

in response to a selection of the cardiac/pulmonary resuscitative treatment query flow by the user, receive patient cardiac activity data via the plurality of electrodes coupled to the patient and charge the at least one capacitor in preparation for electrical defibrillation discharge;

via the user interface, determine, based on an electrical signal from the at least one sensor, the removal of a medial item from among the plurality of medical supplies;

navigate to a portion of the interactive query flow related to use of the removed medical item and present, via the user interface, the portion of the interactive query flow related to use of the removed medical item; and revert back to the cardiac/pulmonary resuscitative treatment query flow upon provision of guidance pertaining to the portion of the interactive query flow related to use of the removed medical item.

2. The apparatus of claim 1, wherein the other medical treatment query flow provides instructions for use of at least one of the plurality of medical supplies.

3. The apparatus of claim 1, wherein the other medical treatment query flow comprises instructions for treating a condition other than cardiac arrest.

4. The apparatus of claim 1, wherein the cardiac/pulmonary resuscitative treatment query flow provides instructions for treating at least one of: a cardiac arrest condition and a respiratory distress condition.

5. The apparatus of claim 1, wherein the at least one user input comprises an indication that the patient is unconscious and not breathing, and based at least in part on the indication, the at least one processor and memory are configured to present the user with the cardiac/pulmonary resuscitative treatment query flow.

6. The apparatus of claim 1, wherein the user interface comprises at least one of: buttons, soft keys, a knob, a dial, or a touchscreen display, configured to receive the at least one input in response to the at least one inquiry.

7. The apparatus of claim 1, wherein the at least one processor and memory is configured to start a timer upon beginning the interactive query flow.

8. The apparatus of claim 1, wherein the at least one processor and memory is configured to provide continuous background monitoring during the interactive query flow.

9. The apparatus of claim 1, wherein:
the removed medical item comprises gauze; and
the portion of the interactive query flow related to use of the gauze comprises a portion of the interactive query flow related to an injury that causes blood loss.

10. The apparatus of claim 1, wherein the at least one processor and memory is configured to present via the user interface an inquiry as to a level of medical training of the user, and receive a response to the inquiry as to the level of medical training of the user.

11. The apparatus of claim 1, wherein the cardiac/pulmonary resuscitative subsystem is removably coupled to the case.

12. A portable medical treatment and guidance apparatus with electrotherapy functionality, the apparatus comprising:
a case having at least one compartment;
a plurality of medical supplies housed within the at least one compartment;
at least one capacitor housed within the case, the at least one capacitor configured to store energy sufficient for providing an electrical defibrillation discharge;
a plurality of electrodes housed within the at least one compartment and configured to be electrically coupled to the at least one capacitor;
at least one sensor configured to sense a removal of a medical item from among the plurality of medical supplies and the plurality of electrodes;
a user interface mechanically coupled to the case and configured to provide an interactive query flow; and
at least one processor and memory mechanically coupled to the case and electrically coupled to the at least one capacitor, the user interface and the sensor, the at least one processor and memory configured to:
present to a user via the user interface at least one inquiry as part of the interactive query flow, the interactive query flow including a cardiac/pulmonary resuscitative treatment query flow that involves the apparatus analyzing a heart rhythm of a patient using the plurality of electrodes, and an other medical treatment query flow for guiding the user in providing medical treatment to the patient,
receive at least one user input via the user interface in response to the at least one inquiry, present to the user, based on the at least one user input, at least one of: the cardiac/pulmonary resuscitative treatment query flow or the other medical treatment query flow,
via the user interface, determine, based on an electrical signal from the at least one sensor, the removal of a medical item from among the plurality of medical supplies,
navigate from a first portion of the interactive query flow to a second portion of the interactive query flow related to use of the removed medical item and present, via the user interface, the second portion of the interactive query flow related to use of the removed medical item; and
revert back to the first portion of the interactive query flow upon provision of guidance pertaining to the second portion of the interactive query flow related to use of the removed medical item.

13. The apparatus of claim 12, wherein the at least one sensor comprises at least one of: a photodetector, an optical sensor, an image sensor, a Hall effect sensor, a capacitive sensor, a motion sensor, a weight sensor, a force sensor, an electro-magnetic sensor, a proximity sensor.

14. The apparatus of claim 12, wherein the at least one sensor is configured to detect removal of the plurality of electrodes, and the at least one processor and memory are configured to navigate to the cardiac/pulmonary resuscitative treatment query flow.

15. The apparatus of claim 12, wherein the other medical treatment query flow provides instructions for use of at least one of the plurality of medical supplies.

16. The apparatus of claim 12, wherein the other medical treatment query flow comprises instructions for treating a condition other than cardiac arrest.

17. An automated external defibrillator for providing guidance in administering emergency medical treatment, the automated external defibrillator comprising:

at least one capacitor configured to provide electro-therapy;

a plurality of medical supplies;

a plurality of electrodes configured to be electrically coupled to the at least one capacitor;

at least one sensor adapted to identify removal of the plurality of electrodes or sense a removal of a medical item from among the plurality of medical supplies;

a user interface configured to provide an interactive query flow that includes a cardiac/pulmonary resuscitative treatment query flow that involves analysis of a heart rhythm of a patient using the plurality of electrodes and an other medical treatment query flow for guiding a user in providing medical treatment to the patient; and at least one processor and memory electrically coupled to the at least one capacitor, the plurality of electrodes, and the user interface, the at least one processor and memory configured to:

present to the user via the user interface at least one inquiry as part of the interactive query flow, receive at least one input via the user interface in response to the at least one inquiry, present to the user, based on the at least one user input, at least one of: a cardiac/pulmonary resuscitative treatment query flow or an other medical treatment query flow, via the user interface, determine, based on an electrical signal from the at least one sensor, the removal of the plurality of electrodes, navigate to the cardiac/pulmonary resuscitative treatment query flow and present, via the user interface, guidance related to use of the removed plurality of electrodes;

receive, from the plurality of electrodes, patient cardiac data characterizing cardiac activity of the patient and charge the at least one capacitor in preparation for providing the electrical defibrillation discharge to the patient;

via the user interface, determine, based on an electrical signal from the at least one sensor, the removal of a medical item from among the plurality of medical supplies;

navigate to a portion of the interactive query flow related to use of the removed medical item and present, via the user interface, the portion of the interactive query flow related to use of the removed medical item; and revert back to the cardiac/pulmonary resuscitative treatment query flow upon provision of guidance pertaining to the portion of the interactive query flow related to use of the removed medical item.

18. The automated external defibrillator of claim 17, wherein the at least one sensor comprises at least one of: a photodetector, an optical sensor, an image sensor, a Hall effect sensor, a capacitive sensor, a motion sensor, a weight sensor, a force sensor, an electro-magnetic sensor, a proximity sensor.

19. The automated external defibrillator of claim 17, wherein the other medical treatment query flow provides instructions for use of at least one of the plurality of medical supplies.

20. The automated external defibrillator of claim 17, wherein the other medical treatment query flow comprises instructions for treating a condition other than cardiac arrest.

* * * * *